United States Patent [19]
Godowski et al.

[11] Patent Number: 6,025,145
[45] Date of Patent: *Feb. 15, 2000

[54] KINASE RECEPTOR ACTIVATION ASSAY

[75] Inventors: Paul J. Godowski; Melanie R. Mark, both of Burlingame; Michael Daniel Sadick, El Cerrito; Wai Lee Tan Wong, Los Altos Hills, all of Calif.

[73] Assignee: Genentech, Inc., South San Francisco, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/374,565
[22] PCT Filed: Nov. 18, 1994
[86] PCT No.: PCT/US94/13329
   § 371 Date: Jan. 20, 1995
   § 102(e) Date: Jan. 20, 1995
[87] PCT Pub. No.: WO95/14930
   PCT Pub. Date: Jun. 1, 1995

Related U.S. Application Data

[63] Continuation-in-part of application No. 08/286,305, Aug. 5, 1994, Pat. No. 5,766,863, which is a continuation-in-part of application No. 08/170,558, Dec. 20, 1993, which is a continuation-in-part of application No. 08/157,563, Nov. 23, 1993, abandoned.

[51] Int. Cl.[7] ................................................. C12Q 1/48
[52] U.S. Cl. ........................... 435/7.2; 435/15; 435/69.1; 435/194; 435/325
[58] Field of Search .................................. 435/7.2, 69.1, 435/325, 240.2, 194, 15

[56] References Cited

U.S. PATENT DOCUMENTS

| | | | |
|---|---|---|---|
| 4,654,299 | 3/1987 | Lentfer | 435/7 |
| 4,859,609 | 8/1989 | Dull et al. | 436/501 |
| 5,336,603 | 8/1994 | Capon et al. | 435/69.7 |
| 5,599,681 | 2/1997 | Epstein et al. | 435/7.23 |

FOREIGN PATENT DOCUMENTS

| | | |
|---|---|---|
| 244221 | 4/1987 | European Pat. Off. . |
| 8804692 | 6/1988 | WIPO . |
| 93/15201 | 5/1993 | WIPO . |
| 94/19463 | 1/1994 | WIPO . |

*Primary Examiner*—Sally P. Teng
*Attorney, Agent, or Firm*—Flehr Hohbach Test Albritton and Hebert LLP; Robin M. Silva; Mark T. Kresnak

[57] ABSTRACT

An assay for measuring activation (i.e., autophosphorylation) of a tyrosine kinase receptor of interest is disclosed. a) A first solid phase is coated with a substantially homogeneous population of cells so that the cells adhere to the first solid phase. The cells have either an endogenous tyrosine kinase receptor or have been transformed with DNA encoding a receptor or "receptor construct" and the DNA has been expressed so that the receptor or receptor construct is presented in the cell membranes of the cells. b) A ligand is then added to the solid phase having the adhering cells, such that the tyrosine kinase receptor is exposed to the ligand. c) Following exposure to the ligand, the adherent cells are solubilized, thereby releasing cell lysate. d) A second solid phase is coated with a capture agent which binds specifically to the tyrosine kinase receptor, or, in the case of a receptor construct to the flag polypeptide. e) The cell lysate obtained in step c) is added to the wells containing the adhering capture agent so as to capture the receptor or receptor construct to the wells. f) A washing step is then carried out, so as to remove unbound cell lysate, leaving the captured receptor or receptor construct. g) The captured receptor or receptor construct is exposed to a labelled anti-phosphotyrosine antibody which identifies phosphorylated residues in the tyrosine kinase receptor. h) Binding of the anti-phosphotyrosine antibody to the captured receptor or receptor construct is measured.

31 Claims, 70 Drawing Sheets

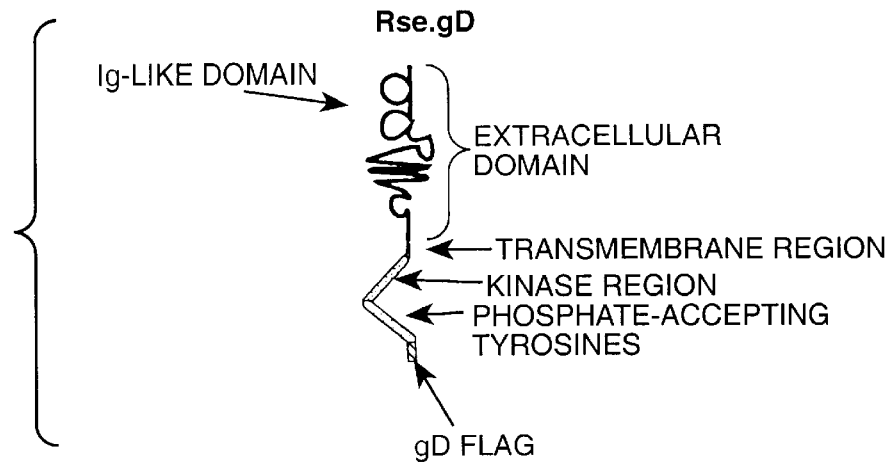
FIG._1A
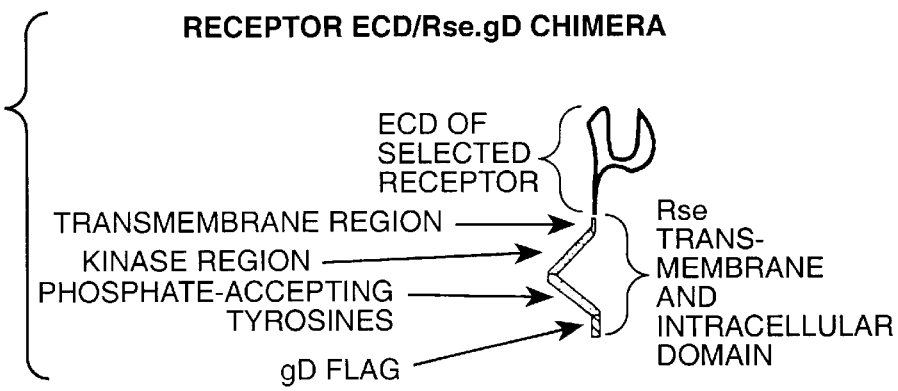
FIG._1B
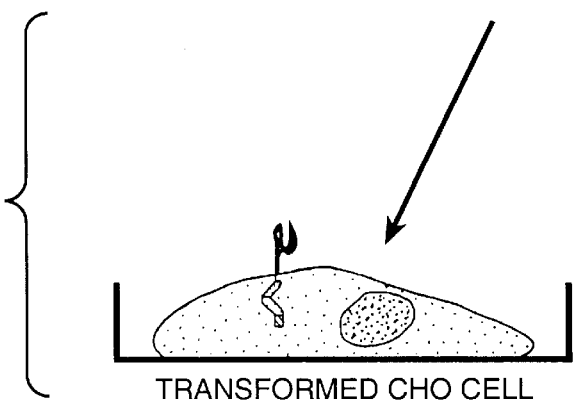
FIG._1C

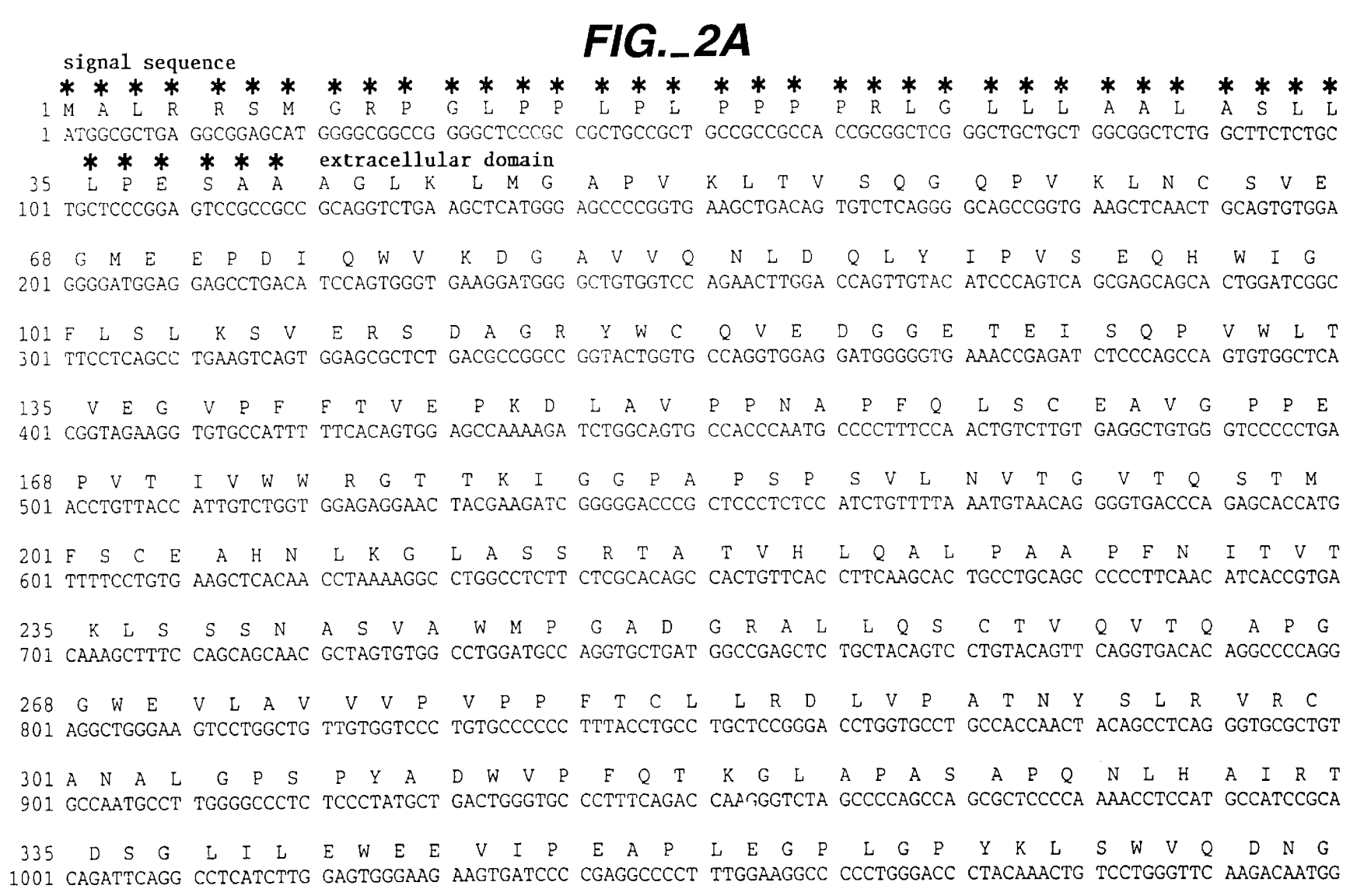

```
368   T Q D   E L T V   E G T   R A N   L T G W   D P Q   K D L   I V R V   C V S   N A V
1101  AACCCAGGAT GAGCTGACAG TGGAGGGAC CAGGGCCAAT TTGACAGGCT GGGATCCCCA AAAGGACCTG ATCGTACGTG TGTGCGTCTC CAATGCAGTT
                                                                                                  transmembrane domain
401   G C G P   W S Q   P L V   V S S H   D R A   G Q Q   G P P H   S R T   S W V P V V L
1201  GGCTGTGGAC CCTGGAGTCA GCCACTGTGG GTCTCTTCTC ATGACCGTGC AGGCCAGCAG GGCCCTCCTC ACAGCCGCAC ATCCTGGGTA CCTGTGGTCC 435   G V L   T A L   V T A A   A L I L   R K R   R K E   T R F   G Q A F   D S V
1301  TTGGTGTGCT AACGGGCCTG GTGACGGCTG CTGCCCTGGC CCTCATCCTG CTTCGAAAGA GACGGAAAGA GACGCGGTTT GGGCAAGCCT TTGACAGTGT
                                       intracellular domain
468   M A R   G E P A   V H F   R A A   R S F N   R E R   P E R   I E A T   L D S   L G I
1401  CATGGCCCGG GGAGAGCCAG CCGTTCACTT CCGGGCAGCC CGGTCCTTCA ATCGAGAAAG GCCCCGAGCG ATCGAGGCCA CATTGGACAG CTTGGGCATC 501   S D E L   K E K   L E D   V L I P   E Q Q   D G S F   V K V   A V K   M L K A   D I I   A S S   D I E E   F L R
1501  AGCGATGAAC TAAAGGAAAA ACTGGAGGAT GTGCTCATCC CAGAGCAGCA GGATGGCTCC TTTGTGAAAGT GGCTGTGAAA ATGCTGAAAG CTGACATCAT TGCCTCCAGC GACATTGAAG AGTTCCTCAG 535   A Q L   K Q E   D G S F   V K V   A V K   M L K A   D I I   A S S   D I E E   F L R
1601  AGGCCCAGCT GAAGCAAGAG GATGGCTCCT TTGTGAAAGT GGCTGTGAAA ATGCTGAAAG CTGACATCAT TGCCTCCAGC GACATTGAAG AGTTCCTCAG 568   E A A   C M K E   F D H   P H V   A K L V   G V S   L R S   R A K G   R L P   I P M
1701  GGAAGCAGCT TGCATGAAGG AGTTTGACCA TCCACACGTG GCCAAACTTG TTGGGGTAAG CCTCCGGAGC AGGGCTAAAG GCCGTCTCCC CATCCCCATG 601   V I L P   F M K   H G D   L H A F   L L A   S R I   G E N P   F N L   P L Q   T L I R
1801  GTCATCTTGC CCTTCATGAA GCATGGGGAC CTGCACGCCT TCCTGCTCGC CTCCCGGATT GGGGAGAACC CCTTTAACCT ACCCCTCCAG ACCCTGATCC 635   F M V   D I A   C G M E   Y L S   S R N   F I H R   D L A   A R N   C M L A   E D M
1901  GTTCATGGTT GGACATTGCC TGCGGCATGG AGTACCTGAG CTCTCGGAAC TTCATCCACC GAGACCTGGC TGCTCGGAAT TGCATGCTGG CAGAGGACAT 668   T V C   V A D F   G L S   R K I   Y S G D   Y Y R   Q G C   A S K L   P V K   W L A
2001  GACAGTGTGT GTGGCTGACT TCGGACTCTC CCGGAAGATC TACTACTATCG TCAAGGCTGT GCCTCCAAAC GCCTCCCAAC GCCTCAAGTT GGCTGGCC
```

FIG._2C

```
701  L   E   S   L   A   D   N   L   Y   T   V   Q   S   D   V   W   A   F   G   V   T   M   W   E   I   M   T   R   G   Q   T   P   Y   A
2101 CTGGAGAGCC TGGCCGACAA CCTGTATACT GTGCAGAGTG ACGTGTGGGC GTTCGGGGTG ACCATGTGGG AGATCATGAC ACGTGGGCAG ACGCCATATG

735  G   I   E   N   A   E   I   Y   N   Y   L   I   G   N   R   L   K   Q   P   P   E   C   M   E   D   V   Y   D   L   M   Y   Q
2201 CTGGCATCGA AAACGCTGAG ATTTACAACT ACCTCATTGG CGGGAACCGC CTGAAACAGC CTCCGGAGTG TATGGAGGAC GTGTATGATC TCATGTACCA

768  C   W   S   A   D   P   K   Q   R   P   S   F   T   C   L   R   M   E   L   E   N   I   L   G   Q   L   S   V   L   S   A   S   Q
2301 GTGCTGGAGT GCTGACCCCA AGCAGCGGCC CAGCTTTACT TGTCTGCGAA TGGAACTGGA GAACATCTTG GGCCAGCTGT CTGTGCTATC TGCCAGCCAG

801  D   P   L   Y   I   N   I   E   R   A   E   E   P   T   A   G   G   S   L   E   L   P   G   R   D   Q   P   Y   S   G   A   G   D   G
2401 GACCCCTTAT ACATCAACAT CGAGAGAGCT GAGGAGCCCA CTGCGGGAGG CAGCCTGGAG CTACCTGGCA GGGATCAGCC CTACAGTGGG GCTGGGGATG

835  S   G   M   G   A   V   G   G   T   P   S   D   C   R   Y   I   L   T   P   G   G   L   A   E   Q   P   G   Q   A   E   H   Q   P
2501 GCAGTGGCAT GGGGGCAGTG GGTGGCCACTC CCAGTGACTG TCGGTACATA CTCACCCCCG GAGGGCTGGC TGAGCAGCCA GGGCAGGCAG AGCACCAGCC

868  E   S   P   L   N   E   T   Q   R   L   L   L   L   Q   Q   G   L   P   H   S   S   C           gD flag polypeptide
                                                                                          A   D   A   S   L   K   M   A   D   P
2601 AGAGAGTCCC CTCAATGAGA CACAGAGGCT TTTGCTGCTG CAGCAAGGGC TACTGCCACA CTCGAGCTGC GCAGATGCTA GCCTCAAGAT GGCTGATCCA 901  N   R   F   R   G   K   D   L   P   V   L   Q
2701 AATCGATTCC GCGGCAAAGA TCTTCCGGTC CTGTAGAAGC TT
```

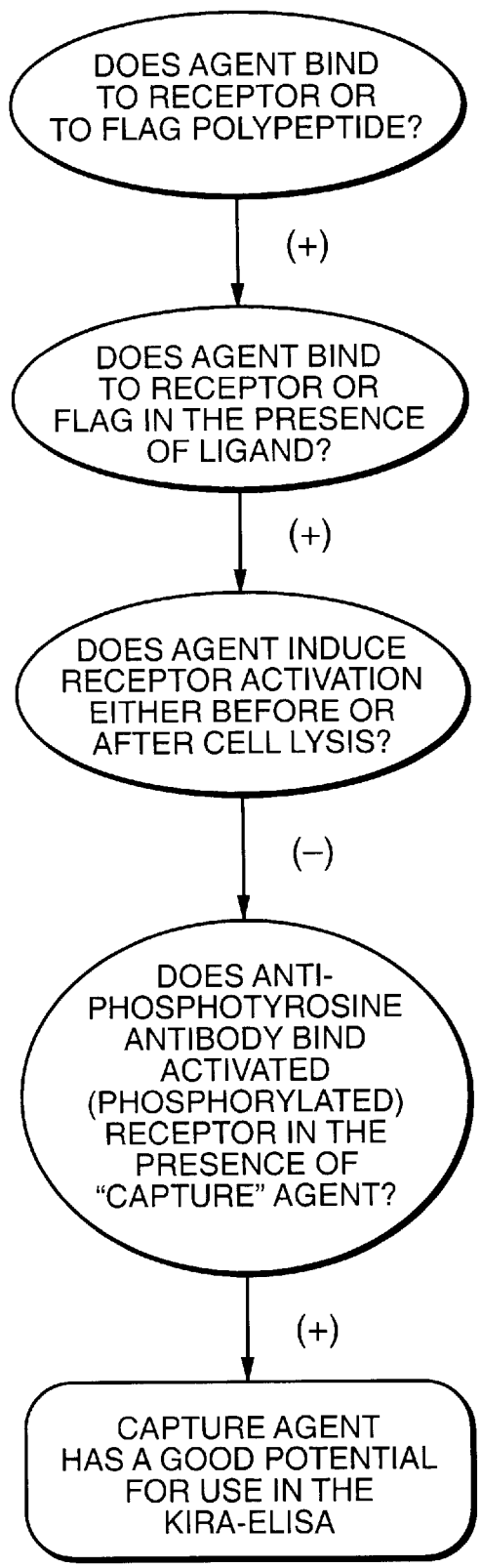
FIG._3

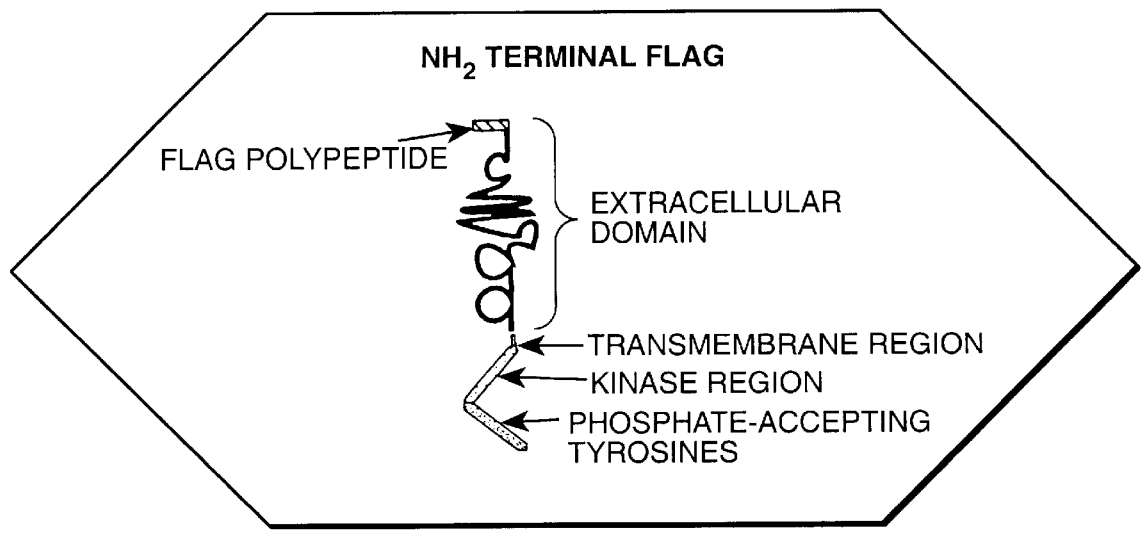
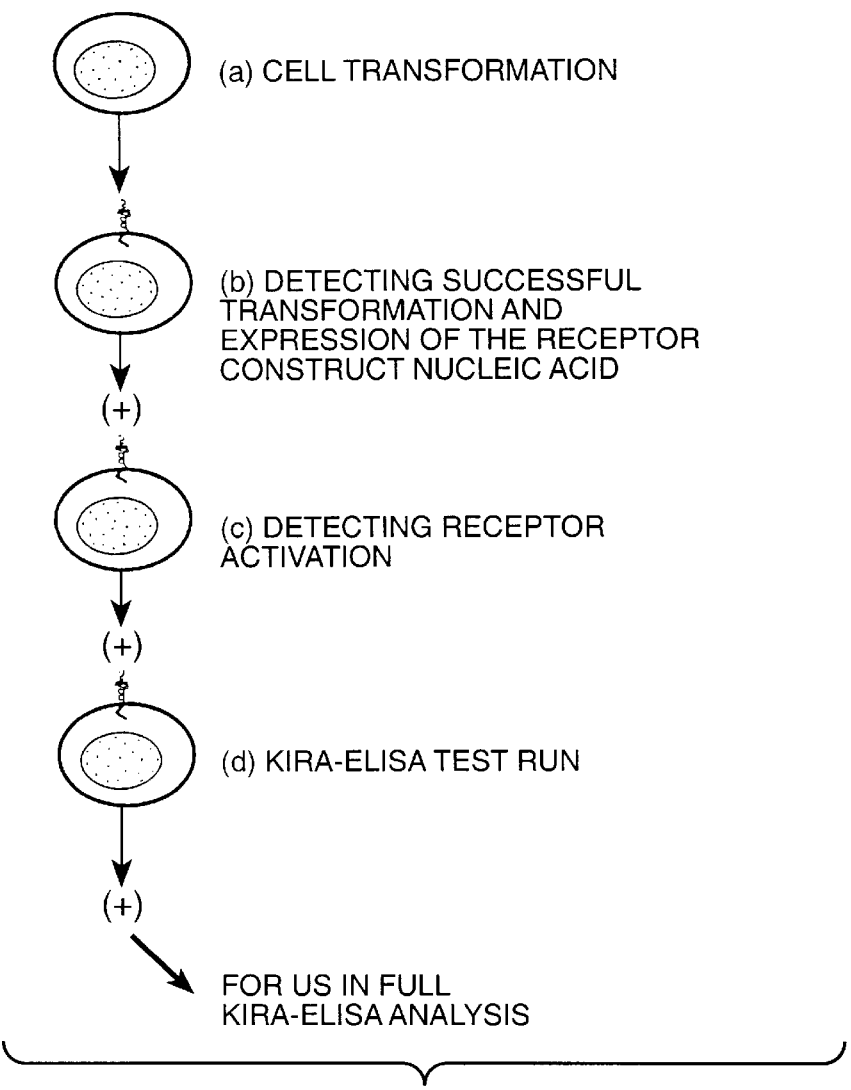
FIG._4

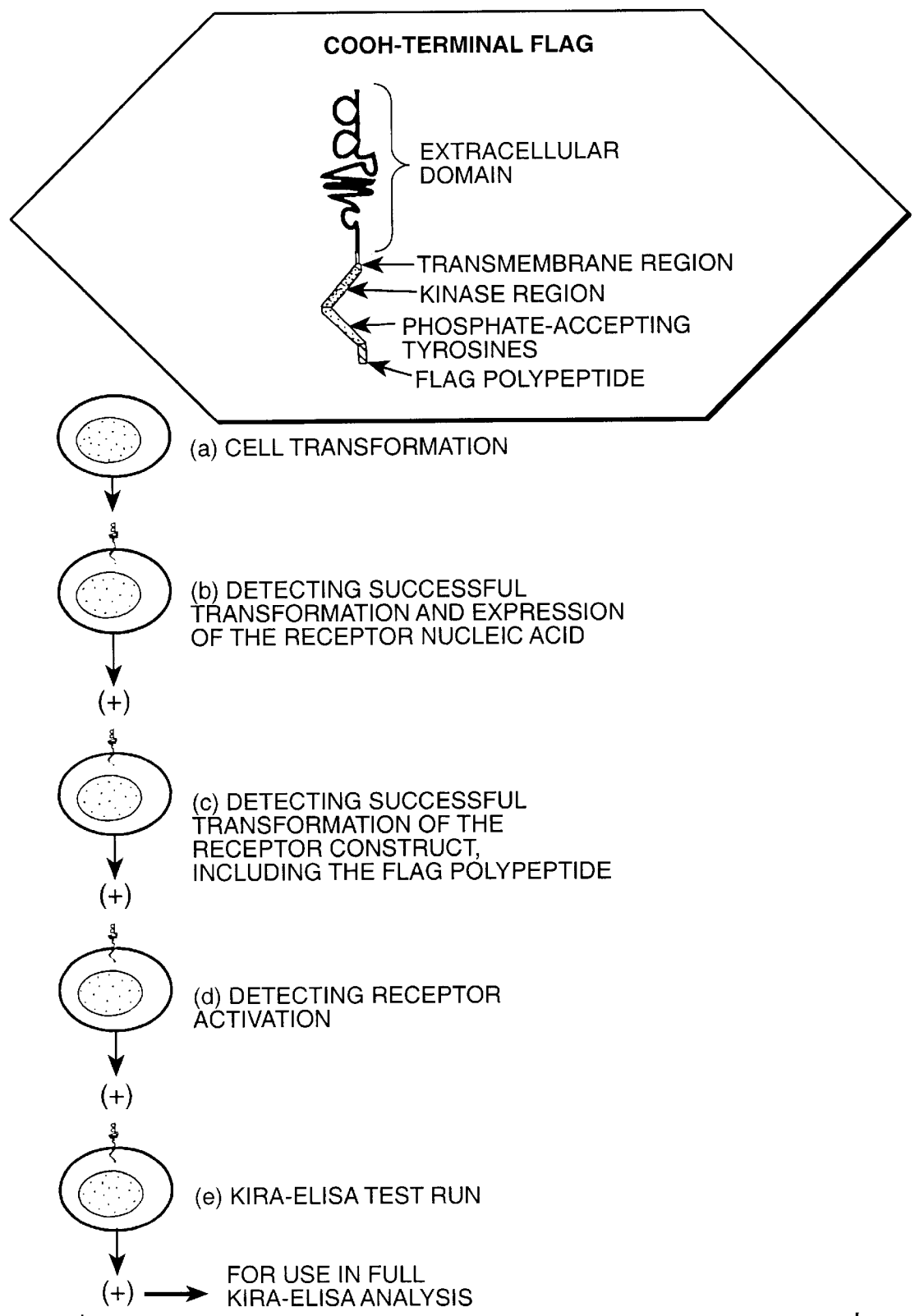
FIG._5

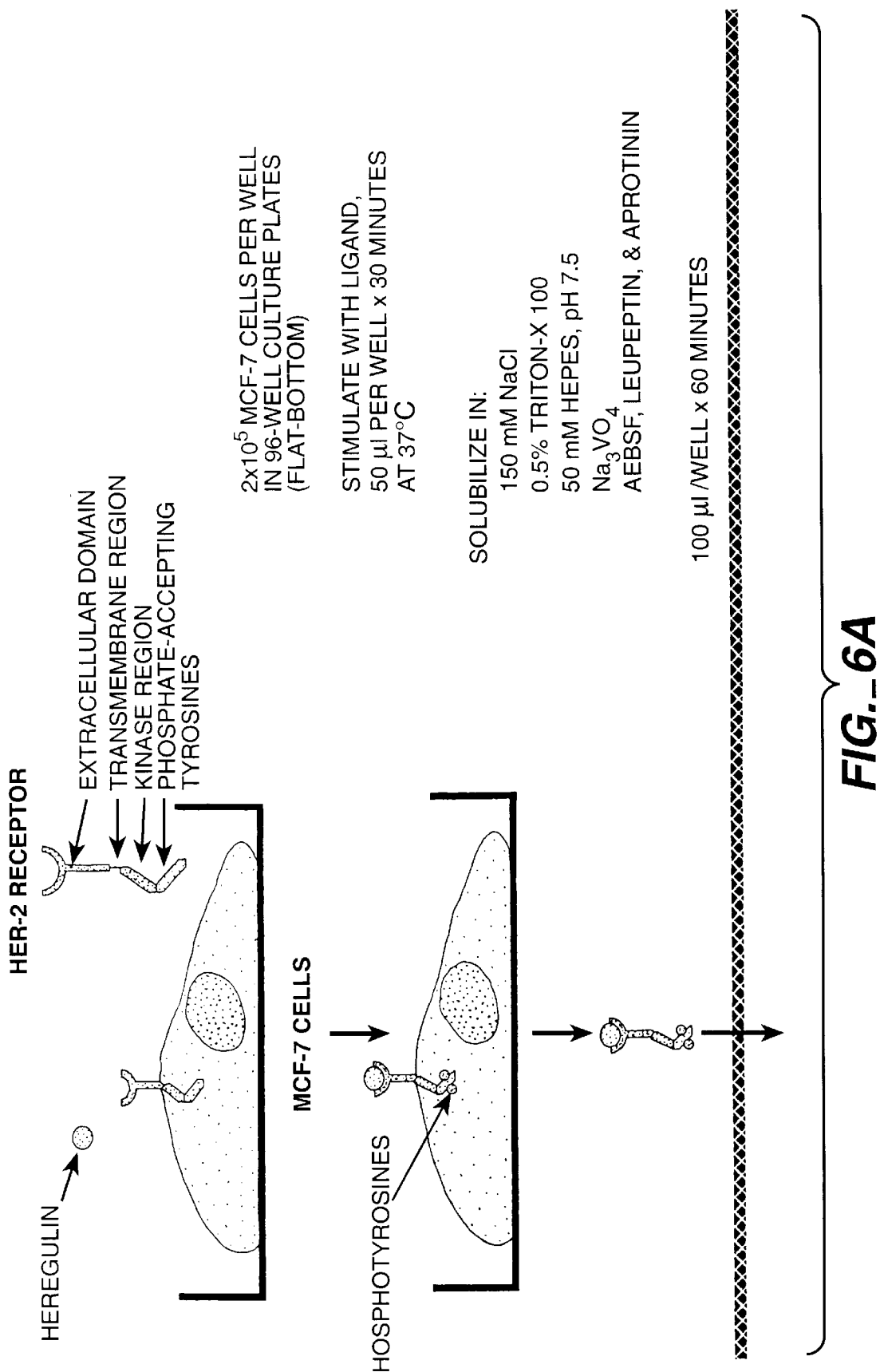
FIG._6A

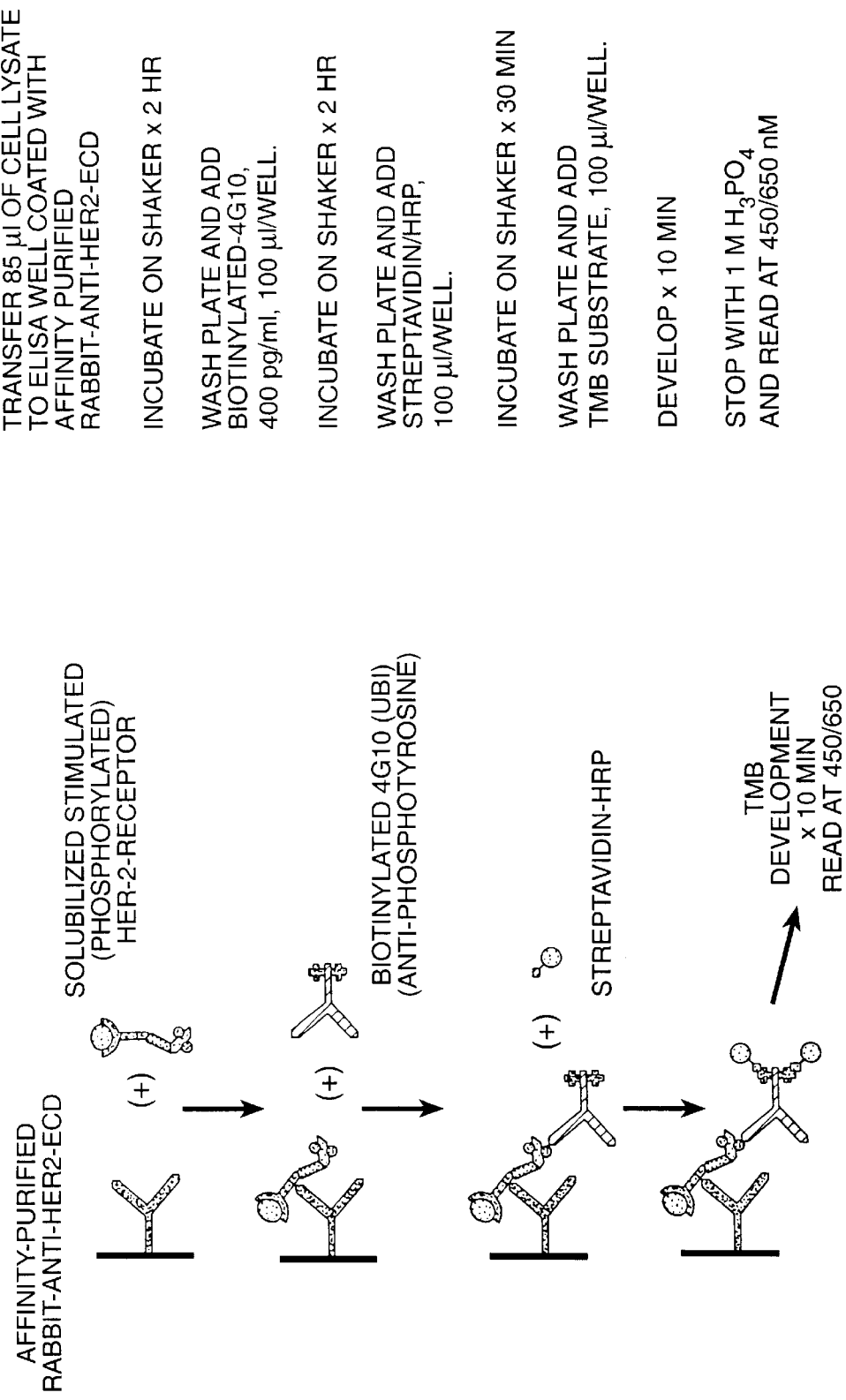
FIG._6B

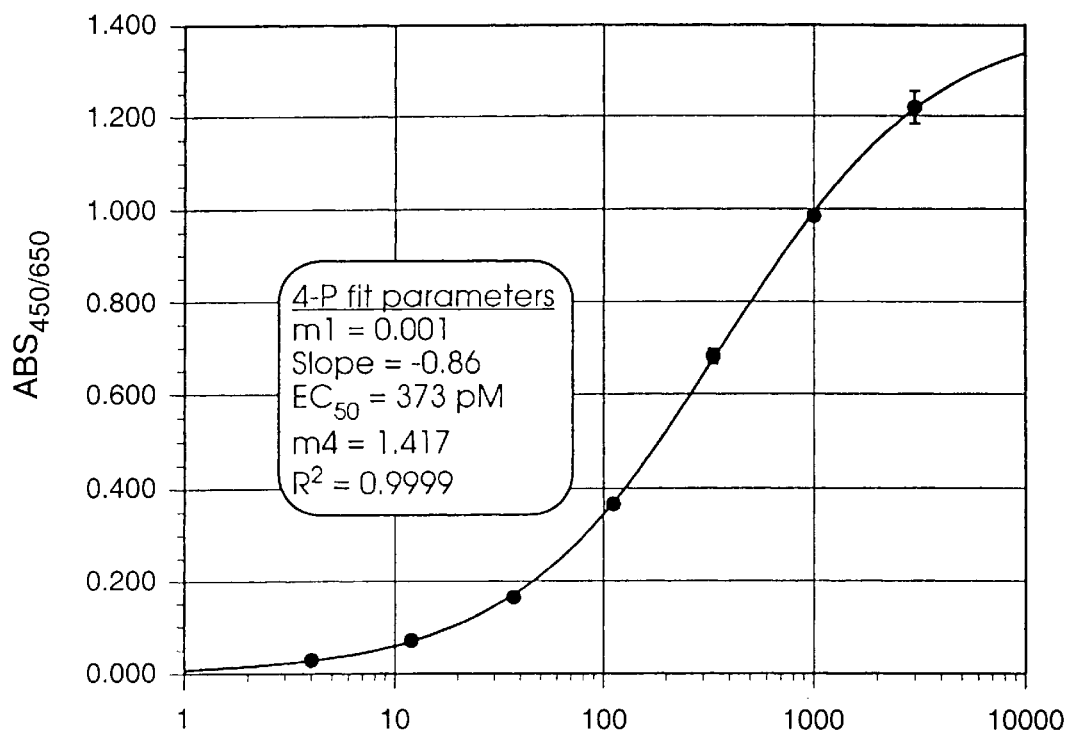
FIG._7
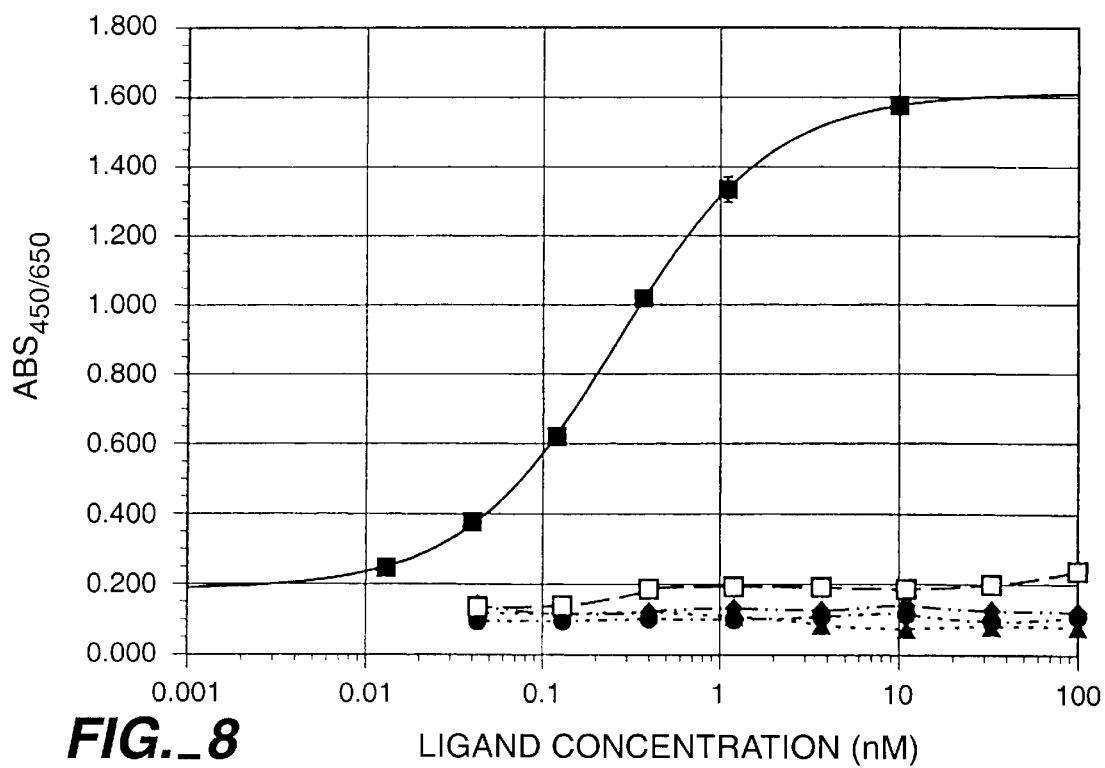
FIG._8

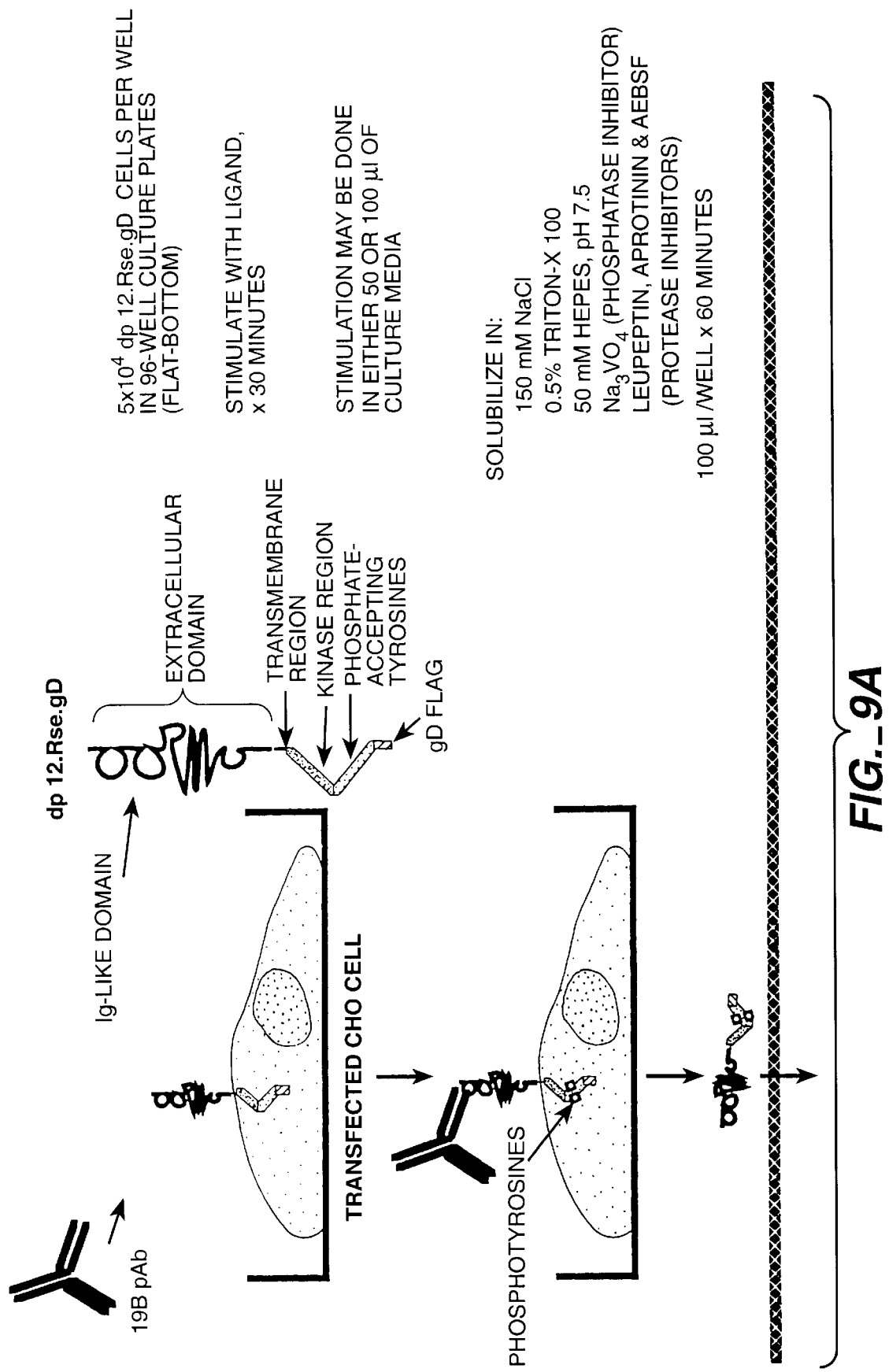
FIG._9A

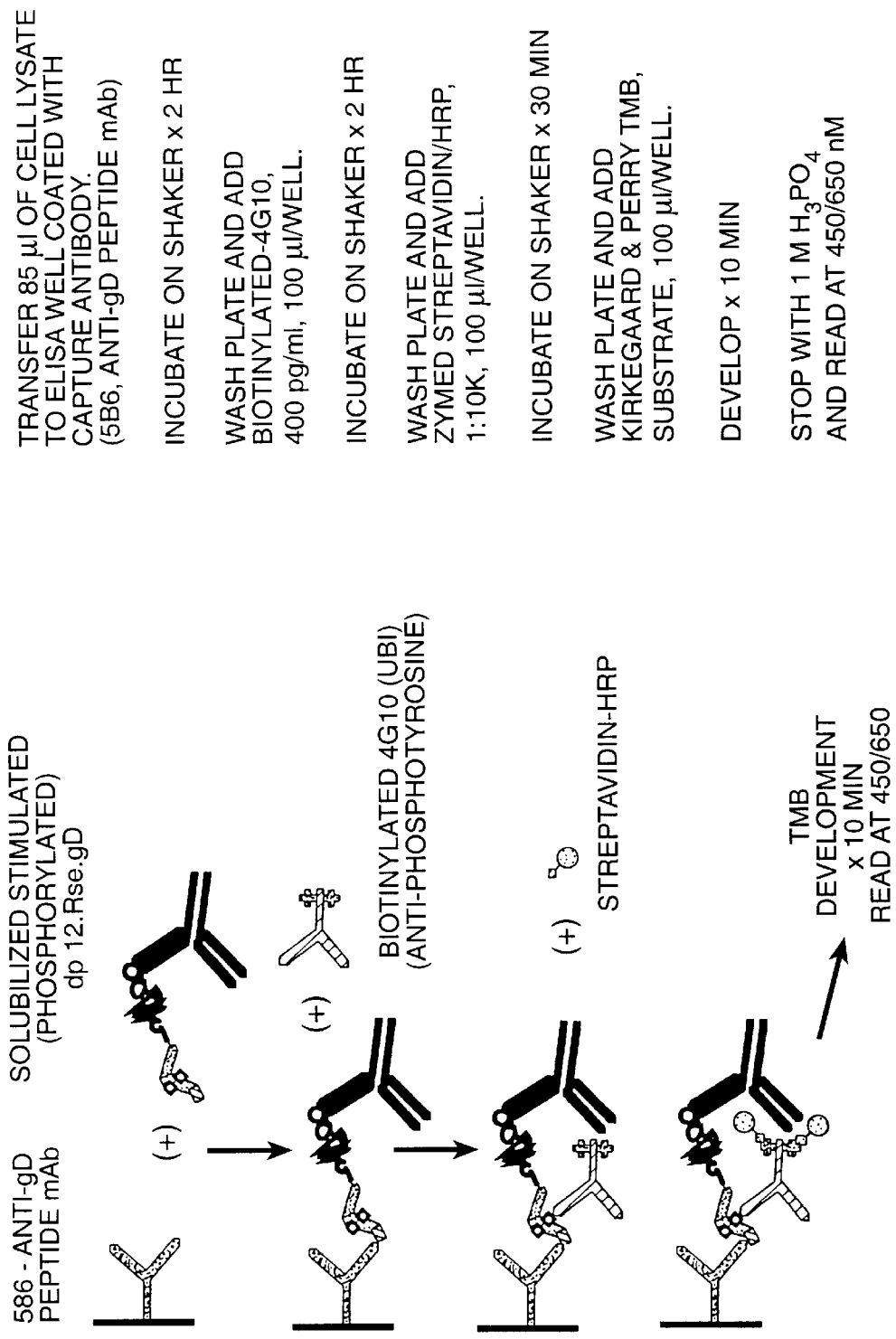
FIG._9B

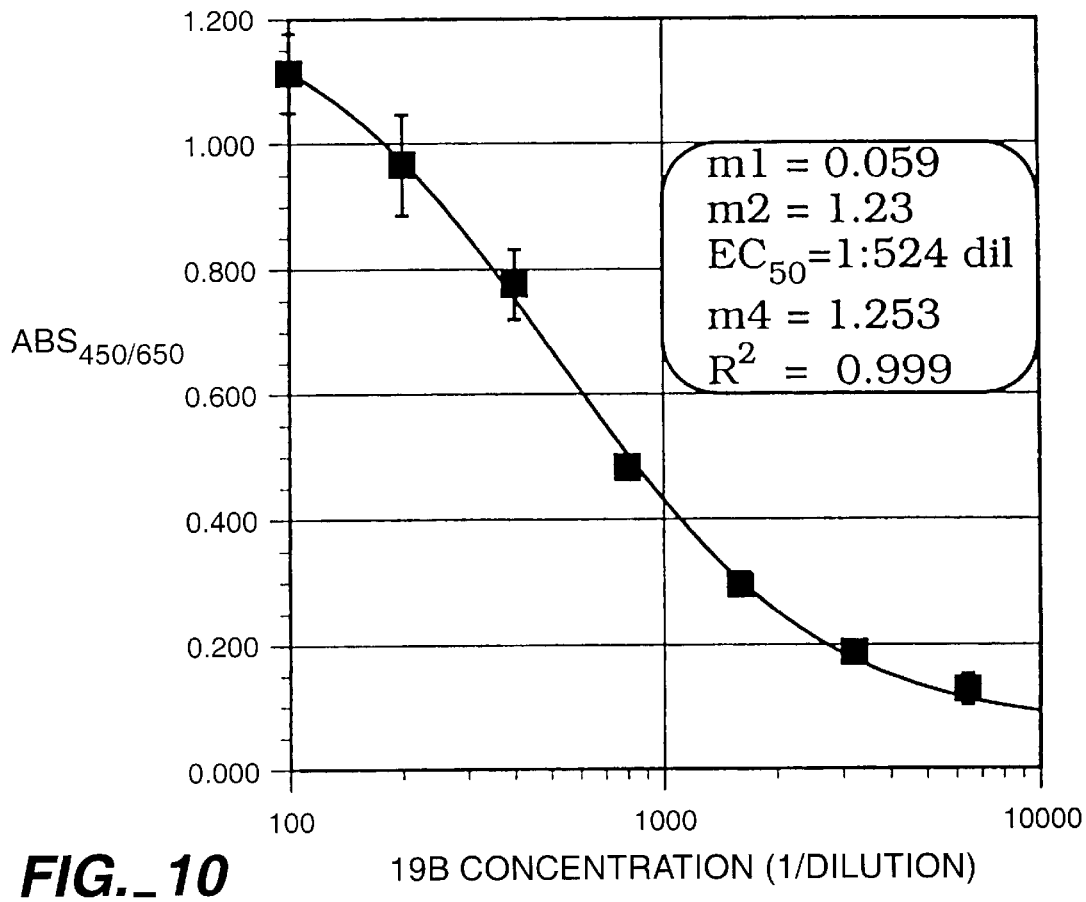
FIG._10
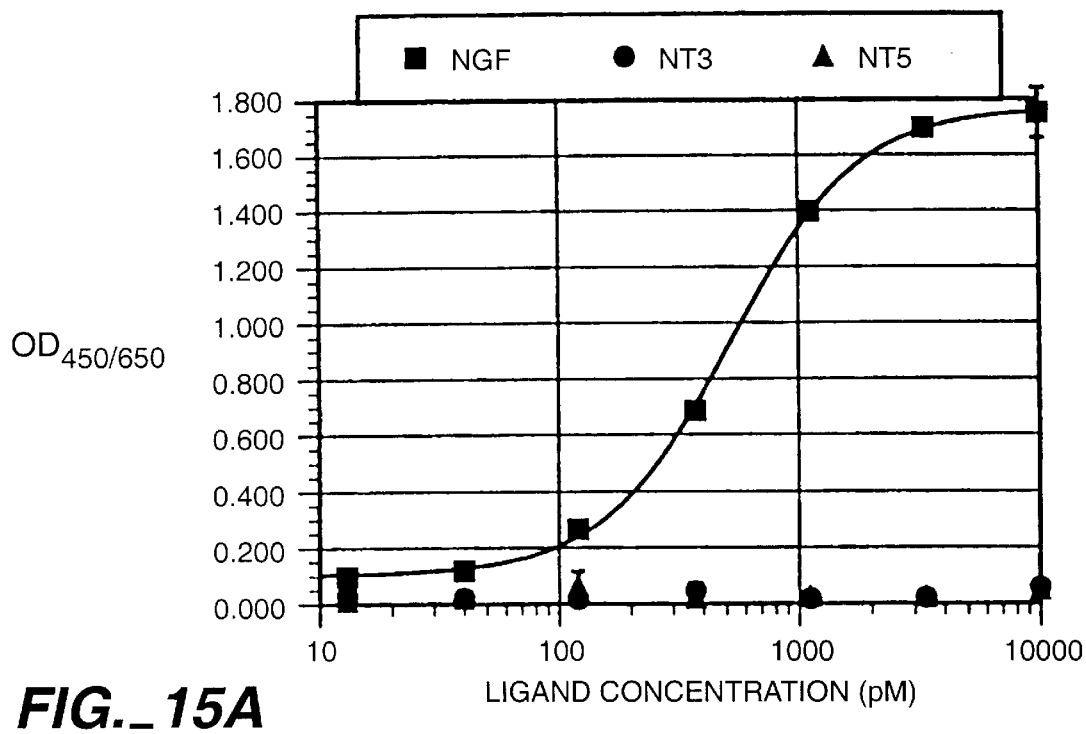
FIG._15A

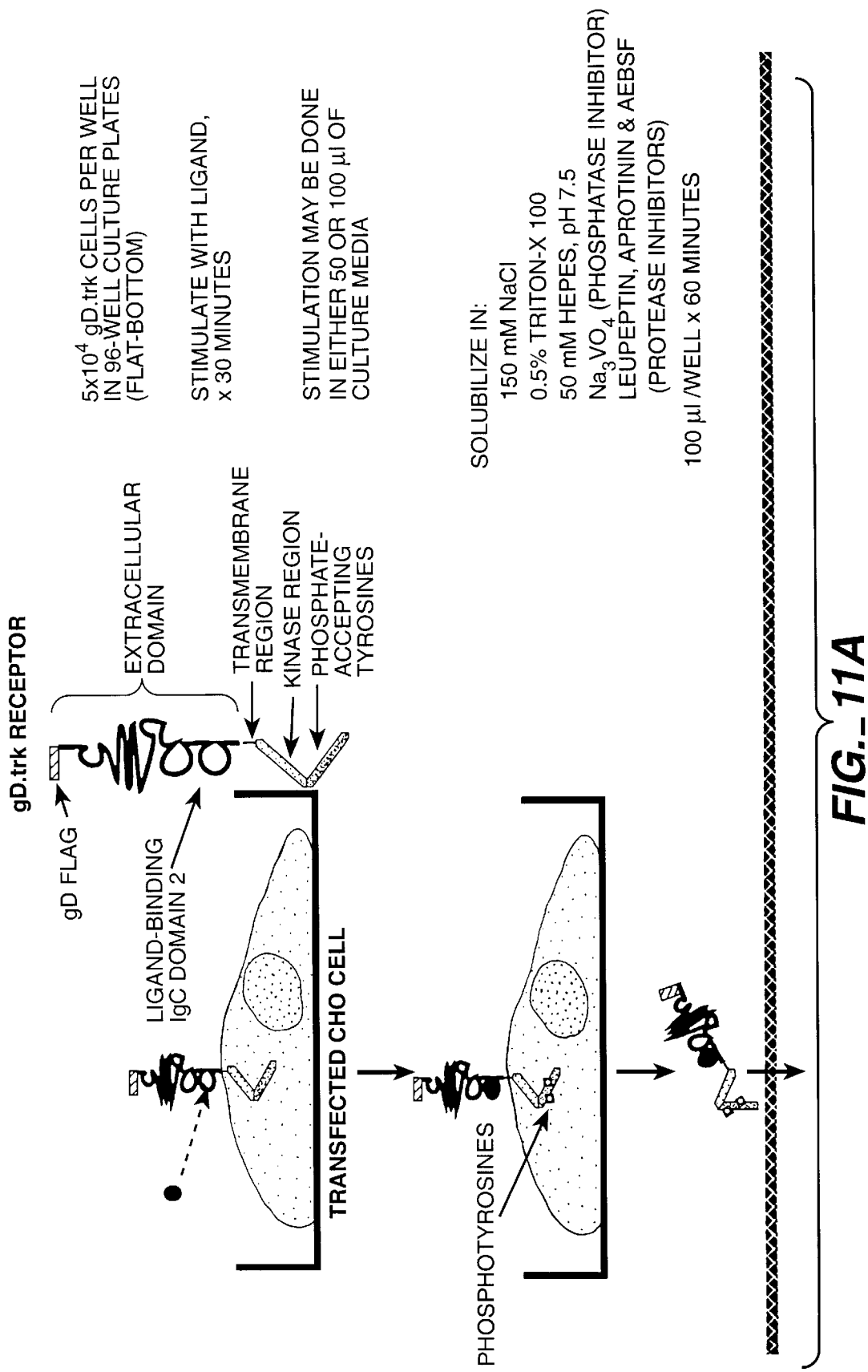
FIG._11A

```
                ^sp6 RNA start
 841  TATAGAATAA CATCCACTTT GCCTTTCTCT CCACTCCCAG GTCCAACTGC
      ATATCTTATT GTAGGTGAAA CGGAAAGAGA GGTGTCCACA CAGGTTGACG ^cloning linker
           ^R1 site mutated in
             ^begin gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGGGAGG ACTGGGGACC CTGTGACAAG CTTCAGGCGCG AACGACCAAC
      AGAGCAGTTA GAGGCGCTCC TGACCCCTGG GACACTGTTC GAAGTCGCGC TTGCTGGTTG ^Start gD
                                                          M* G* G*
   1  TACCCCGATC ATCAGTTATC CTTAAGGTCT CTTTTGTGTG GTGCGTTCCG GTATGGGGGG
      ATGGGGCTAG TAGTCAATAG GAATTCCAGA GAAAACACAC CACGCAAGGC CATACCCCCC T* A* A*   R* L* G*   A* V* I* L*  F* V* V*  I* V* G* L*  H* G* V*
   4  GACTGCCGCC AGGTTGGGGG CCGTGATTTT GTTTGTCGTC ATAGTGGGCC TCCATGGGT
      CTGACGGCGG TCCAACCCCC GGCACTAAAA CAAACAGCAG TATCACCCGG AGGTACCCCA R* G* K*  Y* A* L*  A  D  A  S  L  K  M  A  D  P  N  R  F  R
  24  CCGGGCAAA TATGCCTTGG CGGATGCCTC TCTCAAGATG GCCGACCCCA ATCGATTTCG
      GGCGCCGTTT ATACGGAACC GCCTACGGAG AGAGTTCTAC CGGCTGGGGT TAGCTAAAGC
```

*FIG._12A*

^Xho and GTA mutated in
^begin mature trkA

```
        G   K   D   L   P   V   L   D   Q   L   E   V   A   A   P   C   P   D   A
  44
1261    CGGCAAAGAC CTTCCGGTCC TGGACCAGCT GCTCGAGGTA GCCGCACCCT GCCCCGATGC
        GCCGTTTCTG GAAGGCCAGG ACCTGGTCGA CGAGCTCCAT CGGCGTGGGA CGGGGCTACG

C   C   P   H   G   S   S   G   L   R   C   T   R   D   G   A   L   D   S   L
  64
1321    CTGCTGCCCC CACGGCTCCT CGGGACTGCG ATGCACCCCG GATGGGGCCC TGGATAGCCT
        GACGACGGGG GTGCCGAGGA GCCCTGACGC TACGTGGGGC CTACCCCGGG ACCTATCGGA

H   H   L   P   G   A   E   N   L   T   E   L   Y   I   E   N   Q   Q   H   L
  84
1381    CCACCACCTG CCCGGCGCAG AGAACCTGAC TGAGCTCTAC ATCGAGAACC AGCAGCATCT
        GGTGGTGGAC GGGCCGCGTC TCTTGGACTG ACTCGAGATG TAGCTCTTGG TCGTCGTAGA

Q   H   L   E   L   R   D   L   R   G   L   G   E   L   R   N   L   T   I   V
 104
1441    GCAGCATCTG GAGCTCCGTG ATCTGAGGGG CCTGGGGGAG CTGAGAAACC TCACCATCGT
        CGTCGTAGAC CTCGAGGCAC TAGACTCCCC GGACCCCCTC GACTCTTTGG AGTGGTAGCA

K   S   G   L   R   F   V   A   P   D   A   F   H   F   T   P   R   L   S   R
 124
1501    GAAGAGTGGT CTCCGTTTCG TGGCGCCAGA TGCCTTCCAT TTCACTCCTC GGCTCAGTCG
        CTTCTCACCA GAGGCAAAGC ACCGCGGTCT ACGGAAGGTA AAGTGAGGAG CCGAGTCAGC

L   N   L   S   F   N   A   L   E   S   L   S   W   K   T   V   Q   G   L   S
 144
1561    CCTGAATCTC TCCTTCAACG CTCTGGAGTC CTCTCCTGG AAAACTGTGC AGGGCCTCTC
        GGACTTAGAG AGGAAGTTGC GAGACCTCAG GAGAGGACC TTTTGACACG TCCCGGAGAG

L   Q   E   L   V   L   S   G   N   P   L   H   C   S   C   A   L   R   W   L
 164
1621    CTTACAGGAA CTGGTCCTGT CGGGGAACCC TCTGCACTGT TCTTGTGCCC TGCGCTGGCT
        GAATGTCCTT GACCAGGACA GCCCCTTGGG AGACGTGACA AGAACACGGG ACGCGACCGA
```

FIG._12B

```
184   Q   R   W   E   E   E   G   L   G   G   V   P   E   Q   K   L   Q   C   H   G
1681  ACAGCGCTGG GAGGAGGAGG GACTGGGCGG AGTGCCTGAA CAGAAGCTGC AGTGTCATGG
      TGTCGCGACC CTCCTCCTCC CTGACCCGCC TCACGGACTT GTCTTCGACG TCACAGTACC

204   Q   G   P   L   A   H   M   P   N   A   S   C   G   V   P   T   L   K   V   Q
1741  GCAAGGGCCC CTGGCCCACA TGCCCAATGC CAGCTGTGGT GTGCCCACGC TGAAGGTCCA
      CGTTCCCGGG GACCGGGTGT ACGGGTTACG GTCGACACCA CACGGGTGCG ACTTCCAGGT

224   V   P   N   A   S   V   D   V   G   D   D   V   L   L   R   C   Q   V   E   G
1801  GGTGCCCAAT GCCTCGGTGG ATGTGGGGGA CGACGTGCTG CTGCGGTGCC AGGTGGAGGG
      CCACGGGTTA CGGAGCCACC TACACCCCCT GCTGCACGAC GACGCCACGG TCCACCTCCC

244   R   G   L   E   Q   A   G   W   I   L   T   E   L   E   Q   S   A   T   V   M
1861  GCGGGGCCTG GAGCAGGCCG GCTGGATCCT CACAGAGCTG GAGCAGTCAG CCACGGTGAT
      CGCCCCGGAC CTCGTCCGGC CGACCTAGGA GTGTCTCGAC CTCGTCAGTC GGTGCCACTA

264   K   S   G   G   L   P   S   L   G   L   T   L   A   N   V   T   S   D   L   N
1921  GAAATCTGGG GGTCTGCCAT CCCTGGGGCT GACCCTGGCC AATGTCACCA GTGACCTCAA
      CTTTAGACCC CCAGACGGTA GGGACCCCGA CTGGGACCGG TTACAGTGGT CACTGGAGTT

284   R   K   N   L   T   C   W   A   E   N   D   V   G   R   A   E   V   S   V   Q
1981  CAGGAAGAAC TTGACGTGCT GGGCAGAGAA CGATGTGGGC CGGGCAGAGG TCTCTGTTCA
      GTCCTTCTTG AACTGCACGA CCCGTCTCTT GCTACACCCG GCCCGTCTCC AGAGACAAGT

304   V   N   V   S   F   P   A   S   V   Q   L   H   T   A   V   E   M   H   H   W
2041  GGTCAACGTC TCCTTCCCGG CCAGTGTGCA GCTGCACACG GCGGTGGAGA TGCACCACTG
      CCAGTTGCAG AGGAAGGGCC GGTCACACGT CGACGTGTGC CGCCACCTCT ACGTGGTGAC
```

FIG.—12C

```
184   Q   R   W   E   E   G   L   G   G   V   P   E   Q   K   L   Q   C   H   G
1681  ACAGCGCTGG GAGGAGGAGG GACTGGGCGG AGTGCCTGAA CAGAAGCTGC AGTGTCATGG
      TGTCGCGACC CTCCTCCTCC CTGACCCGCC TCACGGACTT GTCTTCGACG TCACAGTACC

204   Q   G   P   L   A   H   M   P   N   A   S   C   G   V   P   T   L   K   V   Q
1741  GCAAGGGCCC CTGGCCCACA TGCCCAATGC CAGCTGTGGT GTGCCCACGC TGAAGGTCCA
      CGTTCCCGGG GACCGGGTGT ACGGGTTACG GTCGACACCA CACGGGTGCG ACTTCCAGGT

224   V   P   N   A   S   V   D   V   G   D   D   V   L   L   R   C   Q   V   E   G
1801  GGTGCCCAAT GCCTCGGTGG ATGTGGGGGA CGACGTGCTG CTGCGGTGCC AGGTGGAGGG
      CCACGGGTTA CGGAGCCACC TACACCCCCT GCTGCACGAC GACGCCACGG TCCACCTCCC

244   R   G   L   E   Q   A   G   W   I   L   T   E   L   E   Q   S   A   T   V   M
1861  GCGGGGCCTG GAGCAGGCCG GCTGGATCCT CACAGAGCTG GAGCAGTCAG CCACGGTGAT
      CGCCCCGGAC CTCGTCCGGC CGACCTAGGA GTGTCTCGAC CTCGTCAGTC GGTGCCACTA

264   K   S   G   G   L   P   S   L   G   L   A   N   V   T   S   D   L   N
1921  GAAATCTGGG GGTCTGCCAT CCCTGGGGCT GACCCTGGCC AATGTCACCA GTGACCTCAA
      CTTTAGACCC CCAGACGGTA GGGACCCCGA CTGGGACCGG TTACAGTGGT CACTGGAGTT

284   R   K   N   L   T   C   W   A   E   N   D   V   G   R   A   E   V   S   V   Q
1981  CAGGAAGAAC TTGACGTGCT GGGCAGAGAA CGATGTGGGC CGGGCAGAGG TCTCTGTTCA
      GTCCTTCTTG AACTGCACGA CCCGTCTCTT GCTACACCCG GCCCGTCTCC AGAGACAAGT

304   V   N   V   S   F   P   A   S   V   Q   L   H   T   A   V   E   M   H   H   W
2041  GGTCAACGTC TCCTTCCCGG CCAGTGTGCA GCTGCACACG GCGGTGGAGA TGCACCACTG
      CCAGTTGCAG AGGAAGGGCC GGTCACACGT CGACGTGTGC CGCCACCTCT ACGTGGTGAC
```

*FIG._12D*

```
464    N  K  F        G  I  N  R        P  A  V        L  A  P        E  D  G  L        A  M  S
2521   AAACAAGTTT     GGGATCAACC        GCCCGGCTGT     GCTGGCTCCA     GAGGATGGGC        TGGCCATGTC
       TTTGTTCAAA     CCCTAGTTGG        CGGGCCGACA     CGACCGAGGT     CTCCTACCCG        ACCGGTACAG

484    L  H  F        M  T  L  G        G  S  S        L  S  P        T  E  G  K        G  S  G
2581   CCTGCATTTC     ATGACATTGG        GTGGCAGCTC     CCTGTCCCCC     ACCGAGGGCA        AAGGCTCTGG
       GGACGTAAAG     TACTGTAACC        CACCGTCGAG     GGACAGGGGG     TGGCTCCCGT        TTCCGAGACC

504    L  Q  G        H  I  I  E        N  P  Q        Y  F  S        D  A  C  V        H  H  I
2641   GCTCCAAGGC     CACATCATCG        AGAACCCACA     ATACTTCAGT     GATGCCTGTG        TTCACCACAT
       CGAGGTTCCG     GTGTAGTAGC        TCTTGGGTGT     TATGAAGTCA     CTACGGACAC        AAGTGGTGTA

524    K  R  R        D  I  V  L        K  W  E        L  G  E        G  A  F  G        K  V  F
2701   CAAGCGCCGG     GACATCGTGC        TCAAGTGGGA     GCTGGGGGAG     GGCGCCTTTG        GAAGGTCTT
       GTTCGCGGCC     CTGTAGCACG        AGTTCACCCT     CGACCCCCTC     CCGCGGAAAC        CCTTCCAGAA

544    L  A  E        C  H  N  L        L  P  E        Q  D  K        M  L  V  A        V  K  A
2761   CCTTGCTGAG     TGCCACAACC        TCCTGCCTGA     GCAGGACAAG     ATGCTGGTGG        CTGTCAAGGC
       GGAACGACTC     ACGGTGTTGG        AGGACGGACT     CGTCCTGTTC     TACGACCACC        GACAGTTCCG

564    L  K  E        A  S  E  S        A  R  Q        D  F  Q        R  E  A  E        L  L  T
2821   ACTGAAGGAG     GCGTCCGAGA        GTGCTCGGCA     GGACTTCCAA     CGTGAGGCTG        AGCTGCTCAC
       TGACTTCCTC     CGCAGGCTCT        CACGAGCCGT     CCTGAAGGTT     GCACTCCGAC        TCGACGAGTG

584    M  L  Q        H  Q  H  I        V  R  F        F  G  V        C  T  E  G        R  P  L
2881   CATGCTGCAG     CACCAGCACA        TCGTGCGCTT     CTTCGGCGTC     TGCACCGAGG        GCCGCCCCCT
       GTACGACGTC     GTGGTCGTGT        AGCACGCGAA     GAAGCCGCAG     ACGTGGCTCC        CGGCGGGGGA
```

FIG._12E

```
604  L   M   V   F   E   Y   M   R   H   G   D   L   N   R   F   L   R   S   H   G
2941 GCTCATGGTC TTTGAGTATA TGCGGCACGG GGACCTCAAC CGCTTCCTCC GATCCCATGG
     CGAGTACCAG AAACTCATAT ACGCCGTGCC CCTGGAGTTG GCGAAGGAGG CTAGGGTACC

624  P   D   A   K   L   L   A   G   G   E   D   V   A   P   G   P   L   G
3001 ACCTGATGCC AAGCTGCTGG CTGGTGGGGA GGATGTGGCT CCAGGCCCCC TGGGTCTGGG
     TGGACTACGG TTCGACGACC GACCACCCCT CCTACACCGA GGTCCGGGGG ACCCAGACCC

644  Q   L   L   A   V   A   S   Q   V   A   A   G   M   V   Y   L   A   G   L   H
3061 GCAGCTGCTG GCCGTGGCTA GCCAGGTCGC TGCGGGGATG GTGTACCTGG CGGGTCTGCA
     CGTCGACGAC CGGCACCGAT CGGTCCAGCG ACGCCCCTAC CACATGGACC GCCCAGACGT

664  F   V   H   R   D   L   A   T   R   N   C   L   V   Y   S   T   D   Y   Y   R   V   V   K
3121 TTTTGTGCAC CGGGACCTGG CCACACGCAA CTGTCTAGTG CTACAGCACC GACTATTACC GTGTGGTCAA
     AAAACACGTG GCCCTGGACC GGTGTGCGTT GACAGATCAC GATGTCGTGG CTGATAATGG ACCACCAGTT

684  I   G   D   F   G   M   S   R   D   I   L   P   I   R   W   M   P   E   S   V   G   G
3181 GATTGGTGAT TTTGGCATGA GCAGGGATAT CTACAGCACC GATGTCGTGG CTGATAATGG
     CTAACCACTA AAACCGTACT CGTCCCTATA GATGTCGTGG CTACAGCACC GACTATTACC

704  R   T   M   L   P   I   R   W   M   P   E   S   I   L   Y   R   K   F   T
3241 CCGCACCATG CTGCCCCATTC GCTGGATGCC GCCCGAGAGC ATCCTGTACC GTAAGTTCAC
     GGCGTGGTAC GACGGGTAAG CGACCTACGG CGGGCTCTCG TAGGACATGG CATTCAAGTG

724  T   E   S   D   V   W   S   F   G   V   V   L   W   E   I   F   T   Y   G   K
3301 CACCGAGAGC GACGTGTGGA GCTTCGGCGT GGTGCTCTGG GAGATCTTCA CCTACGGCAA
     GTGGCTCTCG CTGCACACCT CGAAGCCGCA CCACGAGACC CTCTAGAAGT GGATGCCGTT

```
3361 GCAGCCCTGG TACCAGCTCT CCAACACGGA GGCAATCGAC TGCATCACGC AGGGACGTGA
     CGTCGGGACC ATGGTCGAGA GGTTGTGCCT CCGTTAGCTG ACGTAGTGCG TCCCTGCACT

764   L   E   R   P   R   A   C   P   P   E   V   Y   A   I   M   R   G   C   W   Q
3421 GTTGGAGCGG CCACGTGCCT GCCCACCAGA GGTCTACGCC ATCATGCGGG GCTGCTGGCA
     CAACCTCGCC GGTGCACGGA CGGGTGGTCT CCAGATGCGG TAGTACGCCC CGACGACCGT

784   R   E   P   Q   Q   R   H   S   I   K   D   V   H   A   R   L   Q   A   L   A
3481 GCGGGAGCCC CAGCAACGCC ACAGCATCAA GGATGTGCAC GCCCGGCTGC AAGCCCTGGC
     CGCCCTCGGG GTCGTTGCGG TGTCGTAGTT CCTACACGTG CGGGCCGACG TTCGGGACCG

R1 site added with cloning primer^
                    R1 site removed with cut and fill^
804   Q   A   P   P   V   Y   L   D   V   L   G   Q
3541 CCAGGCACCT CCTGTCTACC TGGATGTCCT GGGCTAGAAT TAATTCAATC GATGGCCGCC
     GGTCCGTGGA GGACAGATGG ACCTACAGGA CCCGATCTTA ATTAAGTTAG CTACCGGCGG ^sv40 early poly A
3601 ATGGCCCAAC TTGTTTATTG CAGCTTATAA TGGTTACAAA TAAAGCAATA GCATCACAAA
     TACCGGGTTG AACAAATAAC GTCGAATATT ACCAATGTTT ATTTCGTTAT CGTAGTGTTT
```

FIG.—12G

```
                                              ^sp6 RNA start
     841  TATAGAATAA CATCCACTTT GCCTTTCTCT CCACAGGTGT CCACTCCCAG GTCCAACTGC
          ATATCTTATT GTAGGTGAAA CGGAAAGAGA GGTGTCCACA GGTGAGGGTC CAGGTTGACG ^cloning linker    ^begin gD from pchadII
     901  ACCTCGGTTC TATGATTGA ATTCCACTGC CTTCCACCAA GCTCTGCAGG ATCCCAGAGT
          TGGAGCCAAG ATAGCTAACT TAAGGTGACG GAAGGTGGTT CGAGACGTCC TAGGGTCTCA 961  CAGGGGTCTG TATCTTCCTG CTGGTGGCTC CAGTTCAGGA ACAGTAAACC CTGCTCCGAA
          GTCCCCAGAC ATAGAAGGAC GACCACCGAG GTCAAGTCCT TGTCATTTGG GACGAGGCTT 1021  TATTGCCTCT CACATCTCGT CAATCTCCGC GAGGACTGGG GACCCTGTGA CAAGCTTCAG
          ATAACGGAGA GTGTAGAGCA GTTAGAGGCG CTCCTGACCC CTGGGACACT GTTCGAAGTC 1081  CGGGAACGAC CAACTACCCC GATCATCAGT TATCCTTAAG GTCTCTTTTG TGTGGTGCGT
          GCGCTTGCTG GTTGATGGGG CTAGTAGTCA ATAGGAATTC CAGAGAAAAC ACACCACGCA ^Start gD
       1    M* G* G* T* A*  A* R* L*  G* A* V* I*  L* F* V*  V* I* V*
    1141  TCCGGTATGG GGGGACTGC CGCCAGGTTG GGGGCCGTGA TTTTGTTTGT CGTCATAGTG
          AGGCCATACC CCCCCTGACG GCGGTCCAAC CCCCGGCACT AAAACAAACA GCAGTATCAC 19   G* L* H* G*  V* R* G*  K* Y* A*   L* A  D  A  S  L  K  M  A  D
    1201  GGCCTCCATG GGGTCCGCGG CAAATATGCC TTGGCGGATG CCTCTCTCAA GATGGCCGAC
          CCGGAGGTAC CCCAGGCGCC GTTTATACGG AACCGCCTAC GGAGAGAGTT CTACCGGCTG
```

FIG._13A

```
                                xho and GTA mutated in^
                                                   start mature trkB^
  39  P   N   R   F   R   G   K   D   L   P   V   L   D   Q   L   L   E   V   C   P
1261  CCCAATCGAT TTCGCGGCAA AGACCTTCCG GTCCTGGACC AGCTGCTCGA GGTATGTCCC
      GGGTTAGCTA AAGCGCCGTT TCTGGAAGGC CAGGACCTGG TCGACGAGCT CCATACAGGG 59  T   S   C   K   C   S   A   S   R   I   W   C   S   D   P   S   P   G   I   V
1321  ACGTCCTGCA AATGCAGTGC CTCTCGGATC TGGTGCAGCG ACCCTTCTCC TGGCATCGTG
      TGCAGGACGT TTACGTCACG GAGAGCCTAG ACCACGTCGC TGGGAAGAGG ACCGTAGCAC 79  A   F   P   R   L   E   P   N   S   V   D   P   E   N   I   T   E   I   F   I
1381  GCATTTCCGA GATTGGAGCC TAACAGTGTA GATCCTGAGA ACATCACCGA AATTTTCATC
      CGTAAAGGCT CTAACCTCGG ATTGTCACAT CTAGGACTCT TGTAGTGGCT TTAAAAGTAG 99  A   N   Q   K   R   L   E   I   I   N   E   D   D   V   E   A   Y   V   G   L
1441  GCAAACCAGA AAAGGTTAGA AATCATCAAC GAAGATGATG TTGAAGCTTA TGTGGGACTG
      CGTTTGGTCT TTTCCAATCT TTAGTAGTTG CTTCTACTAC AACTTCGAAT ACACCCTGAC 119  R   N   L   T   I   V   D   S   G   L   K   F   V   A   H   K   A   F   L   K
1501  AGAAATCTGA CAATTGTGGA TTCTGGATTA AAATTTGTGG CTCATAAAGC ATTTCTGAAA
      TCTTTAGACT GTTAACACCT AAGACCTAAT TTTAAACACC GAGTATTTCG TAAAGACTTT 139  N   S   N   L   Q   H   I   N   F   T   R   N   K   L   T   S   L   S   R   K
1561  AACAGCAACC TGCAGCACAT CAATTTTACC CGAAACAAAC TGACGAGTTT GTCTAGGAAA
      TTGTCGTTGG ACGTCGTGTA GTTAAAATGG GCTTTGTTTG ACTGCTCAAA CAGATCCTTT 159  H   F   R   H   L   D   L   S   E   L   I   L   V   G   N   P   F   T   C   S
1621  CATTTCCGTC ACCTTGACTT GTCTGAACTG ATCCTGGTGG GCAATCCATT TACATGCTCC
      GTAAAGGCAG TGGAACTGAA CAGACTTGAC TAGGACCACC CGTTAGGTAA ATGTACGAGG
```

FIG._13B

```
179  C    D    I    M    W    I    K    T    L    Q    E    A    K    S    S    P    D    T    Q    D
1681 TGTGACATTA TGTGGATCAA ACACCTAGTT GACTCTCCAA GAGGCTAAAT CCAGTCCAGA CACTCAGGAT
     ACACTGTAAT ACACCTAGTT CTGAGAGGTT CTCCGATTTA GGTCAGGTCT GTGAGTCCTA

199  L    Y    C    L    N    E    S    S    K    N    I    P    L    A    N    L    Q    I    P    N
1741 TTGTACTGCC TGAATGAAAG CAGCAAGAAT ATTCCCCTGG CAAACCTGCA GATACCCAAT
     AACATGACGG ACTTACTTTC GTCGTTCTTA TAAGGGGACC GTTTGGACGT CTATGGGTTA

219  C    G    L    P    S    A    N    L    A    A    P    N    L    T    V    E    E    G    K    S
1801 TGTGGTTTGC CATCTGCAAA TCTGGCCGCA CCTAACCTCA CTGTGGAGGA AGGAAAGTCT
     ACACCAAACG GTAGACGTTT AGACCGGCGT GGATTGGAGT GACACCTCCT TCCTTTCAGA

239  I    T    L    S    C    S    V    A    G    D    P    V    P    N    M    Y    W    D    V    G
1861 ATCACATTAT CCTGTAGTGT GGCAGGTGAT CCGGTTCCTA ATATGTATTG GGATGTTGGT
     TAGTGTAATA GGACATCACA CCGTCCACTA GGCCAAGGAT TATACATAAC CCTACAACCA

259  N    L    V    S    K    H    M    N    E    T    S    H    T    Q    G    S    L    R    I    T
1921 AACCTGGTTT CCAAACATAT GAATGAAACA AGCCACACAC AGGGCTCCTT AAGGATAACT
     TTGGACCAAA GGTTTGTATA CTTACTTTGT TCGGTGTGTG TCCCGAGGAA TTCCTATTGA

279  N    I    S    S    D    D    S    G    K    Q    I    S    C    V    A    E    N    L    V    G
1981 AACATTTCAT CCGATGACAG TGGGAAGCAG ATCTCTTGTG TGGCGGAAAA TCTTGTAGGA
     TTGTAAAGTA GGCTACTGTC ACCCTTCGTC TAGAGAACAC ACCGCCTTTT AGAACATCCT

299  E    D    Q    D    S    V    N    L    T    V    H    F    A    P    T    I    T    F    L    E
2041 GAAGATCAAG ATTCTGTCAA CCTCACTGTG CATTTTGCAC CAACTATCAC ATTTCTCGAA
     CTTCTAGTTC TAAGACAGTT GGAGTGACAC GTAAAACGTG GTTGATAGTG TAAAGAGCTT
```

FIG._13C

```
319  S   P   T   S   D   H   H   W   C   I   P   F   T   V   K   G   N   P   K   P
2101 TCTCCAACCT CAGACCACCA CTGGTGCATT CCATTCACTG TGAAAGGCAA CCCAAAACCA
     AGAGGTTGGA GTCTGGTGGT GACCACGTAA GGTAAGTGAC ACTTTCCGTT GGGTTTTGGT

339  A   L   Q   W   F   Y   N   G   A   I   L   N   E   S   K   Y   I   C   T   K
2161 GCGCTTCAGT GGTTCTATAA CGGGGCAATA TTGAATGAGT CCAAATACAT CTGTACTAAA
     CGCGAAGTCA CCAAGATATT GCCCCGTTAT AACTTACTCA GGTTTATGTA GACATGATTT

359  I   H   V   T   N   H   T   E   Y   H   G   C   L   Q   L   D   N   P   T   H
2221 ATACATGTTA CCAATCACAC GGAGTACCAC GGCTGCCTCC AGCTGGATAA TCCCACTCAC
     TATGTACAAT GGTTAGTGTG CCTCATGGTG CCGACGGAGG TCGACCTATT AGGGTGAGTG

379  M   N   N   G   D   Y   T   L   I   A   K   N   E   Y   G   K   D   E   K   Q
2281 ATGAACAATG GGGACTACAC TCTAATAGCC AAGAATGAGT ATGGGAAGGA TGAGAAACAG
     TACTTGTTAC CCCTGATGTG AGATTATCGG TTCTTACTCA TACCCTTCCT ACTCTTTGTC

399  I   S   A   H   F   M   G   W   P   G   I   D   D   G   A   N   P   N   Y   P
2341 ATTTCTGCTC ACTTCATGGG CTGGCCTGGA ATTGACGATG GTGCAAACCC AAATTATCCT
     TAAAGACGAG TGAAGTACCC GACCGGACCT TAACTGCTAC CACGTTTGGG TTTAATAGGA

419  D   V   I   Y   E   D   Y   G   T   A   A   N   D   I   G   D   T   N   R
2401 GATGTAATTT ATGAAGATTA TGGAACTGCA GCGAATGACA TCGGGGACAC CACGAACAGA
     CTACATTAAA TACTTCTAAT ACCTTGACGT CGCTTACTGT AGCCCCTGTG GTGCTTGTCT

439  S   N   E   I   P   S   T   D   V   T   D   K   T   G   R   E   H   L   S   V
2461 AGTAATGAAA TCCCCTTCCAC AGACGTCACT GATAAAACCG GTCGGGAACA TCTCTCGGTC
     TCATTACTTT AGGGAAGGTG TCTGCAGTGA CTATTTTGGC CAGCCCTTGT AGAGAGCCAG

459  Y   A   V   V   I   A   S   V   V   G   F   C   L   L   V   M   L   F   L
2521 TATGCTGTGG TGGTGATTGC GTCTGTGGTG GGATTTTGCC TTTTGGTAAT GCTGTTTCTG
     ATACGACACC ACCACTAACG CAGACACCAC CCTAAAACGG AAAACCATTA CGACAAAGAC
```

FIG._13D

```
479  L   K   L   A       R   H   S       K   F   G       M   K   G   P       A   S   V       I   S   N
2581 CTTAAGTTGG CAAGACACTC AAGTTTGGC ATGAAAGGCC CAGCCTTCCGT TATCAGCAAT
     GAATTCAACC GTTCTGTGAG GTTCAAACCG TACTTTCCGG GTCGGAGGCA ATAGTCGTTA

499  D   D   D   S       A   S   P       L   H   H       I   S   N   G       S   N   T       P   S   S
2641 GATGATGACT CTGCCAGCCC ACTCCATCAC ATCTCCAATG GGAGTAACAC TCCATCTTCT
     CTACTACTGA GACGGTCGGG TGAGGTAGTG TAGAGGTTAC CCTCATTGTG AGGTAGAAGA

519  S   E   G   G       P   D   A       V   I   I       G   M   T   K       I   P   V       I   E   N
2701 TCGGAAGGTG GCCCAGATGC TGTCATTATT GGAATGACCA AGATCCCTGT CATTGAAAAT
     AGCCTTCCAC CGGGTCTACG ACAGTAATAA CCTTACTGGT TCTAGGGACA GTAACTTTTA

539  P   Q   Y   F       G   I   T       N   S   Q       L   K   P   D       T   F   V       Q   H   I
2761 CCCCAGTACT TTGGCATCAC CAACAGTCAG CTCAAGCCAG ACACATTTGT TCAGCACATC
     GGGGTCATGA AACCGTAGTG GTTGTCAGTC GAGTTCGGTC TGTGTAAACA AGTCGTGTAG

559  K   R   H   N       I   V   L       K   R   E       L   G   E   G       A   F   G       K   V   F
2821 AAGCGACATA ACATTGTTCT GAAAAGGGAG CTAGGCGAAG GAGCCTTTGG AAAAGTGTTC
     TTCGCTGTAT TGTAACAAGA CTTTTCCCTC GATCCGCTTC CTCGGAAACC TTTTCACAAG

579  L   A   E   C       Y   N   L       C   P   E       Q   D   K   I       L   V   A       V   K   T
2881 CTAGCTGAAT GCTATAACCT CTGTCCTGAG CAGGACAAGA TCTTGGTGGC AGTGAAGACC
     GATCGACTTA CGATATTGGA GACAGGACTC GTCCTGTTCT AGAACCACCG TCACTTCTGG

599  L   K   D   A       S   D   N       A   R   K       D   F   H   R       E   A   E       L   L   T
2941 CTGAAGGATG CCAGTGACAA TGCACGCAAG GACTTCCACC GTGAGGCCGA GCTCCTGACC
     GACTTCCTAC GGTCACTGTT ACGTGCGTTC CTGAAGGTGG CACTCCGGCT CGAGGACTGG
```

*FIG._13E*

```
619  N          L          Q          H          E          H          I          V          K          F          Y          G          V          C          V          E          G          D          P          L
3001 AACCTCCAGC ATGAGCACAT CGTCAAGTTC TATGGCGTCT GCGTGGAGGG CGACCCCCTC
     TTGGAGGTCG TACTCGTGTA GCAGTTCAAG ATACCGCAGA CGCACCTCCC GCTGGGGGAG

639  I          M          V          F          E          Y          M          K          H          G          D          L          N          K          F          L          R          A          H          G
3061 ATCATGGTCT TTGAGTACAT GAAGCATGGG GACCTCAACA AGTTCCTCAG GGCACACGGC
     TAGTACCAGA AACTCATGTA CTTCGTACCC CTGGAGTTGT TCAAGGAGTC CCGTGTGCCG

659  P          D          A          V          L          M          A          E          G          N          P          P          T          E          L          T          Q          S          Q          M
3121 CCTGATGCCG TGCTGATGGC TGAGGGCAAC CCGCCCACGG AACTGACGCA GTCGCAGATG
     GGACTACGGC ACGACTACCG ACTCCCGTTG GGCGGGTGCC TTGACTGCGT CAGCGTCTAC

679  L          H          I          A          Q          Q          I          A          A          G          M          V          Y          L          A          S          Q          H          F          V
3181 CTGCATATAG CCCAGCAGAT CGCCGCGGGC ATGGTCTACC TGGCGTCCCA GCACTTCGTG
     GACGTATATC GGGTCGTCTA GCGGCGCCCG TACCAGATGG ACCGCAGGGT CGTGAAGCAC

699  H          R          D          L          A          T          R          N          C          L          V          G          E          N          L          L          V          K          I          G
3241 CACCGCGATT TGGCCACCAG GAACTGCCTG GTCGGGGAGA ACTTGCTGGT GAAAATCGGG
     GTGGCGCTAA ACCGGTGGTC CTTGACGGAC CAGCCCCTCT TGAACGACCA CTTTTAGCCC

719  D          F          G          M          S          R          D          V          Y          S          T          D          Y          Y          R          V          G          G          H          T
3301 GACTTTGGAA TGTCCCGGGA CGTGTACAGC ACTGACTACT ACAGGGTCGG TGGCCACACA
     CTGAAACCTT ACAGGGCCCT GCACATGTCG TGACTGATGA TGTCCCAGCC ACCGGTGTGT

739  M          L          P          I          R          W          M          P          P          E          S          I          M          Y          R          K          F          T          T          E
3361 ATGCTGCCCA TTCGCTGGAT GCCTCCAGAG AGCATCATGT ACAGGAAATT CACGACGGAA
     TACGACGGGT AAGCGACCTA CGGAGGTCTC TCGTAGTACA TGTCCTTTAA GTGCTGCCTT

759  S          D          V          W          S          L          G          V          V          L          W          E          I          F          T          Y          G          K          Q          P
3421 AGCGACGTCT GGAGCCTGGG GGTCGTGTTG TGGGAGATTT TCACCTATGG CAAACAGCCC
```

*FIG.—13F*

```
                    TCGCTGCAGA CCTCGGACCC CCAGCACAAC ACCCTCTAAA AGTGGATACC GTTGTGTCGGG
779       W    Y    Q    L      S    N    N      E    V    I      E    C    I    T      Q    G    R      V    L    Q
3481      TGGTACCAGC TGTCAAACAA TGAGGTGATA GAGTGTATCA CTCAGGGCCG AGTCCTGCAG
          ACCATGGTCG ACAGTTTGTT ACTCCACTAT CTCACATAGT GAGTCCCGGC TCAGGACGTC

799       R    P    R    T      C    P    Q      E    V    Y      E    L    M    L      G    C    W      Q    R    E
3541      CGACCCCCGA CGTGCCCCCA GGAGGTGTAT GAGCTGATGC TGGGGTGCTG GCAGCGAGAG
          GCTGGGGGCT GCACGGGGGT CCTCCACATA CTCGACTACG ACCCCACGAC CGTCGCTCTC

819       P    H    M    R      K    N    I      H    T    L    L      Q    N    L      A    K    A
3601      CCCCACATGA GGAAGAACAT CATACCCCTC TTCAGAACTT GGCCAAGGCA
          GGGGTGTACT CCTTCTTGTA GTATGGGGAG AAGTCTTGAA CCGGTTCCGT

839       S    P    V    Y      L    D    I      L    G    O
3661      TCTCCGGTCT ACCTGGACAT TCTAGGCTAG GGCCCTTTTC CCCAGACCGA TCCTTCCCAA
          AGAGGCCAGA TGGACCTGTA AGATCCGATC CCGGGAAAAG GGGTCTGGCT AGGAAGGGTT half Xho half Sal site from subcloning^
3721      CGTACTCCTC AGACGGGCTG AGAGGATGAA CATCTTTTAA CTGCCGCTGG AGGCCACCAA
          GCATGAGGAG TCTGCCCGAC TCTCCTACTT GTAGAAAATT GACGGCGACC TCCGGTGGTT 3781      GCTGCTCTCC TTCACTCTGA CAGTATTAAC ATCAAAGACT CCGAGAAGCT CTCGACCTGC
          CGACGAGAGG AAGTGAGACT GTCATAATTG TAGTTTCTGA GGCTCTTCGA GAGCTGGACG ^sv40 early poly A
3841      AGAAGCTTGG CCGCCATGGC CCAACTTGTT TATTGCAGCT TATAATGGTT ACAAATAAAG
          TCTTCGAACC GGCGGTACCG GGTTGAACAA ATAACGTCGA ATATTACCAA TGTTTATTTC
```

FIG._13G

```
                    ^sp6 RNA start
 841 TATAGAATAA CATCCACTTT GCCTTTCTCT CCACAGGTGT GCCTTTCTCT CCACTCCCAG GTCCAACTGC
     ATATCTTATT GTAGGTGAAA CGGAAAGAGA GGTGTCCACA GGTGAGGGTC CAGGTTGACG ^cloning linker
              ^RI site mutated in
                 ^gD from pchadII
 901 ACCTGAATTC CACTGCCTTC CACCAAGCTC CAGAGTCAGG CAGAGTCAGG GGTCTGTATC
     TGGACTTAAG GTGACGGAAG GTGGTTCGAG GTCTCAGTCC GTCTCAGTCC CCAGACATAG 961 TTCCTGCTGG TGGCTCCAGT TCAGGAACAG TAAACCCTGC TCCGAATATT GCCTCTCACA
     AAGGACGACC ACCGAGGTCA AGTCCTTGTC ATTTGGGACG AGGCTTATAA CGGAGAGTGT 1021 TCTCGTCAAT CTCCGCGAGG ACTGGGGACC CTGTGACAAG CTTCAGCGCG AACGACCAAC
     AGAGCAGTTA GAGGCGCTCC TGACCCCTGG GACACTGTTC GAAGTCGCGC TTGCTGGTTG ^Start
                                                           M* G* G*
1081 TACCCCGATC ATCAGTTATC CTTAAGGTCT CTTTTGTGTG GTGCCGTTCCG GTATGGGGGG
     ATGGGGCTAG TAGTCAATAG GAATTCCAGA GAAAACACAC CACGCAAGGC CATACCCCCC gD     T* A* A*    R* L* G* A*    V* I* L*    F* V* V*    I* V* G* L*    H* G* V*
  1  
1141 GACTGCCGCC AGGTGGGGG CCGTGATTTT GTTTGTCGTC ATAGTGGGCC TCCATGGGGT
     CTGACGGCGG TCCACCCCC GGCACTAAAA CAAACAGCAG TATCACCCGG AGTACCCCA R* G* K*    Y* A* L* A    D  A  S    L  K  M    A  D  P  N    R  F  R
 24  
1201 CCGGCGCAAA TATGCCTTGG CGGATGCCTC TCTCAAGATG GCCGACCCCA ATCGATTTCG
     GGCGCCGTTT ATACGGAACC GCCTACGGAG AGAGTTCTAC CGGCTGGGGT TAGCTAAAGC
```

*FIG.—14A*

```
                                                     ^Xho site and GTA mutated in
                                                     ^begin mature trkC
                                                      C  P  A  N   C  V  C
     G  K  D   L  P  V  L   D  Q  L   E  V
44
1261 CGGCAAAGAC CTTCCGGTCC TGGACCAGCT GCTCGAGGTA TGCCCTGCAA ATTGTGTCTG
     GCCGTTTCTG GAAGGCCAGG ACCTGGTCGA CGAGCTCCAT ACGGGACGTT TAACACAGAC S  K  T    E  I  N  C    R  R  P    D  D  G    N  L  F  P    L  L  E
64
1321 CAGCAAGACT GAGATCAATT GCCGGCGGCC GGACGATGGG AACCTCTTCC CCCTCCTGGA
     GTCGTTCTGA CTCTAGTTAA CGGCCGCCGG CCTGCTACCC TTGGAGAAGG GGGAGGACCT G  Q  D    S  G  N  S    N  G  N    A  N  I    N  I  T  D    I  S  R
84
1381 AGGGCAGGAT TCAGGGAACA GCAATGGGAA CGCCAATATC AACATCACGG ACATCTCAAG
     TCCCGTCCTA AGTCCCTTGT CGTTACCCTT GCGGTTATAG TTGTAGTGCC TGTAGAGTTC N  I  T    S  I  H  I    E  N  W    R  S  L    H  T  L  N    A  V  D
104
1441 GAATATCACT TCCATACACA TAGAGAACTG GCGCAGTCTT CACACGCTCA ACGCCGTGGA
     CTTATAGTGA AGGTATGTGT ATCTCTTGAC CGCGTCAGAA GTGTGCGAGT TGCGGCACCT M  E  L    Y  T  G  L    Q  K  L    T  I  K    N  S  G  L    R  S  I
124
1501 CATGGAGCTC TACACCGGAC TTCAAAAGCT GACCATCAAG AACTCAGGAC TTCGGAGCAT
     GTACCTCGAG ATGTGGCCTG AAGTTTTCGA CTGGTAGTTC TTGAGTCCTG AAGCCTCGTA Q  P  R    A  F  A  K    N  P  H    L  R  Y    I  N  L  S    N  R
144
1561 TCAGCCCAGA GCCTTTGCCA AGAACCCCCA CTTGCGTTAT ATAAACCTGT CAAGTAACCG
     AGTCGGGTCT CGGAAACGGT TCTTGGGGGT GAACGCAATA TATTTGGACA GTTCATTGGC L  T  T    L  S  W  Q    L  F  Q    T  L  S    L  R  E  L    Q  L  E
164
1621 GCTCACCACA CTCTCGTGGC AGCTCTTCCA GACGCTGAGT CTTCGGGAAT TGCAGTTGGA
```

FIG._14B

```
                CGAGTGGTGT GAGAGCACCG TCGAGAAGGT CTGCGACTCA GAAGCCCTTA AGTCAACCT

Q   N   F    F   N   C   S    C   D   I    R   W   M    Q   L   W   Q    E   Q   G
184
1681  GCAGAACTTT TTCAACTGCA GCTGTGACAT CCGCTGGATG CAGCTCTGGC AGGAGCAGGG
      CGTCTTGAAA AAGTTGACGT CGACACTGTA GGCGACCTAC GTCGAGACCG TCCTCGTCCC

E   A   K    L   N   S   Q    N   L   Y    C   I   N    A   D   G   S    Q   L   P
204
1741  GGAGGCCAAG CTCAACAGCC AGAACCTCTA CTGCATCAAT GCTGATGGCT CCCAGCTTCC
      CCTCCGGTTC GAGTTGTCGG TCTTGGAGAT GACGTAGTTA CGACTACCGA GGGTCGAAGG

L   F   R    M   N   I   S    Q   C   D    L   P   E    I   S   V   S    H   V   N
224
1801  TCTCTTCCGC ATGAACATCA GTCAGTGTGA CCTTCCTGAG ATCAGCGTGA GCCACGTCAA
      AGAGAAGGCG TACTTGTAGT CAGTCACACT GGAAGGACTC TAGTCGCACT CGGTGCAGTT

L   T   V    R   E   G   D    N   A   V    I   T   C    N   G   S   G    S   P   L
244
1861  CCTGACCGTA CGAGAGGGTG ACAATGCTGT TATCACTTGC AATGGCTCTG GATCACCCCT
      GGACTGGCAT GCTCTCCCAC TGTTACGACA ATAGTGAACG TTACCGAGAC CTAGTGGGGA

P   D   V    D   W   I   V    T   G   L    Q   S   I    N   T   H   Q    T   N   L
264
1921  TCCTGATGTG GACTGGATAG TCACTGGGCT GCAGTCCATC AACACTCACC AGACCAATCT
      AGGACTACAC CTGACCTATC AGTGACCCGA CGTCAGGTAG TTGTGAGTGG TCTGGTTAGA

N   W   T    N   V   H   A    I   N   L    T   L   V    N   V   T   S    E   D   N
284
1981  GAACTGGACC AATGTTCATG CCATCAACTT GACGCTGGTG AATGTGACGA GTGAGGACAA
      CTTGACCTGG TTACAAGTAC GGTAGTTGAA CTGCGACCAC TTACACTGCT CACTCCTGTT

G   F   T    L   T   C   I    A   E   N    V   V   G    M   S   N   A    S   V   A
304
2041  TGGCTTCACC CTGACGTGCA TTGCAGAGAA CGTGGTGGGC ATGAGCAATG CCAGTGTTGC
      ACCGAAGTGG GACTGCACGT AACGTCTCTT GCACCACCCG TACTCGTTAC GGTCACAACG
```

FIG._14C

```
324   L   T   V   Y   Y   P   P   R   V   V   S   L   E   E   P   E   L   R   L   E
2101  CCTCACTGTC TACTATCCCC CACGTGTGGT GAGCCTGGAG AGCCTGGAGC TGCGCCTGGA
      GGAGTGACAG ATGATAGGGG GTGCACACCA CTCGGACCTC CTCGGACCTC ACGCGGACCT

344   H   C   I   E   F   V   V   R   G   N   P   P   P   T   L   H   W   L   H   N
2161  GCACTGCATC GAGTTTGTGG TGCGTGGCAA CCCCCCACCA ACGCTGCACT GGCTGCACAA
      CGTGACGTAG CTCAAACACC ACGCACCGTT GGGGGGTGGT TGCGACGTGA CCGACGTGTT

364   G   Q   P   L   R   E   S   K   I   I   H   V   E   Y   Y   Q   E   G   E   I
2221  TGGGCAGCCT CTGCGGGAGT CCAAGATCAT CCATGTGGAA TACTACCAAG AGGGAGAGAT
      ACCCGTCGGA GACGCCCTCA GGTTCTAGTA GGTACACCTT ATGATGGTTC TCCCTCTCTA

384   S   E   G   C   L   L   F   N   K   P   T   H   Y   N   N   G   N   Y   T   L
2281  TTCCGAGGGC TGCCTGCTCT TCAACAAGCC CACCCACTAC AACAATGGCA ACTATACCCT
      AAGGCTCCCG ACGGACGAGA AGTTGTTCGG GTGGGTGATG TTGTTACCGT TGATATGGGA

404   I   A   K   N   P   L   G   T   A   N   Q   T   I   N   G   H   F   L   K   E
2341  CATTGCCAAA AACCCACTGG GCACAGCCAA CCAGACCATC AATGGCCACT TCCTCAAGGA
      GTAACGGTTT TTGGGTGACC CGTGTCGGTT GGTCTGGTAG TTACCGGTGA AGGAGTTCCT
                 ^begin ecd insert                                   ^end ecd insert 424   P   F   P   E   S   T   D   N   F   I   L   F   D   E   V   S   P   T   P   P
2401  GCCCTTTCCA GAGAGCACGG ATAACTTTAT CTTGTTTGAC GAAGTGAGTC CCACACCTCC
      CGGGAAAGGT CTCTCGTGCC TATTGAAATA GAACAAACTG CTTCACTCAG GGTGTGGAGG
                                                             ^begin TM 444   I   T   V   T   H   K   P   E   E   D   T   F   G   V   S   I   A   V   G   L
2461  TATCACTGTG ACCCACAAAC CAGAAGAAGA CACTTTTGGG GTATCCATAG CAGTTGGACT
```

*FIG.–14D*

```
                      ATAGTGACAC TGGGTGTGTTTG GTCTTCTTCT GTGAAAACCC CATAGGTATC GTCAACCTGA
                                                                           ^end TM
      A   A   F   A   C   V   L   L   V   V   L   F   V   M   I   N   K   Y   G   R
464   TGCTGCTTTT GCCTGTGTCC TGTTGGTGGT GTCTTCTTCGTC ATGATCAACA AATATGGTCG
2521  ACGACGAAAA CGGACACAGG ACAACCACCA AGAGAAGCAG TACTAGTTGT TTATACCAGC R   S   K   F   G   M   K   G   P   V   A   V   I   S   G   E   E   D   S   A
484   ACGGTCCAAA TTTGGAATGA AGGGTCCCGT GGCTGTCATC AGTGGTGAGG AGGACTCAGC
2581  TGCCAGGTTT AAACCTTACT TCCCAGGGCA CCGACAGTAG TCACCACTCC TCCTGAGTCG S   P   L   H   H   I   N   H   G   I   T   T   P   S   S   L   D   A   G   P
504   CAGCCCCACTG CACCACATCA ACCACGGCAT CACCACGCCC TCGTCACTGG ATGCCGGGCC
2641  GTCGGGGTGAC GTGGTGTAGT TGGTGCCGTA GTGGTGCGGG AGCAGTGACC TACGGCCCGG D   T   V   V   I   G   M   T   R   I   P   V   I   E   N   P   Q   Y   F   R
524   CGACACTGTG GTCATTGGCA TGACTCGCAT CCCTGTCATT GAGAACCCCC AGTACTTCCG
2701  GCTGTGACAC CAGTAACCGT ACTGAGCGTA GGGACAGTAA CTCTTGGGGG TCATGAAGGC Q   G   H   N   C   H   K   P   D   T   Y   V   Q   H   I   K   R   D   I
544   TCAGGGACAC AACTGCCACA AGCCGGACAC GTATGTGCAG CACATTAAGA GGAGAGACAT
2761  AGTCCCTGTG TTGACGGTGT TCGGCCTGTG CATACACGTC GTGTAATTCT CCTCTCTGTA ^begin TK
      V   L   K   R   E   L   G   E   G   A   F   G   K   V   F   L   A   E   C   Y
564   CGTGCTGAAG CGAGAACTGG GTGAGGGAGC CTTTGGAAAG GTCTTCCTGG CCGAGTGCTA
2821  GCACGACTTC GCTCTTGACC CACTCCCTCG GAAACCTTTC CAGAAGGACC GGCTCACGAT
```

*FIG._14E*

```
584   N   L   S   P   T   K   D   K   M   L   V   A   V   K   A   L   K   D   P   T
2881  CAACCTCAGC CCGACCAAGG ACAAGATGCT TGTGGCTGTG AAGGCCCTGA AGGATCCCAC
      GTTGGAGTCG GGCTGGTTCC TGTTCTACGA ACACCGACAC TTCCGGGACT TCCTAGGGTG

604   L   A   A   R   K   D   F   Q   R   E   A   E   L   L   T   N   L   Q   H   E
2941  CCTGGCTGCC CGGAAGGATT TCCAGAGGGA GGCCGAGCTG CTCACCAACC TGCAGCATGA
      GGACCGACGG GCCTTCCTAA AGGTCTCCCT CCGGCTCGAC GAGTGGTTGG ACGTCGTACT

624   H   I   V   K   F   Y   G   V   C   G   D   G   D   P   L   I   M   V   F   E
3001  GCACATTGTC AAGTTCTATG GAGTGTGCGG CGATGGGGAC CCCCTCATCA TGGTCTTTGA
      CGTGTAACAG TTCAAGATAC CTCACACGCC GCTACCCCTG GGGGAGTAGT ACCAGAAACT

644   Y   M   K   H   G   D   L   N   K   F   L   R   A   H   G   P   D   A   M   I
3061  ATACATGAAG CATGGAGACC TGAATAAGTT CCTCAGGGCC CATGGGCCAG ATGCAATGAT
      TATGTACTTC GTACCTCTGG ACTTATTCAA GGAGTCCCGG GTACCCGGTC TACGTTACTA

664   L   V   D   G   Q   P   R   Q   A   K   G   E   L   G   L   S   Q   M   L   H
3121  CCTTGTGGAT GGACAGCCAC GGGTAGAGCTG GGGCTCTCCC AAATGCTCCA
      GGAACACCTA CCTGTCGGTG CGGTCCGGTT CCCACTCGAC CCCGAGAGGG TTTACGAGGT

684   I   A   S   Q   I   A   S   G   M   V   Y   L   A   S   Q   H   F   V   H   R
3181  CATTGCCAGT CAGATCGCCT CGGGTATGGT GTACCTGGCC TCCCAGCACT TTGTGCACCG
      GTAACGGTCA GTCTAGCGGA GCCCATACCA CATGGACCGG AGGGTCGTGA AACACGTGGC

704   D   L   A   T   R   N   C   L   V   G   A   N   L   L   V   K   I   G   D   F
3241  AGACCTGGCC ACCAGGAACT GCCTGGTTGG AGCGAATCTG CTAGTGAAGA TTGGGGACTT
      TCTGGACCGG TGGTCCTTGA CGGACCAACC TCGCTTAGAC GATCACTTCT AACCCCTGAA
                                                  ^TK insert site 724   G   M   S   R   D   V   Y   S   T   D   Y   Y   R   V   G   G   H   T   M   L
```

FIG._14F

```
3301  CGGCATGTCC AGAGATGTCT ACAGCACGGA TTATTACAGG GTGGGAGGAC ACACCATGCT
      GCCGTACAGG TCTCTACAGA TGTCGTGCCT AATAATGTCC CACCCTCCTG TGTGGTACGA

744      P  I  R     W  M  P  P     E  S  I     M  Y  R     K  F  T  T     E  S  D
3361  CCCCATTCGC TGGATGCCTC CTGAAAGCAT CATGTACCGG AAGTTCACTA CAGAGAGTGA
      GGGGTAAGCG ACCTACGGAG GACTTTCGTA GTACATGGCC TTCAAGTGAT GTCTCTCACT

764      V  W  S     F  G  V  I     L  W  E     I  F  T     Y  G  K  Q     P  W  F
3421  TGTATGGAGC TTCGGGGTGA TCCTCTGGGA GATCTTCACC TATGGAAAGC AGCCATGGTT
      ACATACCTCG AAGCCCCACT AGGAGACCCT CTAGAAGTGG ATACCTTTCG TCGGTACCAA

784      Q  L  S     N  T  E  V     I  E  C     I  T  Q     G  R  V  L     E  R  P
3481  CCAACTCTCA AACACGGAGG TCATTGAGTG CATTACCCAA GGTCGTGTTT TGGAGCGGCC
      GGTTGAGAGT TTGTGCCTCC AGTAACTCAC GTAATGGGTT CCAGCACAAA ACCTCGCCGG

804      R  V  C     P  K  E  V     Y  D  V     M  L  G     C  W  Q  R     E  P  Q
3541  CCGAGTCTGC CCCAAAGAGG TGTACGATGT CATGCTGGGG TGCTGGCAGA GGGAACCACA
      GGCTCAGACG GGGTTTCTCC ACATGCTACA GTACGACCCC ACGACCGTCT CCCTTGGTGT

824      Q  R  L     N  I  K  E     I  Y  K     I  L  H     A  L  G  K     A  T  P
3601  GCAGCGGTTG AACATCAAGG AGATCTACAA AATCCTCCAT GCTTTGGGGA AGGCCACCCC
      CGTCGCCAAC TTGTAGTTCC TCTAGATGTT TTAGGAGGTA CGAAACCCCT TCCGGTGGGG

^stop
                                                  R1 site removed with cut and fill^
844      I  Y  L     D  I  L  G     O
3661  AATCTACCTG GACATTCTTG GCTAGTGGTG GCTGGTGGTC ATGAATTAAT TCAATCGATG
      TTAGATGGAC CTGTAAGAAC CGATCACCAC CGACCACCAG TACTTAATTA AGTTAGCTAC ^sv40 early poly A
3721  GCCGCCATGG CCCAACTTGT TTATTGCAGC TTATAATGGT TACAAATAAA GCAATAGCAT
      CGGCGGTACC GGGTTGAACA AATAACGTCG AATATTACCA ATGTTTATTT CGTTATCGTA
```

FIG._14G

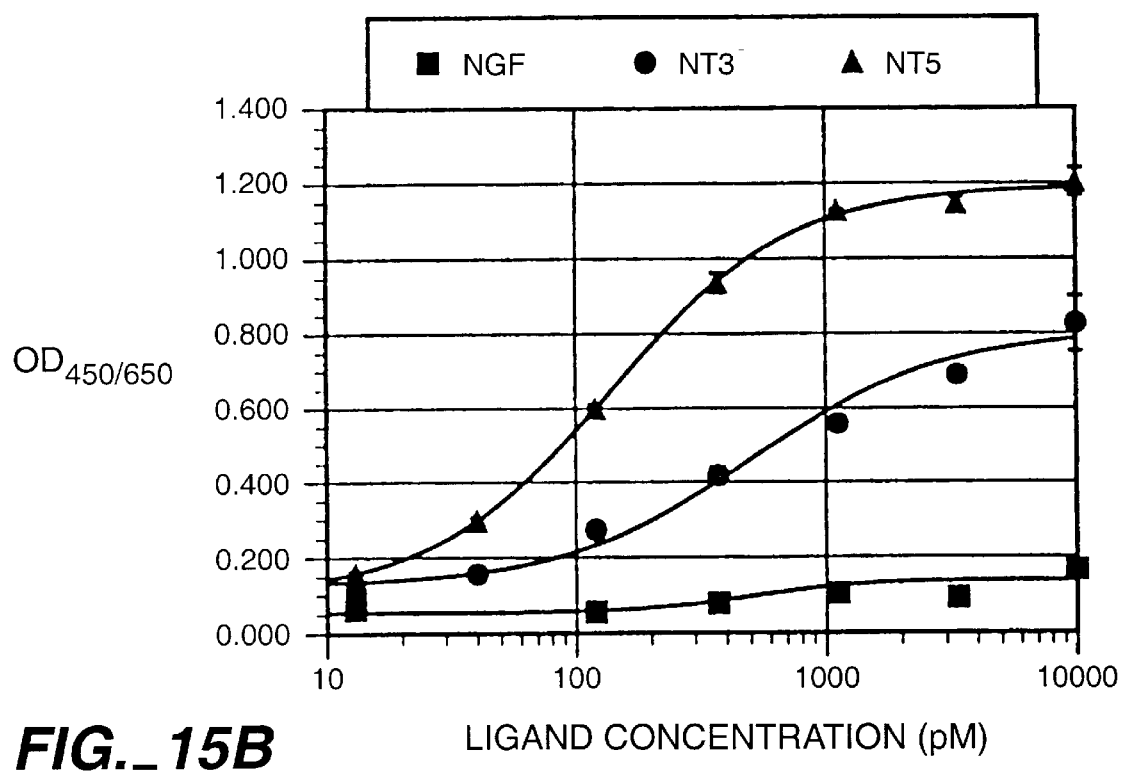
FIG._15B
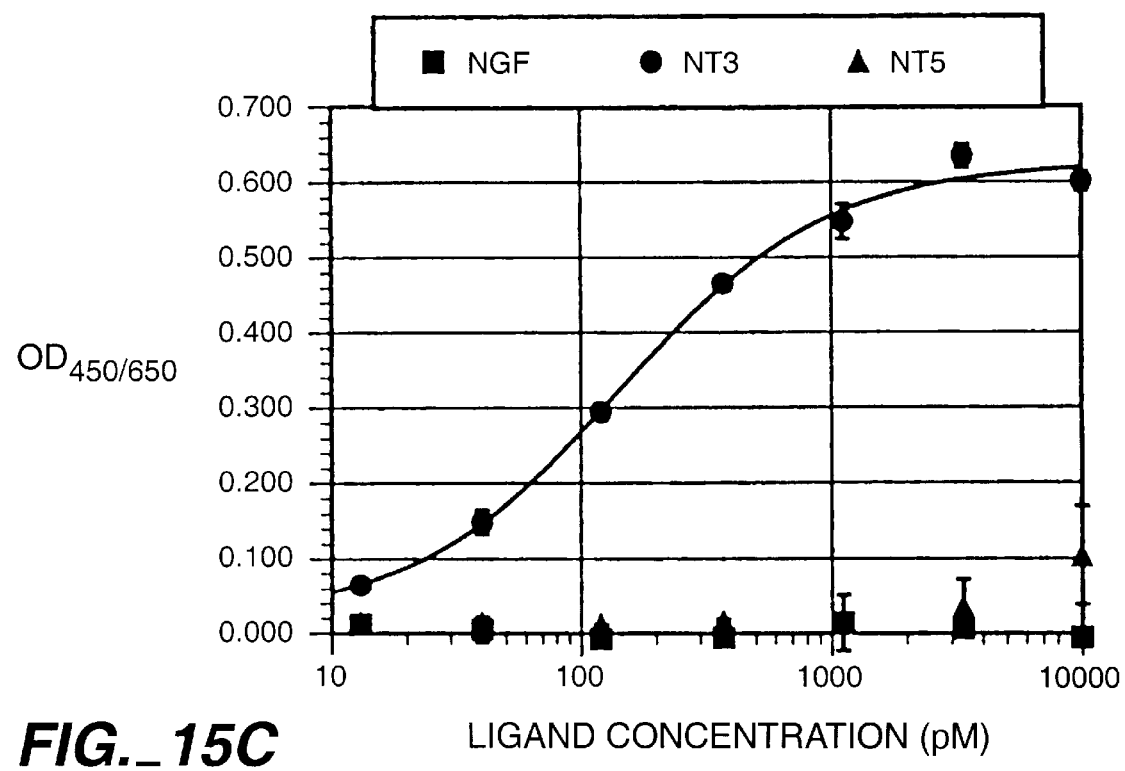
FIG._15C

FIG._16A

```
     aluI                                        aluI
     sstI                            sau3AI pvuII
     sacI                            mboI/ndeII[dam-]
     hgiJII                              dpnI[dam+]
     hgiAI/aspHI                         pvuI/bspCI
     ecl136II                        pleI dpnII[dam-]
     bsp1286                         hinfI taqI[dam-]
     bsiHKAI                      rmaI   mcrI   nspBI
     bmyI                         maeI taqI[dam-]
     banII
     taqI
  1 TTCGAGCTCG CCCGACATTG ATTATTGACT AGAGTCGATC GACAGCTGTG GAATGTGTGT CAGTTAGGGT
    AAGCTCGAGC GGGCTGTAAC TAATAACTGA TCTCAGCTAG CTGTCGACAC CTTACACACA GTCAATCCCA
                    nlaIV                                              sfaNI      scrFI
                    scrFI                                              ppu10I     mvaI
                    mvaI                                               nsiI/avaIII ecoRII
                    ecoRII                                             nlaIII     dsaV
                    dsaV                                               sphI       bstNI
                    bstNI                                              nspI       apyI
                    apyI[dcm+]                                         nspHI      sexAI
                    bsaJI
 71 GTGGAAAGTC CCCAGGCTCC CCAGCAGGCA GAAGTATGCA AAGCATGCAT CTCAATTAGT CAGCAACCAG
    CACCTTTCAG GGGTCCGAGG GGTCGTCCGT CTTCATACGT TTCGTACGTA GAGTTAATCA GTCGTTGGTC
```

FIG._16B

```
                                                                                    nlaIII
              nlaIV                                                                 styI
         scrFI              sfaNI                                                   ncoI
         mvaI                                                          sphI         bslI dsaI
         ecoRII             nsiI/avaIII  ppuI0I                        nspI         aciI bsaJI
         dsaV               nlaIII                                     nspHI
         bstNI
[dcm+]   apyI[dcm+]
         bsaJI
141 GTGTGGAAAG TCCCCAGGCT CCCCAGCAGG CAGAAGTATG CAAAGCATGC ATCTCAATTA GTCAGCAACC
    CACACCTTTC AGGGGTCCGA GGGGTCGTCC GTCTTCATAC GTTTCGTACG TAGAGTTAAT CAGTCGTTGG aciI                  aciI bsrI  aciI            aciI bsaJI
         aciI fokI    aciI          cgcccagttc cgcccATG      cgccccATG
211 ATAGTCCCGC CCCTAACTCC GCCATCCCG CCCCTAACTC CCCCAGTTC CGCCCCATG CCGCCCCATG
    TATCAGGGCG GGGATTGAGG CGGTAGGGC GGGGATTGAG GCGGGTCAAG GCGGGGTAAGA GGCGGGGTAC fnu4HI
                                bglI
                                sfiI
                                haeIII/palI
                           mnlI     mnlI          ddeI
                           haeIII/palI bsaJI mnlI    aluI                            mnlI
                       mnlI bsaJI aciI       haeIII/palI
281 GCTGACTAAT TTTTTTTATT TATGCAGAGG CCGAGGCCGC CTCGGCCTCT GAGCTATTCC AGAAGTAGTG
    CGACTGATTA AAAAAAATAA ATACGTCTCC GGCTCCGGCG GAGCCGGAGA CTCGATAAGG TCTTCATCAC
```

```
                                                              haeIII/palI
                                                              mcrI
                                   rmaI                       eagI/xmaIII/eclXI
                                   styI                       eaeI
                                   bsaJI                      cfrI
                                   blnI                 rmaI  mspI
                                   avrII          aluI  maeI  hpaII
                             haeIII/palI          rmaI  nheI
                         stuI                     maeI  aluI
                         haeI       mnlI mael
             mnlI
351 AGGAGGCTTT TTTGGAGGCC TAGGCTTTTG CAAAAAGCTA GCTTATCCGG
    TCCTCCGAAA AAACCTCCGG ATCCGAAAAC GTTTTTCGAT CGAATAGGCC tfiI
                                  hinFI
    scrFI             aciI
    nciI              thaI
    mspI              fnuDII/mvnI                                             aciI
    hpaII        bstUI                       maeIII  rsaI  csp6I  scfI
    dsaV         bsh1236I                                                     maeIII
    cauII
401 CCGGGAACGG TGCATTGGAA CGGGATTCC  CCGTGCCAAG AGTGACGTAA GTACCGCCTA TAGAGCGATA
    GGCCCTTGCC ACGTAACCTT GGCCTAAGG  GGCACGGTTC TCACTGCATT CATGGCGGAT ATCTCGCTAT
                                                                ^splice donor fnu4HI
          bbvI                                                          pflMI
          nspBII                                                        bslI
          aciI          nlaIII taqI                     sfaNI
471 AGAGGATTTT ATCCCCGCTG CCATCATGGT TCGACCATTG AACTGCATCG TCGCCGTGTC CCAAAATATG
    TCTCCTAAAA TAGGGGCGAC GGTAGTACCA AGCTGGTAAC TTGACGTAGC AGCGGCACAG GGTTTTATAC
    mnlI                 DHFR ATG^
```

```
                                                      haeIII/palI
                                                      haeI
                                                      scrFI
                                                      mvaI        bsrBI
                                                      ecoRII
                                                      dsaV
                                                      bstNI  aciI                    rsaI
                           bsmAI  apyI[dcm+]                            xmnI         csp6I
                           bsaI   bsaJI  mnlI  ddeI   CCTCCGCTCA         asp700      scaI
541  GGGATTGGCA AGAACGGAGA CCTACCCTGG CCTCCGCTCA GGAACGAGTT CAAGTACTTC CAAAGAATGA
     CCCTAACCGT TCTTGCCTCT GGATGGGACC GGAGGCGAGT CCTTGCTCAA GTTCATGAAG GTTTCTTACT scrFI
                                                                               mvaI
                                                                               ecoRII
                                                                               dsaV
                                        tfiI                                   bstNI
        eco57I                          hinfI                                  apyI[dcm+]
        mboII                                                                  sexAI         ddeI
        earI/ksp632I              alwNI     hphI
        mnlI
611  CCACAACCTC TTCAGTGGAA GGTAAACAGA ATCTGGTGAT TATGGGTAGG AAAACCTGGT TCTCCATTCC
     GGTGTTGGAG AAGTCACCTT CCATTTGTCT TAGACCACTA ATACCCATCC TTTTGGACCA AGAGGTAAGG tfiI       tru9I
        hinfI      mseI          mseI     ddeI
        mboII taqI ahaIII/draI  aseI/asnI/vspI                            bslI     mnlI
681  TGAGAAGAAT CGACCTTTAA AGGACAGAAT TAATATAGTT CTCAGTAGAG AACTCAAAGA ACCACCACGA
     ACTCTTCTTA GCTGGAAATT TCCTGTCTTA ATTATATCAA GAGTCATCTC TTGAGTTTCT TGGTGGTGCT
```

FIG._16E

```
sstI
sacI
hgiJII
hgiAI/aspHI
ecl136II
bsp1286
bsiHKAI
  bmyI                                                  tru9I          mspI
  banII                                              aflII/bfrI        hpaII
  aluI             bstXI     fokI sfaNI  mseI                          bsaWI
751 GGAGCTCATT TTCTTGCCAA AAGTTTGGAT GATGCCTTAA GACTTATTGA ACAACCGGAA TTGGCAAGTA
    CCTCGAGTAA AAGAACGGTT TTCAAACCTA CTACGGAATT CTGAATAACT TGTTGGCCTT AACCGTTCAT
                                                                             haeIII/palI
                                                                             haeI
                                                scrFI        scrFI
                                                mvaI          mvaI
                                                ecoRII       ecoRII
                                                dsaV  tfiI   dsaV
                                                bstNI nlaIII bstNI    ddeI
     accI nlaIII          mnlI              apyI[dcm+] hinfI apyI[dcm+]
821 AAGTAGACAT GGTTTGGATA GTCGGAGGCA GTTCTGTTTA CCAGGAAGCC ATGAATCAAC CAGGCCACCT
    TTCATCTGTA CCAAACCTAT CAGCCTCCGT CAAGACAAAT GGTCCTTCGG TACTTAGTTG GTCCGGTGGA
```

FIG._16F

```
                                          nlaIII
                                sau3AI
                              mboI/ndeII[dam-]
                                dpnI[dam+]                            maeII
                                 dpnII[dam-]                         aflIII
       pleI      maeIII alwI[dam-]   apoI    maeIII
       hinfI
891  TAGACTCTTT GTGACAAGGA TCATGCAAGA ATTTGAAAGT GACACGTTTT TCCCAGAAAT TGATTTGGGG
     ATCTGAGAAA CACTGTTCCT AGTACGTTCT TAAACTTTCA CTGTGCAAAA AGGGTCTTTA ACTAAACCCC hgaI
                                 hinlI/acyI
                                  ahaII/bsaHI
                              scrFI
                              mvaI         mnlI
                              ecoRII
                              dsaV
                              bstNI      ecoNI
                              apyI[dcm+]            mnlI
                              bsaJI      bslI ddeI
961  AAATATAAAC CTCTCCCAGA ATACCCAGGC GTCCTCTCTG
     TTTATATTTG GAGAGGGTCT TATGGGTCCG CAGGAGAGAC
         mnlI
```

FIG._16G

```
      scrFI
      mvaI
      ecoRII
      dsaV
      bstNI
      apyI[dcm+]
      sau96I
      avaII                                                                              sfaNI
      asuI  mnlI      sfaNI              accI      mboII                                 mboII
1001 AGGTCCAGGA GGAAAAAGGC ATCAAGTATA AGTTGAAGT CTACGAGAAG AAAGACTAAC AGGAAGATGC
     TCCAGGTCCT CCTTTTTCCG TAGTTCATAT TCAAACTTCA GATGCTCTTC TTTCTGATTG TCCTTCTACG
                                                                     ^END DHFR nlaIII
                                                  styI
                                                  ncoI
                                                  dsaI
                                  ppulOI          bsaJI
                          mnlI    alul  nsiII/avaIII  ATGCATTTT  ATAAGACCAT  GGGACTTTTG
1071 TTTCAAGTTC TCTGCTCCCC TCCTAAAGCT ATGCATTTT ATAAGACCAT GGGACTTTTG
     AAAGTTCAAG AGACGAGGGG AGGATTTCGA TACGTAAAAA TATTCTGGTA CCCTGAAAAC
```

FIG._16H

```
                                                                              sau96I
                                                                              avaII
                                                                              asuI
                                                                              scrFI
                                                                              mvaI
                                                                              ecoRII
                                                                              dsaV
                                                                              bstNI
                                           fnu4HI                             apyI[dcm+]
             styI                          aciI
             bsaJI                         thaI
     sau3AI                                fnuDII/mvnI  tru9I
     mboI/ndeII[dam-]                      bstUI        mseI
     dpnI[dam+]                            bsh1236I     aseI/asnI/vspI
     dpnII[dam-]
     alwI[dam-]
     bstYI/xhoII
1131 CTGGCTTTAG ATCCCCTTGG CTTCGTTAGA ACGCGGCTAC AATTAATACA TAACCTTATG TATCATACAC
     GACCGAAATC TAGGGGAACC GAAGCAATCT TGCGCCGATG TTAATTATGT ATTGGAATAC ATAGTATGTG maeIII
         hphI    scfI       fokI                                           bsII bsaJI
1201 ATACGATTTA GGTGACACTA TAGATAACAT CCACTTTGCC TTTCTCTCCA CAGGTGTCCA CTCCCAGGTC
     TATGCTAAAT CCACTGTGAT ATCTATTGTA GGTGAAACGG AAAGAGAGGT GTCCACAGGT GAGGGTCCAG
```

FIG._16I

```
                                                                scrFI
                                                                nciI
                                                                mspI
                                                                hpaII
                                                                dsaV
                                                                xmaI/pspAI
                                                                smaI
                                                                scrFI
                                                                nciI
                                                                dsaV
                                                                cauII
                                                                bsaJI
                                                                avaI
                                                           sau3AI
                                                           mboI/ndeII[dam-]
                                                           dpnI[dam+]
                                                           dpnII[dam-]
                                                     nlaIV cauII
                                              pleI   bstYI/xhoII
                                              hinfI  bamHI bsaJI
                                        taqI  rmaI   alwI[dam-]
                                        salI  maeI  alwI[dam-]
                                        accI  xbaI  mnlI bsaJI
               scfI                     hincII/hindII
        aluI   pstI
        hindIII bspMI
        bsgI
  mnlI  ddeI
  bsaJI
1271 CAACTGCACC TCGGTTCTAA GCTTCTGCAG GTCGACTCTA GAGGATCCCC
     GTTGACGTGG AGCCAAGATT CGAAGACGTC CAGCTGAGAT CTCCTAGGGG
```

FIG._16J

```
                                    sau96I
                                    haeIII/palI
                            aciI    asuI
                            fnu4HI
                     bglI   nlaIII
                     sfiI   styI
                     eaeI   ncoI
                     cfrI   dsaI                                              aluI
         taqI haeIII/palI                                                     fnu4HI
    ecoRI clal/bsp106 bsaJI                                              bbvI        maeIII
    apoI                                                                                                    rmaI
                                                                                                            bsmI maeI
1321 GGGAATTCA ATCGATGGCC GCCATGGCCC AACTTGTTTA TTGCAGCTTA TAATGGTTAC AAATAAAGCA
     CCCCTTAAGT TAGCTACCGG CGGTACCGGG TTGAACAAAT AACGTCGAAT ATTACCAATG TTTATTTCGT
                                     ^sv40 sfaNI apoI
1391 ATAGCATCAC AAATTCACA AATAAAGCAT TTTTTTCACT GCATTCTAGT TGTGGTTTGT CCAAACTCAT
     TATCGTAGTG TTTAAGTGT TTATTTCGTA AAAAAAGTGA CGTAAGATCA ACACCAAACA GGTTTGAGTA
```

FIG._16K

```
                                                            sau3AI
                                                            mboI/ndeII[dam-]
                                                            dpnI[dam+]
                                                            dpnII[dam-]
                                                            pvuI/bspCI
                                                            mcrI
                                                            taqI[dam-]   tru9I
                                                            claI/bspl06[dam-]
                                                            sau3AI       mseI
                                                            mboI/ndeII[dam-]
                                                            dpnI[dam+] xmnI
                                                            dpnII[dam-]   aseI/asnI/vspI
                                   nlaIII   alwI[dam-]  asp700
                                                                                          rsaI
                                                                                          csp6I
                                                                                          nlaIV
                                                                                          kpnI
                                                                                          hgiCI
                                                                                          banI
                                                                                          asp718    mnlI
                       haeIII/palI                                                        acc65I  ddeI   aciI
               haeI
           styI
        fnu4HI ncoI
         bbvI  dsaI
       hinPI  bsaJI
       hhaI/cfoI nlaIII            mnlI              mnlI
1461 CGGCGCAGCA CCATGGCCTG TATCATGTCT GGATCGATCG GGAATTAATT AAATAACCTC TGAAAGAGGA ACTTGGTTAG GTACCTTCTG AGGCGGAAAG
     GCCGCGTCGT GGTACCGGAC ATAGTACAGA CCTAGCTAGC CCTTAATTAA TTTATTGGAG ACTTTCTCCT TGAACCAATC CATGGAAGAC TCCGCCTTTC
                                                            sv40 origin^
1501
```

FIG._16L

```
                                                                   nlaIV
                                                          scrFI
                                                          mvaI
                                                          ecoRII
                                                          dsaV
                                                          bstNI
                                                          apyI[dcm+]
          aluI                                            bsaJI                              nlaIV
          pvuII
          nspBII
1571 AACCAGCTGT GGAATGTGTG TCAGTTAGGG TGTGGAAAGT CCCCAGGCTC CCCAGCAGGC AGAAGTATGC
     TTGGTCGACA CCTTACACAC AGTCAATCCC ACACCTTTCA GGGGTCCGAG GGGTCGTCCG TCTTCATACG scrFI        scrFI
     sfaNI                   mvaI
          ppu10I             ecoRII                                            mvaI
     nsiI/avaIII             dsaV
     nlaIII                       bstNI                bstNI
          sphI                    apyI[dcm+]           apyI[dcm+]
          nspI                         sexAI           bsaJI
          nspHI
1641 AAAGCATGCA TCTCAATTAG TCAGCAACCA GGTGTGGAAA GTCCCCAGGC TCCCCAGCAG GCAGAAGTAT
     TTTCGTACGT AGAGTTAATC AGTCGTTGGT CCACACCTTT CAGGGGTCCG AGGGGTCGTC CGTCTTCATA sfaNI
          ppu10I
          nsiI/avaIII
          nlaIII
          sphI
          nspI                                                                aciI
          nspHI                     aciI        aciI fokI
1711 GCAAAGCATG CATCTCAATT AGTCAGCAAC CATAGTCCCG CCCCTAACTC CGCCCATCCC GCCCCTAACT
     CGTTTCGTAC GTAGAGTTAA TCAGTCGTTG GTATCAGGGC GGGGATTGAG GCGGGTAGGG CGGGGATTGA
```

FIG._16M

```
                                                          nlaIII
                                                          styI
                                                          ncoI                                                    styI
                                                bslI dsaI                                                         bsaJI
                    bsrI                        aciI bsaJI                                                        blnI                  mnlI
      asiI          aciI   CCGCCCAGTT   CCGCCCATTC   TCCGCCCCAT   GGCTGACTAA   TTTTTTTTAT   TTATGCAGAG            avrII
1781  CGGCCCAGTT   CCGCCCATTC   TCCGCCCCAT   GGCTGACTAA   TTTTTTTTAT   TTATGCAGAG
      GGCGGGTCAA   GGCGGGGTAA   AGGCGGGGTA   CCGACTGATT   AAAAAAAATA   AATACGTCTC
                                                                                                    haeIII/palI
                                                                                                    stuI
                      fnu4HI                                                                        haeI
                      bglI                                                                          mnlI
                      sfiI                                                                mnlI
                      haeIII/palI                                             mnlI
            mnlI      mnlI        ddeI
      haeIII/palI   bsaJI  mnlI   aluI
            bsaJI   aciI   haeIII/palI
1841  GCCGAGGCCG   CCTCGGCCTC   TGAGCTATTC   CAGAAGTAGT   GAGGAGGCTT   TTTTGGAGGC
      CGGCTCCGGC   GGAGCCGGAG   ACTCGATAAG   GTCTTCATCA   CTCCTCCGAA   AAAACCTCCG
```

FIG._16N

```
                                                         hinPI
                                          acil           hhaI/cfoI
                                          haeIII/palI    thaI
                                      mcrI                  bstUI          bspMI
                                      eagI/xmaIII/eclXI  fnuDII/mvnI
                              taqI  eaeI                    hinPI          scfI
                              xhoI  notI                    hhaI/cfoI  tru9I  pstI
                              paeR7I cfrI   tru9I           ascI       ahaIII/draI  bsgI
                              avaI  fnu4HI  pacI        mseI  tru9I bsh1236I mseI   sse8387I
                         mnlI  acI         mseI   tru9I bssHI  swaI
            rmaI              aluI maeIII bsrBI fnu4HI    mseI bssHII swaI
            maeI
     1901 CTAGGCTTTTT GCAAAAAGCT GTTACCTCGA GCGGCCGCTT AATTAAGGCG CGCCATTTAA ATCCTGCAGG
          GATCCGAAAA CGTTTTTCGA CAATGGAGCT CGCCGGCGAA TTAATTCCGC GCGGTAAATT TAGGACGTCC
                                ^start pUC118
                                              ^linearization linker inserted into HpaI site scrFI
                                                              mvaI
                                                              ecoRII
                                                              dsaV
                                                              bstNI
                      haeIII/palI                             apyI[dcm+]                tru9I
                      eaeI                                                              mseI
                      cfrI           maeIII              maeIII
     maeIII           bsrI           maeII bsrI          bsaJI  maeIII
     1971 TAACAGCTTG GCACTGGCCG TCGTTTTACA ACGTCGTGAC CTGGCGTTAC CCAACTTAAT
          ATTGTCGAAC CGTGACCGGC AGCAAAATGT TGCAGCACTG GACCGCAATG GGTTGAATTA
     maeIII           aluI        bsrI                                  
```

FIG._16O

```
                                                                    sau3AI
                                                      sau96I   mboI/ndeII[dam-]
                                               haeIII/palI
                                                  asuI    dpnI[dam+]
                            aluI                     mnlI         dpnII[dam-]
                            pvuII              mboII   aciI  pvuI/bspCI
              fnu4HI        nspBII             earI/ksp632I    mcrI
              bbvI  fokI
2041  CGCCTTGCAG CACATCCCCC CTTCGCCAGC TGGCGTAATA GCGAAGAGGC CCGCACCGAT
      GCGGAACGTC GTGTAGGGGG GAAGCGGTCG ACCGCATTAT CGCTTCTCCG GGCGTGGCTA hinPI
                            hhaI/cfoI
                            nlaIV
                            narI
                            kasI
                            hinlI/acyI
                            hgiCI
                            haeII    aciI
                            banI   sfaNI
                                  ahaII/bsaHI                            sfaNI
                    bglI
2101  CGCCCCTTCCC AACAGTTGCG TAGCCTGAAT GGCGAATGGC GCCTGATGCG GTATTTCTCC CTTACGCATC
      GCGGGAAGGG TTGTCAACGC ATCGGACTTA CCGCTTACCG CGGACTACGC CATAAAGAG GAATGCGTAG
```

FIG._16P

```
                                                    hinPI
                                                    thaI
                                                    fnuDII/mvnI
                                                    bstUI scfI              hinPI
                                                    bsh1236I              hhaI/cfoI
                                       rsaI hhaI/cfoI    fnu4HI
                              csp6I  bsII       aciI
       aciI      aciI      maeII
2171 TGTGCGGGTAT TTCACACCGC ATACGTCAAA GCAACCATAG TACGCGCCCT GTAGCGGGCG
     ACACGCCATA AAGTGTGGCG TATGCAGTTT CGTTGGTATC ATGCGCGGGA CATCGCCGCG fnu4HI
           thaI                                                        hinPI
           fnuDII/mvnI                hinPI                          hhaI/cfoI
           bctUI           thaI     hhaI/cfoI               rmaI
           hinPI aciI      fnuDII/mvnI                         hinPI haeII
           hhaI/cfoI       bstUI                             hhaI/cfoI  bsrBI
     tru9I aciI            bsh1236I     aciI                haeII maeI aciI
     mseI bsh1236I         maeIII bbvI maeIII
2231 ATTAAGCGCG GCGGGTGTGG TGGTTACGCG CAGCGTGACC GCTACACTTG CCAGCGCCCT AGCGCCCGCT
     TAATTCGCGC CGCCCACACC ACCAATGCGC GTCGCACTGG CGATGTGAAC GGTCGCGGGA TCGCGGGCGA nlaIV
                                                                        hgiJII
                                                                        bsp1286
                                         mspI                           bmyI
                                         hpaII                          banII
                                         naeI              aluI
                            mboII        maeII cfr10I
2301 CCTTTCGCTT TCTTCCCTTC CTTTCTCGCC ACGTTCGCCG GCTTTCCCCG TCAAGCTCTA AATCGGGGGC
     GGAAAGCGAA AGAAGGGAAG GAAAGAGCGG TGCAAGCGGC CGAAAGGGGC AGTTCGAGAT TTAGCCCCCG
```

FIG. 16Q

```
                                               mnlI
                                               nlaIV
                                               hgiCI
                                               banI  taqI                         hphI
              nlaIV
2371 TCCCTTAGG GTTCCGATTT AGTGCTTTAC GGCACCTCGA CCCCAAAAAA CTTGATTTGG
     AGGGAAATCC CAAGGCTAAA TCACGAAATG CCGTGGAGCT GGGGTTTTTT GAACTAAACC maeII  haeIII/palI                                 maeII pleI
          draIII sau96I                                      drdI  hinfI maeII
          bsaAI  asuI
2401 GTGATGGTTC ACGTAGTGGG CCATCGCCCT GATAGACGGT TTTTCGCCCT TTGACGTTGG AGTCCACGTT
     CACTACCAAG TGCATCACCC GGTAGCGGGA CTATCTGCCA AAAAGCGGGA AACTGCAACC TCAGGTGCAA tru9I                                          bslI
     mseI  pleI                                     bslI  avaI
           hinfI          bsrI
2501 CTTTAATAGT GGACTCTTGT TCCAAACTGG AACCCTATCT CGGGCTATTC TTTTGATTTA
     GAAATTATCA CCTGAGAACA AGGTTTGACC TTGGGATAGA GCCCGATAAG AAAACTAAAT tru9I
                                                             mseI
                   haeIII/palI                  tru9I
                             tru9I mseI  aluI   mseI  apoI
2571 TAAGGGATTT TGCCGATTTC GGCCTATTGG TTAAAAAATG AGCTGATTTA ACAAAAATTT
     ATTCCCTAAA ACGGCTAAAG CCGGATAACC AATTTTTTAC TCGACTAAAT TGTTTTTAAA
```

FIG._16R

```
                                                                hgiAI/aspHI
                                                                bsp1286
                                                                bsiHKAI
                                  maeII                         bmyI   ddeI
               apoI               psp1406I                      apaLI/snoI  rsaI
     thaI      tru9I              tru9I                         alw44I/snoI csp6I
     fnuDII/mvnI                                                                  bsrI          hinPI
     bstUI                                                                        maeIII        fnu4HI
     bsh1236I  mseI               sspI  mseI                                      maeII  nlaIII hhaI/cfoI
2631 AACGCGAATT TTAACAAAAT ATTAACGTTT ACAATTTTAT GGTGCACTCT CAGTACAATC                       aspI bbvI
     TTGCGCTTAA AATTGTTTTA TAATTGCAAA TGTTAAAATA CCACGTGAGA GTCATGTTAG fnu4HI    tru9I                                                         sfaNI
            sfaNI    aciI      mseI              aciI         bsaAI tth111I/aspI bbvI        mspI
2691 TGCTCTGATG CCGCATAGTT AAGCCAACTC CGCTATCGCT ACGTGACTGG GTCATGGCTG CGCCCCGACA             hpaII
     ACGAGACTAC GGCGTATCAA TTCGGTTGAG GCGATAGCGA TGCACTGACC CAGTACCGAC GCGGGGCTGT             scrFI
                                                                                             nciI
                          hinPI                                                              dsaV fokI       maeIII
                          hhaI/cfoI                                                                  cauII  aciI        aluI
                          thaI                                                                               drdI
                          fnuDII/mvnI
                          bstUI
               nspBII bsh1236I
     aciI      aciI hgaI                     drdI
2761 CCCGCCAACA CCCGCTGACG CGCCCTGACC GGCTTGTCTG CTCCCGGCAT CCGCTTACAG ACAAGCTGTG
     GGGCGGTTGT GGGCGACTGC GCGGGACTGG CCGAACAGAC GAGGGCCGTA GGCGAATGTC TGTTCGACAC
```

FIG._16S

```
                                                                                       thaI
                                                                                       fnuDII/mvnI
                                                                                       bstUI
                                                                                       bsh1236I
                                                                                       hinPI
                                                                                       hhaI/cfoI
                                                                                       thaI mnlI
                                                                                       fnuDII/mvnI
                                                                                       bstUI
                                                                                       bsh1236I
           scrFI
           nciI
           mspI
           hpaII           nspI
           dsaV            nspHI
      esp3I      fnu4HI
      bsmAI      bbvI                                   hphI         hphI
      bslI  cauII aluI nlaIII  mnlI
2831  ACCGTCTCCG GGAGCTGCAT GTGTCAGAGG TTTCACCGT CATCACCGAA ACGCGGAGG CAGTATTCTT
      TGGCAGAGGC CCTCGACGTA CACAGTCTCC AAAAGTGGCA GTAGTGGCTT TGCGCGCTCC GTCATAAGAA
                    mnlI
                    haeIII/palI                                      nlaIII
         mboII      sau96I                                 tru9I  rcaI
         bpuAI      asuI                                      mseI  bspHI
         bbsI       eco0109I/draII
2901  GAAGACGAAA GGGCCCTCGTG ATACGCCTAT TTTTATAGGT TAATGTCATG
      CTTCTGCTTT CCCGGAGCAC TATGCGGATA AAAATATCCA ATTACAGTAC
                                                                        aciI
                                                                        thaI
                                                                        fnuDII/mvnI
                                                                        bstUI
                                                                        bsh1236I
                          hinII/acyI                                    hinPI
                          ahaII/bsaHI                                   hhaI/cfoI
                          aatII
                   ddeI maeII
2951  ATAATAATGG TTTCTTAGAC GTCAGGTGGC ACTTTTCGGG GAAATGTGCG
      TATTATTACC AAAGAATCTG CAGTCCACCG TGAAAAGCCC CTTTACACGC
```

FIG._16T

```
                                                                    bsmAI
                                                                     rcaI
                                                          bsrBI nlaIII
                                                            aciI bspHI
     nlaIV
3001 CGGAACCCCT ATTTGTTTAT TTTTCTAAAT ACATTCAAAT ATGTATCCGC TCATGAGACA ATAACCCTGA
     GCCTTGGGGA TAAACAAATA AAAAGATTTA TGTAAGTTTA TACATAGGCG AGTACTCTGT TATTGGGACT mboII
            sspI                     earI/ksp632I
3071 TAAATGCTTC AATAATATTG AAAAGGAAG AGTATGAGTA TTCAACATTT CCGTGTCGCC CTTATTCCCT
     ATTTACGAAG TTATTATAAC TTTTCCTTC TCATACTCAT AAGTTGTAAA GGCACAGCGG GAATAAGGGA fnu4HI
      aciI                              hphI               hphI       sfaNI
3141 TTTTTGCGGC ATTTTGCCTT CCTGTTTTTG CTCACCCAGA AACGCTGGTG AAAGTAAAAG
     AAAAACGCCG TAAAACGGAA GGACAAAAAC GAGTGGGTCT TTGCGACCAC TTTCATTTTC hgiAI/aspHI
                     bsp1286
                     bsiHKAI                                     sau3AI
            sau3AI    bmyI                                     mboI/ndeII[dam-]
          mboI/ndeII[dam-]                                       dpnI[dam+]
            dpnI[dam+]                                          dpnII[dam-]
            dpnII[dam-]                                         bstYI/xhoII
        mboII[dam-]  apaLI/snoI             taqI              alwI[dam-]  aciI
         eco57I    alw44I/snoI            maeIII              bsrI    nspBII
3201 ATGCTGAAGA TCAGTTGGGT GCACGAGTGG GTTACATCGA ACTGGATCTC AACAGCGGTA
     TACGACTTCT AGTCAACCCA CGTGCTCACC CAATGTAGCT TGACCTAGAG TTGTCGCCAT
```

FIG._16U

```
     sau3AI
     mboI/ndeII[dam-]                    maeII
     dpnI[dam+]                          psp1406I                        hgiAI/asphI
     dpnII[dam-]                         xmnI                            bsp1286I    tru9I
     alwI[dam-]                          asp700                          bsiHKAI     mseI
     bstYI/xhoII              mboII                                      bmyI        ahaIII/draI
3261 AGATCCTTGA GAGTTTTCGC CCCGAAGAAC GTTTTCCAAT GATGAGCACT TTTAAAGTTC
     TCTAGGAACT CTCAAAAGCG GGGCTTCTTG CAAAAGGTTA CTACTCGTGA AAATTTCAAG scrFI
                                          nciI
                   aciI                   mspI
                   thaI                   hpaII
                   fnuDII/mvnI            dsaV
                   bstUI                  hinII/acyI
                   bsh1236I               hgaI cauII                              aciI
                   hinPI                  ahaII/bsaHI               bcgI mcrI fnu4HI
                   hhaI/cfoI                                AGAGCAACTC GGTCGCCGCA
3321 TGCTATGTGTGG CGCGGTATTA TCCCCGTGATG ACGCCGGGCA AGAGCAACTC GGTCGCCGCA
     ACGATACACC GCGCCATAAT AGGGCACTAC TGCGGCCCGT TCTCGTTGAG CCAGCGGCGT rsaI
                       csp6I     bsrI
                       scaI   hphI maeIII        sfaNI        fokI
           ddeI
3381 TACACTATTC TCAGAATGAC TTGGTTGAGT ACTCACCAGT CACAGAAAAG CATCTTACGG
     ATGTGATAAG AGTCTTACTG AACCAACTCA TGAGTGGTCA GTGTCTTTTC GTAGAATGCC
```

FIG._16V

```
                                                                                haeIII/palI
                                                                                eaeI
                                                                                cfrI
                                                          fnu4HI                fnu4HI
            nlaIII                    bbvI          nlaIII                      aciI
3441 ATGGCATGAC AGTAAGAGAA TTATGCAGTG CTGCCATAAC CATGAGTGAT AACACTGCGG CCAACTTACT
     TACCGTACTG TCATTCTCTT AATACGTCAC GACGGTATTG GTACTCACTA TTGTGACGCC GGTTGAATGA
                           sau96I
                           avaII
                           asuI                                                 nlaIII
                   sau3AI                                                       sau3AI maeIII
                   mboI/ndeII[dam-]                                             mboI/ndeII[dam-]
                   dpnI[dam+]                                                   dpnI[dam+]
                   dpnII[dam-]                                                  dpnII[dam-]
                   pvuI/bspCI                                          nlaIII alwI[dam-]
                   mcrI   mnlI            aluI     aciI
3511 TCTGACAACG ATCGGAGGAC CGAAGGAGCT AACCGCTTTT TTGCACAACA TGGGGGATCA TGTAACTCGC
     AGACTGTTGC TAGCCTCCTG GCTTCCTCGA TTGGCGAAAA AACGTGTTGT ACCCCCTAGT ACATTGAGCG
              mspI
       sau3AI nlaIV
       mboI/ndeII[dam-] aluI                                                    fnu4HI
       dpnI[dam+]     hpaII                                         maeIII sfaNI bbvI
       dpnII[dam-] bsaWI
3581 CTTGATCGTT GGGAACCGGA GCTGAATGAA GCCATACCAA ACGACGAGCC TGACACCACG ATGCCAGCAG
     GAACTAGCAA CCCTTGGCCT CGACTTACTT CGGTATGGTT TGCTGCTCGG ACTGTGGTGC TACGGTCGTC
```

```
                                 hinPI                                                        mspI
                                 hhaI/cfoI                                                    hpaII
                                 mstI                                                         scrFI
                                 aviII/fspI            bsrI                          aluI     nciI
                        maeII             tru9I                                      rmaI     dsaV
                        psp1406I          mseI                                       maeI     cauII
     3651 CAATGGCAAC AACGTTGCGC AAACTATTAA CTGGCGAACT ACTTACTCTA GCTTCCCGGC
          GTTACCGTTG TTGCAACGCG TTTGATAATT GACCGCTTGA TGAATGAGAT CGAAGGGCCG bglI
                                                                                              sau96I
                                                           sau96I                             haeIII/palI
          tru9I                                            avaII              hinPI   asuI    mspI
          mseI    bsrI              aciI                   asuI               hhaI/cfoI       hpaII
          aseI/asnI/vspI  mnlI
     3711 AACAATTAAT AGACTGGATG GAGGCGGATA AAGTTGCAGG ACCACTTCTG CGCTCGGCCC TTCCGGCTGG
          TTGTTAATTA TCTGACCTAC CTCCGCCTAT TTCAACGTCC TGGTGAAGAC GCGAGCCGGG AAGGCCGACC mspI                    thaI
                                           hpaII                   fnuDII/mvnI
                                           cfr10I                  bstUI
                                           nlaIV hphI    bsmAI aciI                  fnu4HI
                             gsuI/bpmI                   bsaI bsh1236I               bbvI
     3781 CTGGTTTATT GCTGATAAAT CTGGAGCCGG TGAGCGTGGG TCTCGCGGTA TCATTGCAGC
          GACCAAATAA CGACTATTTA GACCTCGGCC ACTCGCACCC AGAGCGCCAT AGTAACGTCG
```

```
      sau96I
       asuI
       nlaIV                                                                                pleI
       bsrI haeIII/palI    mnlI                                        eam1105I             hinfI
3841  ACTGGGGCCA GATGGTAAGC CCTCCCGTAT CGTAGTTATC TACACGACGG GGAGTCAGGC
      TGACCCCGGT CTACCATTCG GGAGGGCATA GCATCAATAG ATGTGCTGCC CCTCAGTCCG ddeI
                           sau3AI         nlaIV
                           mboI/ndeII[dam-]
                           dpnI[dam+]     hgiCI         tru9I
                           dpnII[dam-]    banI mnlI     mseI
       fokI       GAACGAAATA GACAGATCGC TGAGATAGGT GCCTCACTGA TTAAGCATTG
3901  AACTATGGAT
      TTGATACCTA CTTGCTTTAT CTGTCTAGCG ACTCTATCCA CGGAGTGACT AATTCGTAAC tru9I
                                                         mseI              tru9I
                                                         ahaIII/draI       mseI
      maeIII
3961  GTAACTGTCA GACCAAGTTT ACTCATATAT ACTTTAGATT GATTAAAAC TTCATTTTTA
      CATTGACAGT CTGGTTCAAA TGAGTATATA TGAAATCTAA CTAAATTTG AAGTAAAAAT rmaI        sau3AI
                 sau3AI hphI mboI/ndeII[dam-]
                 mboI/ndeII[dam-]
                 dpnI[dam+]  dpnI[dam+]
                 dpnII[dam-] dpnII[dam-]
      tru9I bstYI/xhoII     alwI[dam-]                          nlaIII               maeII
      mseI  alwI[dam-]      bstYI/xhoII                         rcaI                 tru9I
      ahaIII/draI maeI mboII[dam-]                              bspHI                mseI
4021  ATTTAAAAGG ATCTAGGTGA AGATCCTTTT TGATAATCTC ATGACCAAAA TCCCTTAACG TGAGTTTTCG
      TAAATTTTCC TAGATCCACT TCTAGGAAAA ACTATTAGAG TACTGGTTTT AGGGAATTGC ACTCAAAAGC
```

FIG._16Y

```
                                                      sau3AI
                                                      mboI/ndeII[dam-]
                                                      dpnI[dam+]        sau3AI
                                                      dpnII[dam-]       mboI/ndeII[dam-]
                                                      bstYI/xhoII       dpnI[dam+]
                                       sau3AI         alwI[dam-]        dpnII[dam-]
                                       mboI/ndeII[dam-]                 alwI[dam-]
                                       dpnI[dam+]    mboI[dam-]
                hgaI                   dpnII[dam-]                      bstYI/xhoII
                ddeI
4091 TTCCACTGAG CGTCAGACCC CGTAGAAAAG ATCAAAGGAT CTTCTTGAGA TCCTTTTTTT
     AAGGTGACTC GCAGTCTGGG GCATCTTTTC TAGTTTCCTA GAAGAACTCT AGGAAAAAAA thaI
        fnuDII/mvnI
        bstUI
        bsh1236I
        hinPI      fnu4HI                              aciI
        hhaI/cfoI  bbvI                                nspBII
4151 CTGCGCGTAA TCTGCTGCTT GCAAACAAAA AAACCACCGC TACCAGCGGT GGTTGTTTG
     GACGCGCATT AGACGACGAA CGTTTGTTTT TTTGGTGGCG ATGGTCGCCA CCAAACAAAC sau3AI
        mboI/ndeII[dam-]
        dpnI[dam+]
        dpnII[dam-]
        alwI[dam-]
     mspI                       bsrI                       hinPI
     hpaII    aluI               maeIII    eco57I          hhaI/cfoI
4211 CCGGATCAAG AGCTACCAAC TCTTTTTCCG AAGGTAACTG GCTTCAGCAG AGGCAGATA CCAAATACTG
     GGCCTAGTTC TCGATGGTTG AGAAAAAGGC TTCCATTGAC CGAAGTCGTC TCGCGTCTAT GGTTTATGAC
```

FIG._16Z-1

```
            rmaI              haeIII/palI
            maeI     bsl I     haeI              scfI      aciI         mnlI
4281 TCCTTCTAGT GTAGCCGTAG TTAGGCCACC ACTTCAAGAA CTCTGTAGCA CCGCCTACAT ACCTCGCTCT
     AGGAAGATCA CATCGGCATC AATCCGGTGG TGAAGTTCTT GAGACATCGT GGCGGATGTA TGGAGCGAGA scrFI
                                                                nciI
                                    fnu4HI                      mspI
                                    bbvI                        hpaII        pleI
                   alwNI            bsrI                        dsaV         hinfI
              bsrI    fnu4HI                                    cauII
              maeIII   bbvI    bsrI
4351 GCTAATCCTG TTACCAGTGG CTGCTGCCAG TGGGCGATAAG TCGTGTCTTA CCGGGTTGGA CTCAAGACGA
     CGATTAGGAC AATGGTCACC GACGACGGTC ACCGCTATTC AGCACAGAAT GGCCCAACCT GAGTTCTGCT hgiAI/aspHI
                         nspBII                        bsp1286
                         fnu4HI                        bsiHKAI
              mspI       bbvI mcrI                     bmyI
              hpaII      hinPI aciI                    apaLI/snoI
              bsaWI      hhaI/cfoI                     alw44I/snoI  aluI
              maeIII
4421 TAGTTACCGG ATAAGGCCA GCGGTCGGGC TGAACGGGGG GTTCGTGCAC ACAGCCCAGC TTGGAGCGAA
     ATCAATGGCC TATTCCGCGT CGCCAGCCCG ACTTGCCCCC CAAGCACGTG TGTCGGGTCG AACCTCGCTT hinPI
                   ddeI        scfI                             hhaI/cfoI
                                                                haeII
4491 CGACCTACAC CGAACTGAGA TACCTACAGC GTGAGCATTG AGAAAGCGCC ACGCTTCCCG AAGGGAGAAA
     GCTGGATGTG GCTTGACTCT ATGGATGTCG CACTCGTAAC TCTTTCGCGG TGCGAAGGGC TTCCCTCTTT
```

FIG. 16Z-2

```
                                                              scrFI
                                                              mvaI
                                                              ecoRII  mvaI
                                                              dsaV    ecoRII
                                                              bstNI
                                                    hinPI mnlI    bsaJI
                                                    hhaI/cfoI alul apyI[dcm+]
               mspI
               hpaII
               bsII    fnu4HI
        aciI   bsaWI   aciI
4561 GCGGGACAGG TATCCGGTAA GCGGCAGGGT CGGAACAGGA GAGGCACGA GGGAGCTTCC AGGGGAAAC
     CCGCCTGTCC ATAGGCCATT CGCCGTCCCA GCCTTGTCCT CTCGCGTGCT CCCTCGAAGG TCCCCCTTTG scrFI dsaV
        bstNI                                                      taqI
        apyI[dcm+]                          mnlI drdI hgaI         sfaNI
4631 GCCTGGTATC TTTATAGTCC TGTCGGGTTT CGCCACCTCT GACTTGAGCG TCGATTTTTG TGATGCTCGT
     CGGACCATAG AAATATCAGG ACAGCCCAAA GCGGTGGAGA CTGAACTCGC AGCTAAAAAC ACTACGAGCA haeIII/palI
                                           fnu4HI
                                           aciI
                                           thaI bslI
                                           fnuDII/mvnI
                                           bstUI
                 nlaIV                     bsh1236I
                 aciI
4701 CAGGGGGGCG GAGCCTATGG AAAAACGCCA GCAACGCGGC
     GTCCCCCCGC CTCGGATACC TTTTTGCGGT CGTTGCGCCG
```

FIG._16Z-3

```
                                                                                                    tfiI
                                                                                                    hinfI
                    haeIII/palI
                    scrFI
                    mvaI bslI
                    ecoRII
                    dsaV                                                   nspI
                    bstNI                                                  nspHI
                    apyI[dcm+]           haeIII/palI                       aflIII
             nlaIV hael                  haeI               nlaIII
4741 CTTTTTACGG TTCCTGGCCT TTTGCTGGCC TTTGCTCAC ATGTTCTTTC CTGGCGTTATC CCCTGATTCT
     GAAAAATGCC AAGGACCGGA AAACGACCGG AAACGAGTG TACAAGAAAG GACGCAATAG GGGACTAAGA fnu4HI
                                                              bbvI
                                              bsrBI           aciI
                                acil          aciI fnu4HI     mcrI
                                alul          fnu4HI           mcrI
4811 GTGGATAACC GTATTACCGC CTTTGAGTGA GCTGATACCG CTCGCCGCAG CCGAACGACC
     CACCTATTGG CATAATGGCG GAAACTCACT CGACTATGGC GAGCGGCGTC GGCTTGCTGG hinPI
                                 haeII
                                 sapI hhaI/cfoI                   mnlI
            mnlI aciI earI/ksp632I                                 aciI
4871 GAGCGGCAGCG AGTCAGTGAG CGAGGAAGCG GAAGAGCGCC CAATACGCAA ACCGCCTCTC
     CTCGCCGTCGC TCAGTCACTC GCTCCTTCGC CTTCTCGCGG GTTATGCGTT TGGCGGAGAG
```

FIG. 16Z-4

```
                                                                                              bsrI    aciI
       thaI                                                                                   scrFI
       fnuDII/mvnI                                                                            mvaI
       bstUI                                                                                  ecoRII
       bsh1236I                                                                               dsaV
       hinPI                                                                          nlaIV   bstNI
       hhaI/cfoI                  tru9I   aluI                                        hgiCI   apyI[dcm+]
       thaI                                                                           banI    bsaJI
       fnuDII/mvnI                                pvuII
       bstUI                            aseI/asnI/vspI
       bsh1236I haeIII/palI
       bslI eaeI    tfiI aseI/asnI/vspI
       aciI cfrI hinfI  mseI nspBII
4931 CCCGCGCGTT GGCCGATTCA TTAATCCAGC TGGCACGACA GGTTTCCCGA CTGGAAAGCG
     GGGCGCGCAA CCGGCTAAGT AATTAGGTCG ACCGTGCTGT CCAAAGGGCT GACCTTTCGC tru9I
                          mseI    maeIII
              hinPI       aseI/asnI/vspI     mnlI
              hhaI/cfoI
4991 GGCAGTGAGC GCAACGCAAT TAATGTGAGT TACCTCACTC ATTAGGCACC CCAGGCTTTA CACTTTATGC
     CCGTCACTCG CGTTGCGTTA ATTACACTCA ATGGAGTGAG TAATCCGTGG GGTCCGAAAT GTGAAATACG
```

FIG._16Z-5

```
          mspI                    aciI                          nlaIII
            hpaII                   bsrBI              aluI
5061 TTCCGGCTCG TATGTTGTGT GGAATTGTGA GCGGATAACA ATTTCACACA GGAAACAGCT ATGACCATGA
     AAGGCCGAGC ATACAACACA CCTTAACACT CGCCTATTGT TAAAGTGTGT CCTTTGTCGA TACTGGTACT tru9I
           mseI
            aseI/asnI/vspI
             xmnI
              asp700
5131 TTACGAATTA A
     AATGCTTAAAT T >length: 5141
```

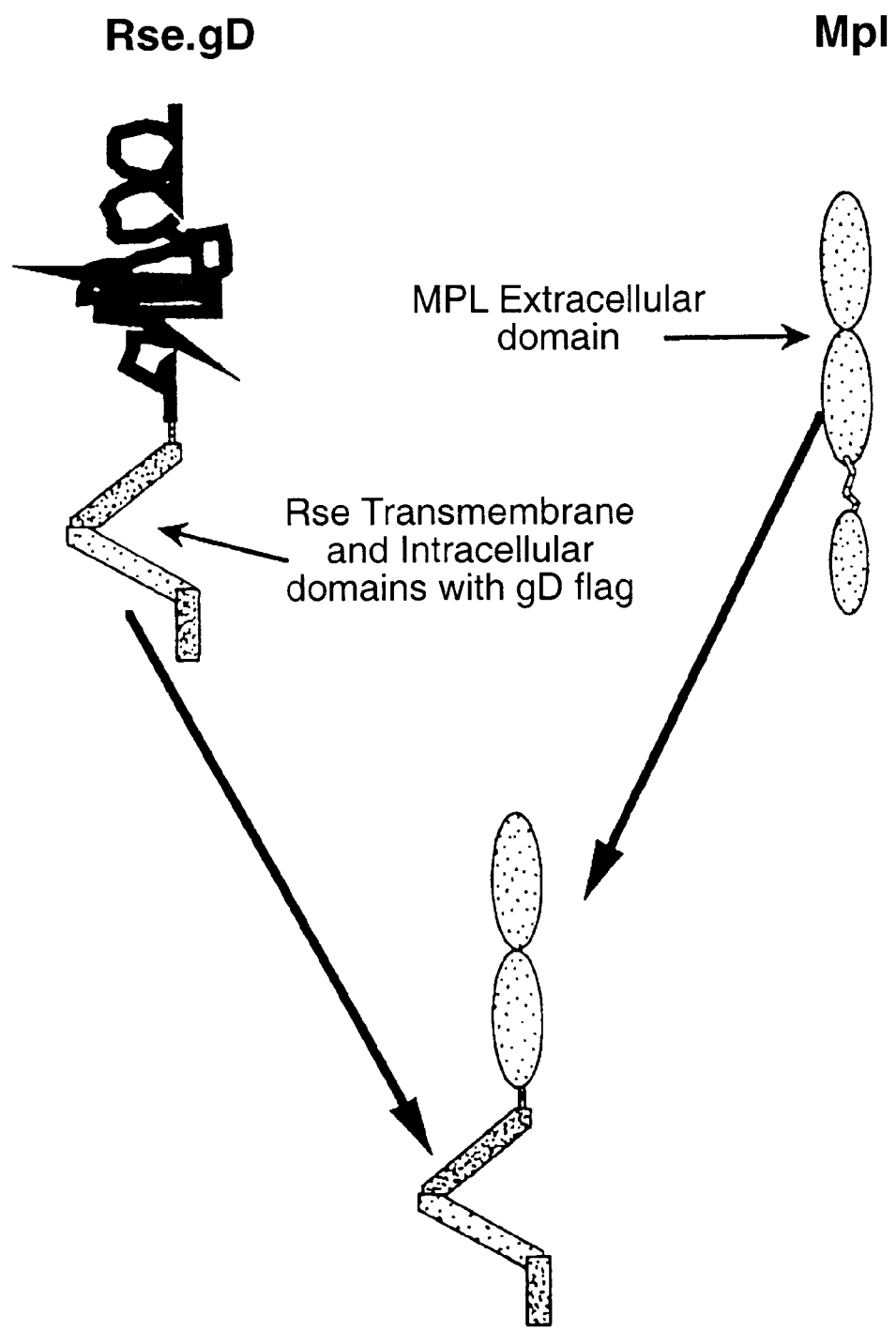
FIG._17

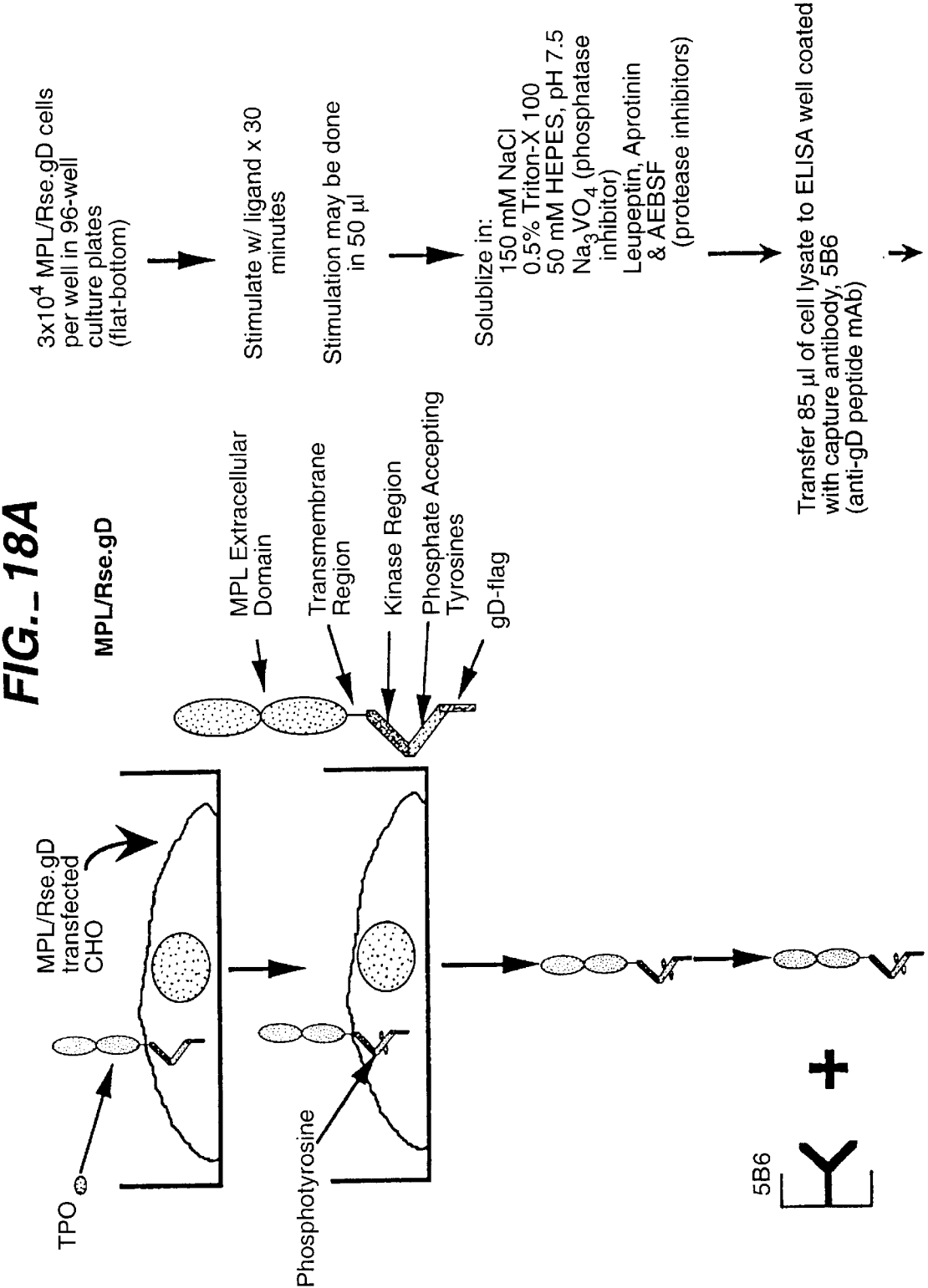

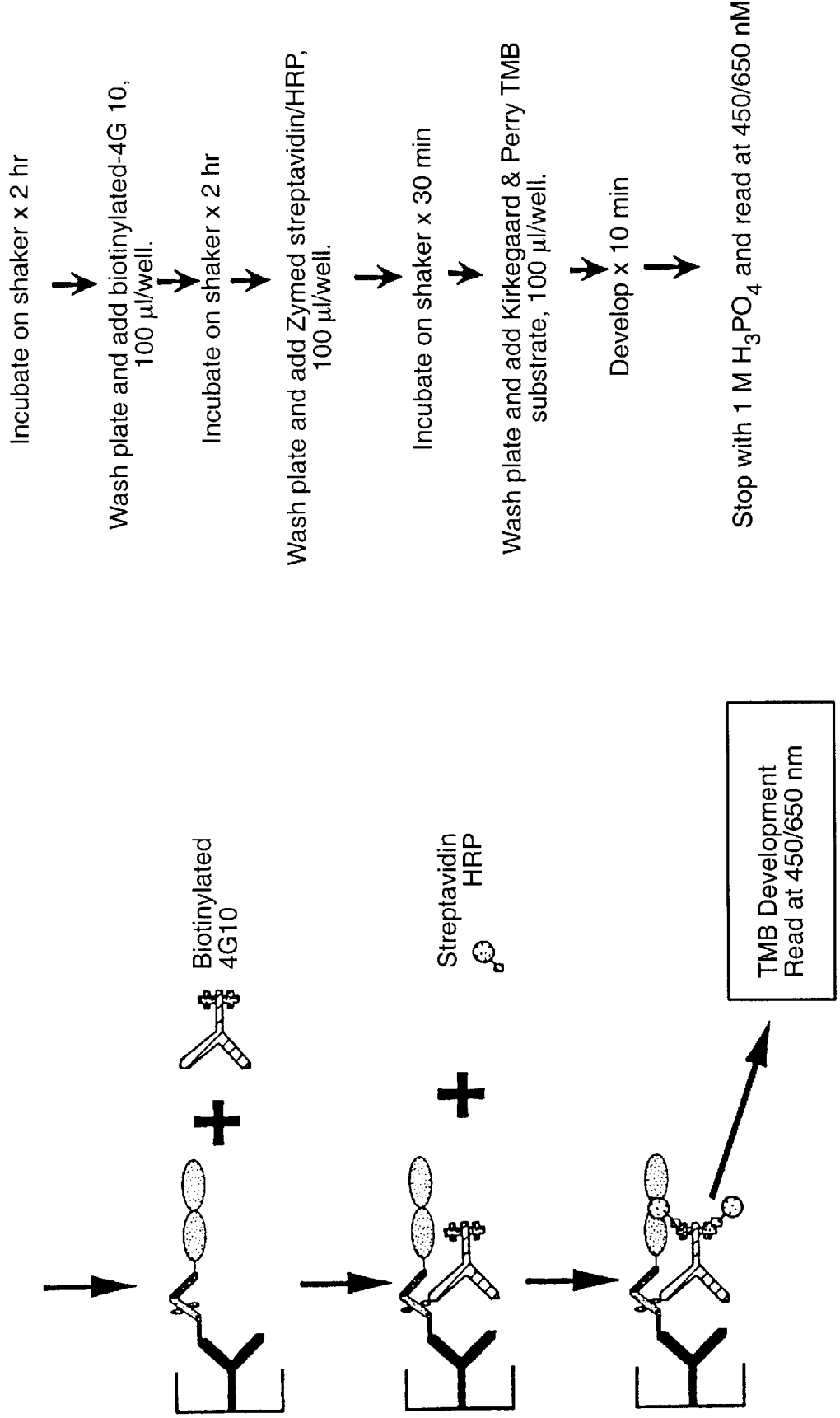
FIG._18B

KINASE RECEPTOR ACTIVATION ASSAY

This application is a 371 of PCT/US94/13329 filed Nov. 18, 1994 and a continuation-in-part of Ser. No. 08/286,305 filed Aug. 5, 1994, now U.S. Pat. No. 5,766,863 which is a continuation-in-part of Ser. No. 08/170,558 filed Dec. 20, 1993, which is a continuation of Ser. No. 08/157,563 filed Nov. 23, 1993, now abandoned.

BACKGROUND OF THE INVENTION

1. Field of the Invention

This invention relates to a kinase receptor activation (KIRA) assay. In particular, the invention relates to an assay for measuring autophosphorylation of the kinase domain of a receptor protein tyrosine kinase (rPTK) using a kinase receptor activation, enzyme-linked immunosorbent assay (KIRA ELISA).

2. Description of Related Art

One mechanism for signal transduction in animals involves protein phosphorylation. Protein phosphorylation involves the action of protein kinase, an enzyme that transfers a phosphate group from a phosphate donor onto an acceptor amino acid in a substrate protein. Protein phosphatases provide a means for reversing the signal when the stimulus is removed.

Protein kinases have multiple substrates, and classification of the protein kinases is based on the acceptor amino acid specificity. The two most well characterized protein kinases are the protein kinases with a protein alcohol group as acceptor called protein serine/threonine kinases and the protein kinases with a protein phenolic group as acceptor called protein tyrosine kinases (Hunter, *Methods in Enzymology* 200: 3–9 [1991]).

The most well known type of signal-transducing protein kinases are growth factor receptor protein tyrosine kinases (rPTKs). rPTKs usually comprise a large, glycosylated, extracellular ligand binding domain (ECD) and an intracellular domain (ICD) which contains a tyrosine kinase catalytic domain. A single hydrophobic transmembrane (TM) domain connects the ECD and ICD. Examples of rPTKs include the insulin receptor, epidermal growth factor receptor (EGF-R), platelet-derived growth factor receptor (PDGF-R), insulin-like growth factor 1 receptor (IGF-1-R), and the HER2 receptor, to name a few. See, for example, Ullrich and Schlessinger *Cell* 61: 203–212 (1990) and Fantl et al., *Annu. Rev. Biochem.* 62: 453–481 (1993). rPTKs can phosphorylate exogenous protein substrates and intrinsic tyrosine residues via their catalytic tyrosine kinase domain. The intrinsic tyrosine residues normally reside in the ICD of the rPTK (see FIG. 1 herein). Activation of the intracellular kinase domain of rPTKs appears to be mediated by receptor oligomerization which results from the conformational alteration of the ECD upon ligand binding thereto. See Ullrich and Schlessinger, supra.

Serine-threonine kinases have also been disclosed in the literature. While most of the known protein serine-threonine kinases are cytoplasmic proteins, a family of mammalian transmembrane receptors with serine-threonine kinase domains has recently been found. Members of this receptor family have been described as binding TGF-β's and activin. For reviews of serine-threonine kinases, see Sale, G., *Biochem. Soc. Transactions* 20: 664–670 (1992); ten Dijke et al., *Prog. in Growth Factor Res.* 5: 55–72 (1994); and Mathews, L., *Endoc. Rev.* 15(3): 310–325 (1994).

Various assays have been developed which measure tyrosine kinase activity. Some of these assays measure the ability of a tyrosine kinase enzyme to phosphorylate a synthetic substrate polypeptide. For example, an assay has been developed which measures growth factor-stimulated tyrosine kinase activity by measuring the ability of the kinase to catalyze the transfer of the γ-phosphate of ATP to a suitable acceptor substrate. See Pike, L., *Methods of Enzymology* 146: 353–362 (1987) and Hunter, *Journal of Biological Chemistry* 257(9): 4843–4848 (1982), for example. In this assay, the use of [γ-$^{32}$P]ATP permits the radioactive labeling of the phosphorylated substrate, which is a synthetic tyrosine-containing peptide. Others have described protein kinase assays wherein incorporation of $^{32}$P into a tyrosine kinase receptor, such as the EGF receptor (see Donato et al., *Cell Growth Differ.* 3: 259–268 [1992]), insulin receptor (see Kasuga et al., *Journal of Biological Chemistry* 257(17): 9891–9884 [1982] and Kasuga et al., *Methods in Enzymology* 109: 609–621 [1985]), and liver growth hormone receptor (see Wang et al., *Journal of Biological Chemistry* 267(24): 17390–17396 [1992]), is measured.

The discovery of anti-phosphotyrosine antibodies has provided a non-radioactive, alternative means for measuring phosphorylation of tyrosine residues. For example, White and Backer (*Methods in Enzymology* 201: 65–67 [1991]) mention polyclonal antibodies which selectively bind to phosphotyrosine and are considered to be useful for studying rPTKs. An anti-phosphotyrosine monoclonal antibody was used in one of the assays referred to in Madden et al. (*Anal Biochem* 199: 210–215 [1991]), which measured phosphatase activity toward the insulin receptor. Anti-phosphotyrosine antibodies were also used by Cleaveland et al., in their protein tyrosine kinase ELISA assay. See Cleaveland et al., *Analytical Biochemistry* 190: 249–253 (1990). The method of Cleaveland et al. utilizes purified high-activity oncogene tyrosine kinases, v-src and v-fps, and measures the ability of these tyrosine kinases to phosphorylate synthetic polymeric substrates which are coated on an ELISA microtiter plate. The phosphotyrosine produced by src-induced phosphorylation of the polymeric substrate is then quantitated by addition of an anti-phosphotyrosine antibody, the presence of which is detected using a second rabbit anti-mouse antibody which is linked to a reporter enzyme, horseradish peroxidase (HRPO). A similar ELISA assay has been developed by Lazaro et al., which is used for detection of a protein tyrosine kinase. See Lazaro et al., *Analytical Biochemistry* 192: 257–261 (1991). Like the assay of Cleaveland et al., this assay also measures the ability of a protein tyrosine kinase to phosphorylate a synthetic substrate which is bound to microELISA wells.

A direct way to assess specific activation of rPTKs is by analysis of receptor autophosphorylation. See, e.g., Hunter and Cooper *Ann Rev Biochem* 54: 897–930 (1985) and Ullrich and Schlessinger, *Cell* 61: 203–212 (1990). Using this direct approach, Knutson and Buck disclose assays for measuring autophosphorylation of the insulin receptor under in situ or in vitro conditions (*Archives of Biochemistry and Biophysics* 285(2): 197–204 [1991]). In the in situ assay, monolayer cultures of embryonic mouse 3T3-C2 fibroblasts (having the endogenous insulin receptor) are incubated with insulin in large cell culture dishes. Following incubation, the insulin receptor is extracted from the membranes. To achieve extraction of the insulin receptor, the cell monolayers are scraped into a buffer containing protease inhibitors and the cells are then disrupted in a homogenizer. The cellular homogenate is subsequently subjected to centrifugation for 60 min., and the pellet which forms is extracted into buffer containing detergent. Following a further centrifugation step, the supernatant (containing the insulin receptor) is incubated with an anti-insulin receptor antibody. Then, the receptor-antibody complex is incubated with protein A-agarose and unoccupied protein A sites are blocked with normal rabbit IgG. The agarose beads are then centrifuged, the supernatants aspirated and the pellets are re-suspended in buffer containing the radiolabelled anti-phosphotyrosine antibody. The amount of bound iodinated anti-phosphotyrosine antibody is consequently measured.

Klein and his colleagues discuss an assay for measuring insulin activation of the insulin receptor (Klein et al., *Diabetes* 42: 883–890 [1993]). In this assay, aliquots of a heterogeneous population of mononuclear blood cells (including T cells, B cells, macrophages etc) having the insulin receptor are exposed to insulin in centrifuge tubes. The cells are then lysed in detergent using a motordriven homogenizer and the lysates are concentrated two- to four-fold using vacuum centrifugation. Sometimes, the insulin receptor is also partially purified using wheat germ agglutin agarose. The supernatants which form following centrifugation, are then transferred to anti-insulin receptor-coated microtiter plates. Insulin (8.7 nM) as well as kinase and phosphatase inhibitors are present during receptor immobilization in order to optimize the percentage of receptors captured to the microtiter plates. Activation of the insulin receptor is then measured by transphosphorylation of the substrate Poly-Glu,Tyr with $^{32}$P labeled ATP. The supernatants are then spotted onto absorbent paper and the paper is washed with cold TCA to remove unbound $^{32}$P-ATP. Remaining $^{32}$P-labeled Poly-Glu,Tyr on the washed absorbent paper is subsequently counted by scintillation counting.

Hagino et al. were also interested in studying the insulin receptor in patients (Hagino et al., *Diabetes* 43: 274–280 [1994]). As a first step in the assay, Hagino et al. stimulate a primary cell suspension, which is not particularly homogeneous with respect to cell type. In particular, heparinized blood (1 ml washed twice with medium and resuspended in 1 ml of medium containing bovine serum albumin, BSA) is exposed to varying concentrations of insulin. The autophosphorylation reaction is stopped, the cells centrifuged for 30 min, the supernatant is discarded and the erythrocyte ghosts thus obtained are resuspended in buffer and centrifuged again. The pellet thereby obtained is adjusted to 500 µl and solubilized in detergent. The solubilized materials are then centrifuged and the resulting supernatant is subjected to sandwich ELISA (using anti-insulin receptor antibodies to capture the insulin receptor) to determine the extent of insulin receptor autophosphorylation.

King et al. in Life Sciences 53: 1465–1472 (1993) describe a colorimetric assay for examining inhibitors of the epidermal growth factor (EGF) receptor-associated tyrosine kinase in human intact epidermal A431 cells.

Several others have used an enzyme-conjugated form of the anti-phosphotyrosine antibody in Western blot analyses which measure receptor autophosphorylation. Briefly, Western blotting generally involves electrophoresing activated rPTK on polyacrylamide gel. The rPTK is then transferred to nitrocellulose and immunoblotted with the anti-phosphotyrosine antibody which is labelled to enable detection. See, for example, Wang, *Molecular and Cellular Biology* 5(12): 3640–3643 (1985); Glenney et al., *Journal of Immunological Methods* 109: 277–285 (1988); Kamps, *Methods in Enzymology* 201: 101–110 (1991); Kozma et al., *Methods in Enzymology* 201: 28–43 (1991); Holmes et al., *Science* 256: 1205–10 (1992); and Corfas et al., *PNAS, USA* 90: 1624–1628 (1993). However, with Western blot analysis, accurate quantitation can be very tedious. Furthermore, this technique tends to be time-consuming and generally does not allow high sample throughput.

It is an object of the instant invention to provide a sensitive, reliable assay that measures receptor protein tyrosine kinase (rPTK) autophosphorylation. The assay is desirably useful for qualitatively and quantitatively measuring kinase activation as well as facilitating identification and characterization of potential agonists and antagonists for a selected rPTK. It is a further object of the invention to provide an assay which enables ligand-receptor interactions to be studied for any selected rPTK.

This assay must have a capacity for high throughput, that is, the ability to reliably evaluate large numbers of samples in a relatively short period of time (e.g., in one day). The assay ideally does not use radioactive materials and is also amenable to automation.

It is a further object, in at least one embodiment of the invention, to provide a generic assay which enables a rPTK of interest to be studied, regardless of whether or not a receptor-specific capture agent having the desired characteristics is available. Furthermore, it is an object of the invention to provide an assay which substantially represents the activity of the tyrosine kinase receptor in situ. This is desirable insofar as it reduces the possibility that altered interactions between the receptor and the ligand may occur as a consequence of the receptor not being membrane-bound. Furthermore, if the receptor is a multimeric complex, this assay enables the correctly assembled receptor to be studied. It is an additional object to provide a method for measuring serine-threonine kinase phosphorylation, phosphorylation of intracellular kinases and phosphatase activity.

These and other objects will be apparent to the ordinary artisan upon consideration of the specification as a whole.

SUMMARY OF THE INVENTION

Accordingly, the invention provides an assay for measuring activation (i.e., autophosphorylation) of a tyrosine kinase receptor of interest.

The assay can be divided into two major stages, each of which is generally performed in separate assay plates. The first stage of the assay involves activating the receptor and is termed the kinase receptor activation (KIRA) stage of the assay. The second stage of the assay involves measuring receptor activation. Conveniently, this is achieved using an enzyme-linked immunosorbent assay (ELISA) to measure receptor activation.

The KIRA stage of the assay involves activating a tyrosine kinase receptor which is located in the cell membrane of an eukaryotic cell such that the extracellular domain of the receptor faces the external milieu of the cell, the transmembrane domain is located in the cell membrane and the kinase domain is located intracellularly. This stage of the overall assay involves steps (a) to (c) below:

(a) The first solid phase (e.g., a well of a first assay plate) is coated with a substantially homogeneous population of cells (usually a mammalian cell line) so that the cells adhere to the solid phase. Often, the cells are adherent and thereby adhere naturally to the first solid phase. In one embodiment of the invention, the cells have an endogenous tyrosine kinase receptor presented in the cell membrane as discussed above. In an alternative embodiment, the cells have been transformed with DNA encoding a tyrosine kinase receptor or a "receptor construct" defined further below, which DNA is expressed by the cells such that the receptor or receptor construct is suitably positioned in the cell membranes thereof.

The receptor construct comprises a fusion of a kinase receptor and a flag polypeptide. The flag polypeptide is recognized by the capture agent, often a capture antibody, in the ELISA part of the assay. Use of a receptor construct as disclosed herein is particularly advantageous since it provides a "generic" assay wherein autophosphorylation of any tyrosine kinase receptor can be measured, regardless of whether or not a receptor-specific capture agent having the required characteristics is available. Often, the tyrosine kinase receptor is a fusion protein comprising the ECD of a selected tyrosine kinase and the catalytic ICD (and possibly the transmembrane domain) of another well characterized tyrosine kinase (e.g., the Rse receptor).

(b) An analyte is then added to the wells having the adhering cells, such that the tyrosine kinase receptor is exposed to (or contacted with) the analyte. This assay enables identification of agonist and antagonist ligands for the tyrosine kinase receptor of interest. In order to detect the presence of an antagonist ligand which blocks binding and/or activation of the receptor by an agonist ligand, the adhering cells are exposed to the suspected antagonist ligand first and then to the agonist ligand (or to a mixture of the agonist and antagonist) so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands.

(c) Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. Thus, this assay provides a significant improvement over assays described by Knutson and Buck, supra, Klein et al., supra, and Hagino et al., supra, insofar as it is surprisingly unnecessary to concentrate the cell lysate prior to the ELISA. Furthermore, unlike the other assays, in the instant assay the cells can be lysed in lysis buffer using gentle agitation without the need for homogenizing, centrifuging or clarifying the cells. The cell lysate thus prepared is then ready to be subjected to the ELISA stage of the assay. It has been discovered that, surprisingly, the first assay plate can be stored at freezing temperatures (i.e., at about $-20°$ to $-70°$ C.) for significant periods of time (at least 6 months) before the ELISA stage of the assay. This is a significant finding insofar as the KIRA and ELISA stages of the assay can be performed on separate days.

The ELISA component of the assay comprises steps (d) to (h), described below.

(d) As a first step, the second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used.

(e) The cell lysate obtained in step (c) of the above-mentioned KIRA stage of the assay is exposed to, or contacted with, the adhering capture agent so that the receptor or receptor construct adheres to (or is captured in) the second solid phase. Unlike the assay of Klein et al., the instant assay does not require the ligand for the receptor as well as kinase inhibitors to be present to achieve suitable immobilization of the receptor or receptor construct to the second solid phase.

(f) A washing step is then carried out, so as to remove unbound cell lysate, leaving the captured receptor or receptor construct.

(g) The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule.

(h) Finally, binding of the anti-phosphotyrosine antibody to the captured receptor or receptor construct is measured, e.g., by a color change in the color reagent.

The invention also pertains to a Rse.flag reagent which is particularly useful for use in the KIRA ELISA assay. The Rse.flag reagent is a polypeptide comprising a fusion of a flag polypeptide (usually the gD flag described herein) to the carboxyl terminus of the intracellular domain of the Rse rPTK. Generally, the transmembrane domain of Rse and the extracellular domain of another rPTK of interest are also present in the fusion polypeptide reagent. The nucleic acid encoding this reagent and a cell transformed therewith are also claimed.

In yet a further aspect, the invention relates to a kit which can be used in the KIRA ELISA disclosed above which comprises an anti-flag polypeptide capture agent (e.g. a capture antibody) which is usually bound to the second solid phase as described herein. Thus, the kit generally provides an ELISA microtiter plate having an anti-flag polypeptide capture antibody adhering to a well thereof. optionally, the kit also provides an anti-phosphotyrosine antibody which is often labelled, or reagents for labelling the anti-phosphotyrosine antibody are supplied with the kit. Sometimes, a homogeneous population of cells which have been transformed with a receptor construct as described herein are also provided with the kit. The kit also suitably includes instructions for carrying out the KIRA ELISA.

BRIEF DESCRIPTION OF THE DRAWINGS

FIGS. 1A–1C are diagrammatic representations of Rse.gD (FIG. 1A), Receptor ECD/Rse.gD chimera (FIG. 1B) and a CHO cell transformed with the Receptor ECD/Rse.gD chimera (FIG. 1C).

FIGS. 2A–2C depict an alignment of the amino acid sequence (SEQ ID NO: 1) and nucleotide sequence (SEQ ID NO: 2) of Rse.gD. The residues of the signal sequence are indicated with an (*), the transmembrane domain of Rse is boxed and the ECD and ICD of Rse are also delineated. The residues of the gD flag sequence are underlined.

FIG. 3 is a flow diagram of an exemplary strategy for selecting a suitable capture agent for use in the assay.

FIG. 4 is a flow diagram of an exemplary strategy for selecting a transformed cell suitable for use in the assay, where the cell has a receptor construct with an amino-terminal flag polypeptide located in the cell membrane thereof.

FIG. 5 is a flow diagram of an exemplary strategy for selecting a transformed cell suitable for use in the assay, where the cell has a receptor construct with a carboxyl-terminal flag polypeptide located in the cell membrane thereof.

FIG. 6A–B is a flow chart and cartoon illustrating the KIRA ELISA assay for the HER2 receptor described in Example 1.

FIG. 7 depicts a p185$^{HER2}$/HRGβ1$_{177-244}$ KIRA ELISA standard curve obtained using the assay described in Example 1. To obtain the standard curve, MCF-7 cells (2×10$^5$) were stimulated with 3000, 1000, 333, 111, 37, 12, 4, or 0 pM HRGβ1$_{177-244}$, as determined by quantitative amino acid analysis (q.a.a.a.). Each calibrator concentration was run in triplicate. The values derived from 10 such standard curves were averaged (total n=30) and are presented as mean ABS$_{450/650}$±sd vs. HRGβ1$_{177-244}$ concentration.

FIG. 8 depicts heregulin specificity of p185$^{HER2}$/HRG KIRA ELISA of Example 1. In the assay, MCF-7 cells (2×10$^5$) were stimulated with either HRGβ1$_{177-244}$ (■) at 3000, 1000, 333, 111, 37, 12, 4 or 0 pM or IGF-1 (▲), EGF (□), VEGF (●) or insulin (♦) at 30000, 10000, 3333, 1111, 370, 120, 40 or 0 pM. For all concentrations of ligands, n=3 and data are presented as average ABS$_{450/650}$±sd vs. ligand concentration.

FIG. 9A–B is a flow chart and cartoon illustrating the KIRA ELISA assay for the Rse receptor described in Example 2.

FIG. 10 depicts a Rse KIRA ELISA standard curve obtained using the assay described in Example 2. To obtain the standard curve, CHO cells transformed with the Rse.gD construct were stiralated with 1:100, 1:200, 1:400, 1:800, 1:1600, 1:3200 or 0 diluted, anti-Rse agonist antibody. Each calibrator concentration was run in triplicate. The values are presented as mean ABS$_{450/650}$±sd vs. 1/dilution agonist antibody.

FIG. 11A–B is a flow chart and cartoon illustrating the KIRA ELISA assay for the trk receptors (i.e., trk A, trk B, and trk C) described in Example 3.

FIGS. 12A–12G depict an alignment of the amino acid acid sequence is (SEQ ID NO: 3) and nucleotide sequence (SEQ ID NO: 4) of gD.trk A used in the assay described in Example 3. The residues of the signal sequence are indicated with an (*), the residues of the gD flag sequence are underlined, the residues of the transmembrane domain of trk A are in bold and the ECD and ICD thereof are also delineated.

FIGS. 13A–13G depict an alignment of the amino acid sequence (SEQ ID NO: 5) and nucleotide sequence (SEQ ID NO: 6) of gD.trk B used in the assay described in Example 3. The residues of the signal sequence are indicated with an (*), the residues of the gD flag sequence are underlined, the residues of the transmembrane domain of trk B are in bold and the ECD and ICD thereof are also delineated.

FIGS. 14A–14G depict an alignment of the amino acid sequence (SEQ ID NO: 7) and nucleotide sequence (SEQ ID NO: 8) of gD.trk C used in the assay described in Example 3. The residues of the signal sequence are indicated with an (*), the residues of the gD flag sequence are underlined, the residues of the transmembrane domain of trk C are in bold and the ECD and ICD thereof are also delineated.

FIGS. 15A–15C depict standard curves for trk A, B and C, respectively, which were obtained using the assay described in Example 3. To obtain the standard curves, CHO cells trans formed with the gD.trk constructs were stimulated with 3000, 1000, 333, 111, 37, 12, 4 or 0 pM of ligand, i.e. nerve growth factor (NGF, ■), neurotrophin 3 (NT3, ●) or neurotrophin 5 (NT5, ▲). The values are presented as mean ABS$_{450/650}$±sd vs. ligand concentration.

FIGS. 16A–16Z-5 depict the nucleotide sequence (SEQ ID NO: 9) of the pSVI17.ID.LL expression vector used for expression of Rse.gD in Example 2.

FIG. 17 is a diagrammatic representation of the MPL/Rse.gD chimeric receptor described in Example 4.

FIG. 18A–B is a flow chart and cartoon illustrating the KIRA ELISA for the MPL/Rse.gD chimeric receptor described in Example 4.

DETAILED DESCRIPTION OF THE PREFERRED EMBODIMENTS

I. Abbreviations and Definitions

Figure 11B:
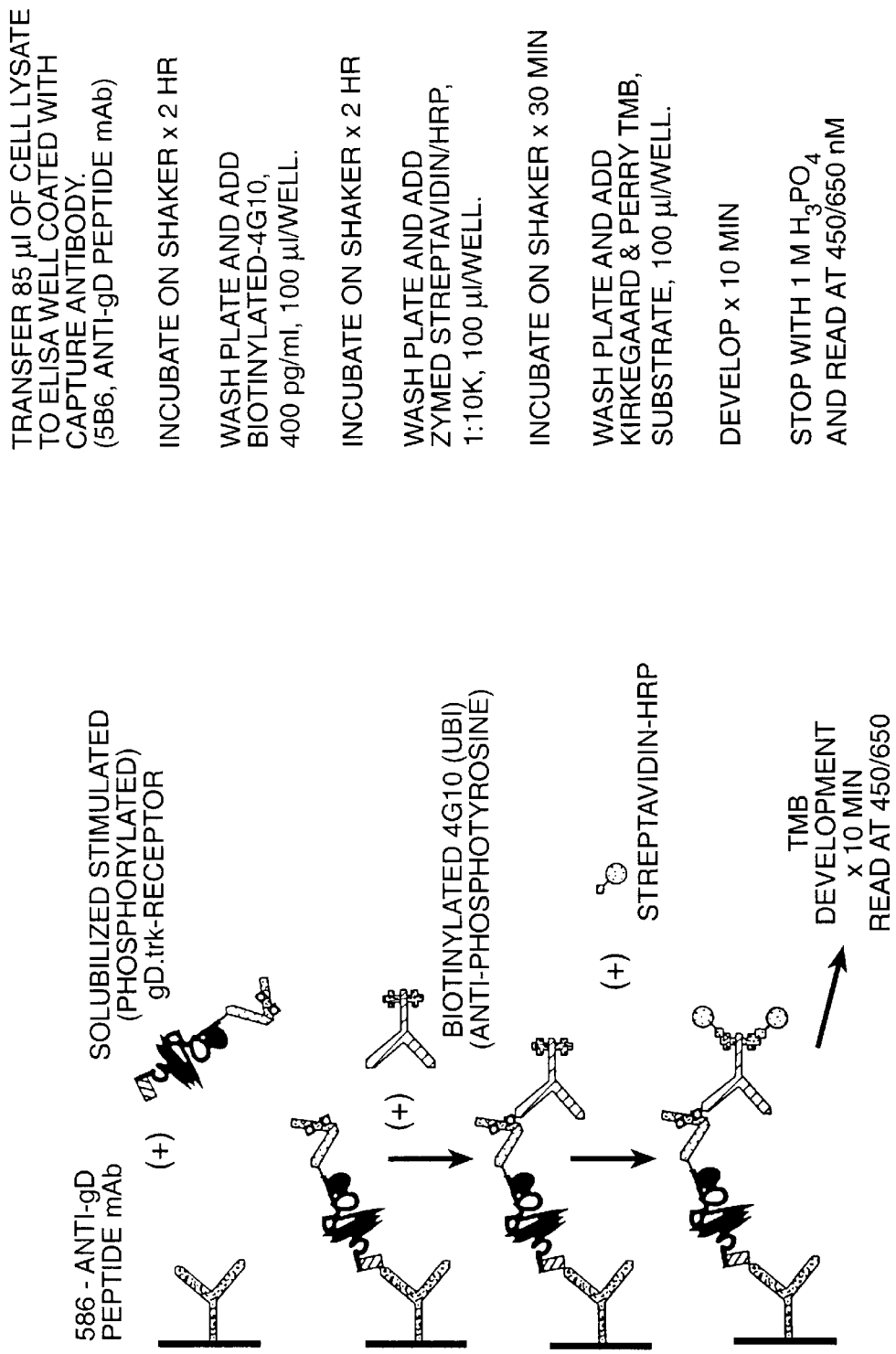

"rPTK" means a receptor protein tyrosine kinase.

"ECD", "TM domain" and "ICD" refer to the extracellular domain, transmembrane domain and intracellular domain of a rPTK, respectively.

"Kinase Receptor Activation" or "KIRA" when used throughout this application refers to the first stage of the instantly claimed assay wherein a cell-bound rPTK is exposed to a potential agonist/antagonist ligand which may (or may not) induce phosphorylation of tyrosine residues in the intracellular domain of the rPTK. The KIRA is generally carried out in the "first assay plate" as defined herein.

"Enzyme-Linked Immunosorbent Assay" or "ELISA" refers to the second stage of the instantly claimed assay and involves measuring tyrosine phosphorylation of the rPTK. The ELISA is normally carried out in the "second assay plate" as disclosed in this application. The ELISA is a "sandwich ELISA" insofar as it involves capturing the rPTK or receptor construct to the second solid phase (usually the well of an ELISA microtiter plate). ELISA assays generally involve the preparation of enzyme-antibody conjugates. The conjugated enzyme cleaves a substrate to generate a colored reaction product that can be detected spectrophotometrically. In this assay, the absorbance of the colored solution in individual microtite wells is proportional to the amount of phosphotyrosines. A review of ELISA is found in *Current Protocols in Molecular Biology*, Vol. 2, chapter 11 (1991). While the term "ELISA" is used to describe the second stage of the instant assay, it is only a preferred embodiment of the invention, since, as disclosed herein, techniques other than enzymatic detection are available for measuring binding of the anti-phosphotyrosine antibody to the activated receptor.

The terms "receptor", "kinase receptor", "tyrosine kinase", "tyrosine kinase receptor", "receptor protein tyrosine kinase" and "rPTK" are used interchangeably herein and refer to a protein having at least one phosphate accepting phenolic group. The protein is usually a receptor insofar as it has a ligand-binding ECD, TM domain and ICD. The ICD usually comprises a catalytic kinase domain and has one or more phosphate accepting tyrosine residues. See FIGS. 1A and 1B, for example. Examples of tyrosine kinase receptors include the insulin receptor, insulin related receptor, epidermal growth factor receptor (EGF-R), platelet-derived growth factor receptors A and B (PDGF-R-A and PDGF-R-B), insulin-like growth factor 1 receptor (IGF-1-R), macrophage colony-stimulating factor receptor (M-CSF-R), HER2/neu/c-erbB-2 receptor, HER3/c-erbB-3 receptor, Xmrk receptor, IRR receptor, fibroblast growth factor (FGF) receptors bek and flg, c-kit receptor, Flk/kDR receptor, Rse receptor, the Eph, Elk, Eck, Eek, Erk, Cek4/Mek4/HEK and Cek5 receptors, Axl receptor, hepatocyte growth factor receptor (HGF-R), Flt1 VEGF receptor, SAL-S1 receptor, HpTK 5 receptor, trkA receptor, trkB receptor, and trkC receptor. See, for example, Ullrich and Schlessinger *Cell* 81: 203–212 (1990); Fantl et al., *Annu. Rev. Biochem*, 62: 453–481 (1993); Mark et al., *Journal of Biological Chemistry* 269(14): 10720–10728 (1994); and WO 93/15201.

The terms mentioned above encompass chimeric "receptor" molecules which comprise at least the extracellular domain of a selected tyrosine kinase and the intracellular domain, and optionally, the transmembrane domain of another tyrosine kinase. Of course, the tyrosine kinase of interest can provide the transmembrane domain and/or intracellular domain. The terms also encompass amino acid sequence variants and covalent derivatives of the various rPTKs provided they still display tyrosine kinase phosphorylation activity in the KIRA ELISA. Therefore, the variants will general have conservative amino acid alterations. The individual domains of the tyrosine kinase can be delineated based on sequence homology to known tyrosine kinases and hydrophobicity plots. For example, the hydrophobic transmembrane domain can be readily determined and the ECD and ICD are usually amino-terminal and carboxyl terminal to the transmembrane domain, respectively. Conveniently, the transmembrane domain and ICD of the Rse receptor can be fused to the ECD of a tyrosine kinase of interest, thereby forming a chimeric receptor which is encompassed by the terms denoting a receptor as mentioned above.

In the preferred embodiment, the rPTK is selected from the group consisting of HER2 receptor (Ullrich and Schlessinger, sudra), Rse receptor (Mark et al., supra and SEQ ID NO: 1), trk A receptor (SEQ ID NO: 3), trk B receptor (SEQ ID NO: 5) and trk C receptor (SEQ ID NO: 7).

By "autophosphorylation" is meant activation of the catalytic kinase domain of the rPTK, whereby at least one intrinsic tyrosine residue is phosphorylated. Generally, autophosphorylation will result when an agonist molecule binds to the extracellular domain of the kinase receptor. Without being limited to any particular mechanism of action, it is thought that binding of the agonist molecule may result in oligomerization of the kinase receptor which causes activation of the catalytic kinase domain.

By "solid phase" is meant a non-aqueous matrix to which the cells (in the KIRA stage of the assay) or the capture agent (in the ELISA stage of the assay) can adhere. Usually, the solid phase comprises the well of an assay plate but the invention is by no means limited to this embodiment. For example, the solid phase can comprise a discontinuous solid phase of discrete particles. The particles can be porous and formed from a number of different materials, e.g., polysaccharides (e.g. agarose), polyacrylamides, polystyrene, polyvinyl alcohol, silicones and glasses. For examples of suitable particulate solid phases, see U.S. Pat. No. 4,275,149.

By "well" is meant a recess or holding space in which an aqueous sample can be placed. The well is provided in an "assay plate". The invention usually employs a "first assay plate" which is formed from a material (e.g. polystyrene) which optimizes adherence of cells (having the receptor or receptor construct) thereto. Generally, the individual wells of the first assay plate will have a high surface area to volume ratio and therefore a suitable shape is a flat bottom well (where the cells are adherent). The "second assay plate" is generally formed from a material (e.g. polystyrene) which optimizes adherence of the capture agent thereto. The second assay plate may have the same general construction and/or characteristics as the first assay plate. However, separate plates are used for the KIRA stage of the assay and the ELISA stage of the assay.

In the preferred embodiment of the invention, both the first assay plate and the second assay plate are "microtiter" plates. The term "microtiter" plate when used herein refers to an assay plate having between about 30 to 200 individual wells, usually 96 wells. Often, the individual wells of the microtiter plate will hold a maximum volume of about 250 $\mu$l. Conveniently, the first assay plate is a 96 well polystyrene or plastic, cell culture microtiter plate (such as that sold by Becton Dickinson Labware, Lincoln Park, N.J.), which allows for automation. Often, about 50 $\mu$l to 300 $\mu$l, more preferably 100 $\mu$l to 200 $\mu$l, of an aqueous sample comprising cell culture media with the cells suspended therein will be added to each well of the first assay plate in the KIRA stage of the assay. It is desirable to seed between about $1\times10^4$ to $3\times10^5$ cells per well. More preferably, $5\times10^4$ to $1\times10^5$ cells per well are seeded. Usually, the second assay plate will comprise a polystyrene microtiter ELISA plate such as that sold by Nunc Maxisorp, Inter Med, Denmark.

The term "homogeneous population of cells" refers to a substantially homogeneous population of cells wherein at least about 80%, and preferably about 90%, of the cells in the population are of the same cell type. Therefore, it is convenient to use a cell line. The cell line is a eukaryotic cell line, normally an animal cell line and desirably a mammalian cell line.

The cells have, or are transformed to produce, the selected receptor or a receptor construct. For example, where the kinase receptor is known to be present in a certain cell line (e.g., the HER2 receptor in the MCF-7 cell line) no transformation step is required. conversely, it may be necessary to transform a cell with a nucleic acid encoding the receptor, where the cell does not make the receptor, or does not have suitable numbers of the receptor in the cell membrane thereof. Accordingly, the cell is transformed with a nucleic acid encoding the receptor (or receptor construct) and the nucleic acid is expressed so that the ECD of the receptor faces the external milieu of the cell, the transmembrane domain is located in the cell membrane and the kinase domain is located intracellularly.

Where the assay relies on activating the endogenous rPTK, a cell line is selected which is known to produce the rPTK of interest, provided sufficient levels of the rPTK are present in the cell membrane thereof to enable detection. As a general proposition, a minimum number of about $1\times10^4$ receptors/cell is required. For example, the MCF-7 cell line (ATCC-HTB 22) which produces the HER2 receptor was shown to be useful in the assay. There are $5\times10^4$ HER2 receptors/MCF-7 cell. Examples of other cell lines and their respective rPTKs include, embryonic mouse 3T3-C2 fibroblast cell line and the insulin receptor, and Hep 3B (ATCC # HB 8064) cell line and the Rse receptor. However, the degree of expression of the rPTK nucleic acid in the cell line is not so high that it results in constitutive phosphorylation of the rPTK. For example, the SK-BR-3 cell line (ATCC HTB30), which has $3\times10^6$ HER2 receptors/cell, was found to be unsuitable for use in the assay disclosed herein. Therefore, it may be useful to use a cell line which has less than about $3\times10^6$ receptors/cell, depending on the type of receptor. The number of receptors/cell can be measured using Scatchard analysis, for example (Scatchard, *Ann, NY Acad. Sci.* 51: 660–672 [1949]; and Goodwin et al., *Cell* 73: 447–456 [1993]). However, selection of a cell line having a suitable number of receptors/cell is possible using the techniques described herein.

The term "adherent" when used herein to describe the cell, refers to a cell which naturally adheres to the first solid phase (often the well of the first assay plate), thereby forming a fairly uniform coating of the cells on the inside surface of the well. The uniform coating of cells generally forms following incubation of the cells in the wells of the first assay plate for about 8–16 hours. After incubation, non-adhering cells and cell culture medium are decanted off the first assay plate. Incubation is usually carried out at a temperature which is optimal for cell growth, i.e, about 37° C. Examples of adherent cell lines include CHO cells (Urlaub and Chasin, *Proc. Natl. Acad. Sci USA* 77: 4216 [1980]), MCF-7 cells (ATCC HB 22), 293 cells (Graham et al., *J. Gen Virol*. 36: 59 [1977]), Swiss albino 3T3 fibroblast cell line (ATCC No. CCL 92) and U937 macrophage cell line (ATCC No. CRL 1593).

A "flag polypeptide" comprises a short polypeptide which has enough residues to provide an epitope (preferably a linear epitope) against which a "capture agent" thereagainst can be made, yet is short enough such that it does not interfere with activity of the rPTK. The flag polypeptide is also sufficiently unique so that the capture agent thereagainst does not bind to other reagents in the assay. Selection of a "unique" flag polypeptide sequence can be accomplished by comparing the sequence of a proposed flag polypeptide against other known sequences in Genbank or EMBL, for example. Suitable flag polypeptides generally have at least 6 amino acid residues and usually between about 8–80 amino acid residues (preferably between about 9–30 amino acid residues).

By "receptor construct" is meant a polypeptide which comprises a fusion of a kinase receptor and a flag polypeptide as defined above. The flag polypeptide is provided at a location in the receptor construct such that: a) the flag polypeptide does not interfere with ligand binding to the receptor; b) the flag polypeptide does not interfere with autophosphorylation of the receptor and c) the flag polypeptide is presented in a suitable configuration so that it can bind to the capture agent in the ELISA stage of the assay. Often, the polypeptide flag will be present at the N-terminus of the receptor construct. See, for example, Example 3 which refers to the gD.trk constructs. Alternatively, the flag polypeptide may be present at the C-terminus of the receptor construct. See, for example, Example 2 which refers to the Rse.gD construct. See also FIGS. 1A–1C. The Rse construct disclosed herein is particularly useful, since the ICD (and optionally the transmembrane domain) thereof can be fused to the ECD of a kinase receptor of interest, thereby obviating the need to establish where the flag polypeptide should be located with respect to the kinase receptor of interest.

"Rse.gD" refers to a receptor construct which is the Rse receptor protein tyrosine kinase with the Herpes Simplex virus glycoprotein D (gD) flag polypeptide fused to the COOH-terminus thereof.

"Rse.flag reagent" refers to a polypeptide which comprises the ICD of the Rse receptor fused at its COOH-terminus to a flag polypeptide (normally the gD flag polypeptide). Sometimes, the TM domain of Rse and the ECD of a rPTK of interest will also be present in the Rse.gD. reagent. "Receptor ECD/Rse.gD Chimera" refers to a fusion of the ECD of a rPTK of interest to the TM and ICD domains of Rse which are fused COOH-terminally to the gD flag polypeptide.

"gD.trkA", "gD.trkB" and "gD.trkC" refer to each of the trk receptors (A–C) having the gD flag polypeptide fused to the amino-termini thereof.

By "capture agent" is meant a compound or agent which is able to adhere to the second solid phase, as herein defined, and which is selective for a rPTK or receptor construct.

Thus, the capture agent captures the receptor or receptor construct to the wells of the second assay plate. Usually, the capture agent binds selectively to the flag polypeptide which has been fused to the receptor of interest. Binding of the capture agent is not affected by the presence or absence of ligand bound to the receptor and does not induce receptor activation upon capture. Furthermore, the capture agent does not sterically block access to the phosphorylated tyrosine(s) by the anti-phosphotyrosine antibody. Means for selecting suitable capture agents are described herein. Generally, the capture agent will comprise an antibody (e.g., an affinity purified polyclonal antibody or a monoclonal antibody), but other selective agents, such as streptavidin which binds selectively to the "strep-tag" polypeptide can also be used (see Schmidt et al., *Protein Engineering* 6(1): 109–122 [1993]) Streptavidin can be purchased commercially from Zymed Laboratories, S. San Francisco, Calif., for example. Alternatively, the capture agent can comprise protein A (which binds specifically to immunoglobulins). In this embodiment of the invention, the activated receptor or receptor-construct present in the cell lysate is incubated with an antibody which binds specifically thereto, thereby forming a receptor-antibody complex. This complex can be captured by protein A by virtue of its specific binding to the antibody present in the complex. Protein A can be purchased commercially from Pharmacia Biotech, Inc., Piscataway, N.J., for example. A strategy for selecting a suitable capture agent is depicted in FIG. 3 and will be described in more detail later herein.

In the most preferred embodiment, the capture agent is a monoclonal antibody which binds specifically to a flag polypeptide (which is present in the receptor construct). Examples of suitable flag polypeptides and their respective capture antibodies include the flu HA flag and its antibody 12CA5, (Field et al., *Mol. Cell. Biol*. 8: 2159–2165 [1988]); the c-myc flag and the 8F9, 3C7, 6E10, G4, B7 and 9E10 antibodies thereto (Evan et al., *Molecular and Cellular Biology* 5(12): 3610–3616 [1985]); as well as the Herpes Simplex virus glycoprotein D (gD) flag and the 5B6 antibody thereto (Paborsky et al., *Protein Engineering* 3(6): 547–553 [1990] and Mark et al., *Journal of Biological Chemistry* 269(14): 10720–10728 [1994]). Other flag polypeptides have been disclosed. Examples include the Flag-peptide (Hopp et al., *BioTechnology* 6: 1204–1210 [1988]); the KT3 epitope peptide (Martin et al., *Science* 255: 192–194 [1992]); an α-tubulin epitope peptide (Skinner et al., *J. Biol. Chem* 266(22): 14163–14166 [1991]); and the T7 gene 10 protein peptide tag (Lutz-Freyermuth et al., *Proc. Natl. Acad. Sci. USA* 87: 6393–6397 [1990]). Once the flag polypeptide has been selected as discussed above, a capture antibody thereto can be generated using the techniques disclosed herein.

The term "analyte" refers to a compound or composition to be studied, usually to investigate its ability to activate (or prevent activation of) the tyrosine kinase receptor of interest. The analyte can comprise a bodily fluid (such as plasma or amniotic fluid) or a composition known to contain, or suspected of containing, a ligand for the tyrosine kinase receptor. The analyte can also comprise a cell which has a ligand to the rPTK of interest.

"Ligand" when used herein refers to a molecule which is able to bind to the ECD of the tyrosine kinase of interest or to a known agonist for the tyrosine kinase of interest. The ligand will usually be an agonist or antagonist for the tyrosine kinase.

By "agonist" is meant a molecule which is able activate the intracellular kinase domain of the tyrosine kinase upon binding to the ECD. Often, the agonist will comprise a growth factor (i.e., a polypeptide that is able to stimulate cell division). Exemplary growth factors include heregulin (ERG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), fibroblast growth factor (FGF), transforming growth factors alpha and beta (TGF-α and TGF-β), hepatocyte growth factor (HGF), and nerve growth factor (NGF). Alternatively, the agonist can be an antibody against the rPTK (see, e.g., Yarden, *Proc. Natl. Acad. Sci., USA* 87: 2569–2573 [1990]). However, other non-protein agonists such as small organic molecules are also encompassed by the invention.

By "antagonist" is meant a molecule which blocks agonist action. Usually, the antagonist will either: (a) bind to the rPTK and thereby block binding and/or activation of the rPTK by an agonist thereto (the antagonist may bind to the ECD of the rPTK, but this is not necessarily the case) or (b) bind to the agonist and thus prevent activation of the rPTK by the agonist. This assay facilitates the detection of both types of antagonist. The antagonist may, for example, comprise a peptide fragment comprising the receptor binding domain of the endogenous agonist ligand for the receptor. The antagonist may also be an antibody which is directed against the ECD of the rPTK, or against a known agonist for the rPTK. However, other non-protein molecules are also encompassed by this term.

The term "antibody" is used in the broadest sense and specifically covers monoclonal antibodies and antibody compositions with polyepitopic specificity (i.e. polyclonal antibodies). The polyclonal antibodies are preferably "affinity purified" antibodies. The term "affinity purified" means that the antibodies have been purified using the antigen (e.g. the rPTK or fragment thereof or the flag polypeptide) to selectively purify the polyclonal antibodies. Affinity purification can be achieved by immobilizing the antigen on an affinity column (e.g. an agarose column) and passing the polyclonal antibodies through the column. The affinity purified antibodies can be subsequently eluted from the column by changing the elution conditions or by adding a chaotropic agent, for example. For a review of affinity purification techniques with respect to antibodies, see *Current Protocols in Immunology*, Ed. Coligen et al., Wiley publishers, Vols. 1 and 2, for example.

The term "monoclonal antibody" as used herein refers to an antibody obtained from a population of substantially homogeneous antibodies. i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of a selected antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. U.S. Pat. No. 4,816,567 and Mage & Lamoyi, in *Monoclonal Antibody Production Techniques and Applications*, pp.79–97 (Marcel Dekker, Inc., New York (1987)].

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256: 495 (1975), or may be made by recombinant DNA methods (U.S. Pat. No. 4,816,567). The "monoclonal antibodies" may can also be isolated from phage antibody libraries using the techniques described in Clackson et al., *Nature*, 352: 624–628 (1991) and Marks et al., *J. Mol. Biol.*, 222: 581–597 (1991), for example.

The term "anti-phosphotyrosine antibody" refers to a molecule, usually an antibody, which binds selectively to phosphorylated tyrosine residues in the kinase domain of a rPTK. The antibody can be polyclonal, but is desirably a monoclonal antibody. Anti-phosphotyrosine polyclonal antibodies can be made using the techniques disclosed in White and Backer, *Methods in Enzymology* 201: 65–67 [1991] and monoclonal anti-phosphotyrosine antibodies can be obtained commercially from Upstate Biologicals, Inc. (UBI, Lake Placid, N.Y.), for example.

The word "label" when used herein refers to a detectable compound or composition which is conjugated directly or indirectly with a molecule (such as the anti-phosphotyrosine antibody). The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or anti-phosphotyrosine antibody) is removed therefrom. To reduce background noise, it is convenient to include a detergent (e.g. Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) may be required.

By "block buffer" is meant an aqueous, pH buffered solution containing at least one blocking compound which is able to bind to exposed surfaces of the second solid phase which are not coated with capture agent. The blocking compound is normally a protein such as bovine serum albumin (BSA), gelatin, casein or milk powder and does not cross-react with any of the reagents in the assay (e.g., the anti-phosphotyrosine antibodies and detection reagents). The block buffer is generally provided at a pH between about 7 to 7.5 and suitable buffering agents include phosphate and TRIS.

By "lysis buffer" is meant an aqueous, pH buffered solution comprising a solubilizing detergent, one or more protease inhibitors and at least one phosphatase inhibitor (such as sodium orthovanadate). The term "solubilizing detergent" refers to a water miscible, non-ionic detergent which lyses cell membranes of eukaryotic cells but does not denature or activate the receptor or receptor construct. Examples of suitable non-ionic detergents include Triton-X 100, Tween 20, CHAPS and Nonidet P-40 (NP40) available from Calbiochem, La Jolla, Calif., for example. Many other non-ionic detergents are available in the art. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin and benzamidine. Preservatives (e.g., thimerosal) and one or more compounds which maintain the isotonicity of the solution (e.g., sodium chloride [Nacl] or sucrose) and a buffer (e.g., Tris or PBS) are usually also present. Generally, the pH of the lysis buffer is in the range about 7 to 7.5.

Usually, following addition of the lysis buffer to the first assay plate, the first assay plate is "gently agitated" and this expression refers to the act of physically shaking the first assay plate (normally using a circular motion) at a substantially low velocity. Gentle agitation does not involve mechanically disrupting the cells (e.g. by homogenizing or centrifuging the cells). Exemplary shaking velocities are in the order of 200 to 500 rpm, preferably 300 to 400 rpm in a Bellco orbital shaker, for example.

II. Modes for Practicing the Invention

1. Kinase Receptor Activation—KIRA

The first stage of the assay involves phosphorylation of the kinase domain of a kinase receptor, wherein the receptor is present in the cell membrane of a eukaryotic cell. The receptor may be an endogenous receptor or nucleic acid encoding the receptor may be transformed into the cell. In one embodiment of the invention, nucleic acid encoding a receptor construct is transformed into the cell. Exemplary techniques for transforming the cell with either the receptor or the receptor construct nucleic acid follow.

A. Transformation of the cells

The instant invention provides a substantial improvement over soluble kinase receptor assays insofar as it is considered to more accurately reflect the activity of the receptor in situ. It has been discovered that it is possible to transform eukaryotic cells with a receptor construct (comprising the kinase receptor and either an amino- or carboxyl-terminal flag polypeptide) so that the receptor construct assembles itself appropriately in the cell membrane and still retains tyrosine kinase activity which can be detected in the ELISA stage of the assay. This provides a generic assay for measuring tyrosine kinase activity of any tyrosine kinase of interest.

If a suitable capture agent as described herein is available for a selected rPTK, cells can be transformed with the nucleic acid encoding the receptor alone, without the flag polypeptide. Alternatively, if cells are available which produce the receptor (e.g., MCF-7 cells which produce the HER2 receptor), it is not necessary to transform the cells for use in the assay.

In order to transform the cells with the nucleic acid encoding the rPTK or receptor construct, nucleic acid encoding the rPTK and, optionally, the flag polypeptide, is isolated. This can be achieved by screening a cDNA or genomic library known to contain the DNA encoding the rPTK or flag polypeptide of interest with a selected labelled probe (e.g., an antibody or oligonucleotide- probe) for the rPTK or flag polypeptide, using standard procedures as described in chapters 10–12 of Sambrook et al., *Molecular Cloning: A Laboratory Manual* (New York: Cold Spring Harbor Laboratory Press, 1989), for example. Alternatively, the nucleic acid encoding the flag polypeptide can be made synthetically using an oligo-synthesizing machine (Applied Biosystems, CA). An alternative means to isolate the nucleic acid encoding the rPTK or flag polypeptide is to use PCR methodology as described in section 14 of Sambrook et al., supra. Isolation of only the ECD of the rPTK of interest is required, since this nucleic acid can be fused to the nucleic acid encoding the TM and ICD of the Rse-flag polypeptide construct disclosed herein. See FIGS. 1A–1C and SEQ ID NOS: 1 and 2. If necessary however, conventional primer extension procedures as described in section 7.79 of Sambrook et al., supra, can be used to detect precursors and processing intermediates of mRNA that may not have been reverse-transcribed into cDNA.

A preferred method of practicing this invention is to use carefully selected oligonucleotide sequences to screen cDNA libraries from various tissues, preferably mammalian cell lines having the rPTK of interest. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

In order to provide nucleic acid encoding a receptor construct, nucleic acid encoding the rPTK is fused at its 3' end to nucleic acid encoding the N-terminus of the flag polypeptide. Alternatively, the nucleic acid encoding the rPTK will be fused at its 5' end to nucleic acid encoding the carboxyl terminus of the flag polypeptide. Thus, the flag polypeptide is provided at either the carboxyl- or amino-terminus of the receptor construct. Examples of suitable flag polypeptides are provided above. Selection of other suitable flag polypeptides is possible using the techniques described herein.

In order to generate fusions between the Rse.flag reagent and a rPTK of interest, the nucleic acid encoding the ECD of the rPTK of interest is fused at its 3' end to the nucleic acid encoding the amino terminus of the Rse.flag reagent.

The nucleic acid (e.g., cDNA or genomic DNA) encoding the rPTK or receptor construct is then inserted into a replicable vector for further cloning (amplification of the DNA) or for expression. Many vectors are available to the skilled practitioner but must be compatible with the cell which is to be used in the assay. The vector will have vector components the presence of which will depend on various factors. Such components include, for example, a signal sequence, an origin of replication, one or more marker genes, an enhancer element, a promoter, and a transcription termination sequence. Selection of these vector components shall be described below.

Incorporation of a signal sequence into the expression vector is required since the rPTK or receptor construct must be transported to the cell membrane where it is positioned such that the ECD faces the external milieu of the cell. Therefore, a signal sequence suitable for positioning the rPTK or receptor construct in such a manner is used. The signal sequence is generally a component of the vector, or it may be a part of the rPTK or receptor construct DNA that is inserted into the vector. If a heterologous signal sequence is used, it is from those that are recognized and processed (i.e., cleaved by a signal peptidase) by the host cell.

For yeast secretion the native signal sequence may be substituted by, e.g., the yeast invertase leader, alpha factor leader (including Saccharomyces and Kluyveromyces α-factor leaders, the latter described in U.S. Pat. No. 5,010.182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cells expression of the DNA encoding the native signal sequence (e.g., the rPTK pre-sequence that normally directs secretion of rPTK from mammalian cells in vivo) is satisfactory, although other mammalian signal sequences may be suitable, such as signal sequences from other animal rPTKs, and signal sequences from secreted polypeptides of the same or related species, as well as viral secretory leaders, for example, the herpes simplex gD signal.

The DNA for such precursor region is ligated in reading frame to DNA encoding the rPTK or receptor construct.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. The $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transformed into another organism for expression. For example, a vector is cloned in *E. coli* and then the same vector is transformed into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transformation of Bacillus with this vector results in homologous recombination with the genome and insertion of rPTK or receptor construct DNA. However, the recovery of genomic DNA encoding the rPTK or receptor construct is more complex than that of an exogenously replicated vector because restriction enzyme digestion is required to excise the rPTK or receptor construct DNA.

Expression and cloning vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene express the DNA encoding a protein conferring drug resistance and thus survive the selection regimen. Examples of such dominant selection use the drugs neomycin (Southern er al., *J. Molec. Appl. Genet.* 1: 327 [1982]), mycophenolic acid (Mulligan et al., *Science* 209: 1422 [1980]) or hygromycin (Sugden et al., *Mol. Cell. Biol.* 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the rPTK or receptor construct nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the rPTK or receptor construct. Amplification is the process by which genes in greater demand for the production of a protein critical for growth are reiterated in tandem within the chromosomes of successive generations of recombinant cells. Increased quantities of rPTK or receptor construct are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasmn, *Proc. Natl. Acad. Sci. USA* 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the rPTK or receptor construct. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the rPTK or receptor construct, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282: 39 [1979]; Kingsman et al., *Gene* 7: 141 [1979]; or Tschemper et al., *Gene* 10: 157 [1980]). The trp1 gene provides a selection marker for a mutant strain of yeast lacking the ability to grow in tryptophan, for example, ATCC No. 44076 or PEP4-1 (Jones, *Genetics* 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of Kluyveromyces yeasts. Bianchi et al., *Curr. Genet.* 12: 185 (1987). More recently, an expression system for large-scale production of recombinant calf chymosin was reported for *K. lactis*. Van den Berg, *Bio/Technology* 8: 135 (1990). Stable multi-copy expression vectors for secretion of mature recombinant human serum albumin by industrial strains of Kluyveromyces have also been disclosed. Fleer et al., *Bio/Technology* 9: 968–975 (1991).

Expression and cloning vectors usually contain a promoter that is recognized by the host organism and is operably linked to the rPTK or receptor construct nucleic acid. Promoters are untranslated sequences located upstream (5') to the start codon of a structural gene (generally within about 100 to 1000 bp) that control the transcription and translation of particular nucleic acid sequence, such as the rPTK nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to rPTK or receptor construct-encoding DNA by removing the promoter from the source DNA by restriction enzyme digestion and inserting the isolated promoter sequence into the vector. Both the native rPTK promoter sequence and many heterologous promoters may be used to direct amplification and/or expression of the rPTK or receptor construct DNA. The promoter will be one which results in the accumulation of suitable numbers of receptor or receptor construct in the cell membrane of the transformed cell (i.e. so that autophosphorylation of the receptor is detectable in the ELISA but constitutive phosphorylation does not occur). Selection of a suitable promoter to achieve this is possible following the guidelines herein for selecting cells for use in the KIRA ELISA.

Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255: 2073 [1980]) or other glycolytic enzymes (Hess et al., *J. Adv. Enzyme Reg.*, 7: 149 [1968]; and Holland, *Biochemistry* 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

rPTK or receptor construct transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the rPTK or receptor construct sequence, provided such promoters are compatible with the host cell systems.

The early and late promoters of the SV40 virus are conveniently obtained as an SV40 restriction fragment that also contains the SV40 viral origin of replication. Fiers et al., *Nature* 273: 113 (1978); Mulligan and Berg, *Science* 209: 1422–1427 (1980); Pavlakis et al., *Proc. Natl. Acad. Sci. USA* 78: 7398–7402 (1981). The immediate early promoter of the human cytomegalovirus is conveniently obtained as a HindIII E restriction fragment. Greenaway et al., *Gene* 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295: 503–508 (1982) on expressing cDNA encoding immune interferon in monkey cells; Reyes et al., *Nature* 297: 598–601 (1982) on expression of human β-interferon cDNA in mouse cells under the control of a thymidine kinase promoter from herpes simplex virus; Canaani and Berg, *Proc. Natl. Acad. Sci. USA* 79: 5166–5170 (1982) on expression of the human interferon β1 gene in cultured mouse and rabbit cells; and Gorman et al., *Proc. Natl. Acad. Sci. USA* 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the rPTK or receptor construct by higher eukaryotes may be increased, if increased numbers of the rPTK or receptor construct per cell are required to facilitate detection in the ELISA stage of the assay. This may be achieved by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78: 993 [1981]) and 3' (Lusky et al., *Mol. Cell Bio.* 3: 1108 [1983]) to the transcription unit, within an intron (Banerji et al., *Cell* 33: 729 [1983]), as well as within the coding sequence itself (Osborne et al., *Mol. Cell Bio.* 4: 1293 [1984]). Many enhancer sequences are now known from mammalian genes (globin, elastase, albumin, β-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297: 17–18 (1982) on enhancing elements for activation of eukaryotic promoters. The enhancer may be spliced into the vector at a position 5' or 3' to the rPTK or receptor construct-encoding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the rPTK or receptor construct.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by amoicillin or tetracycline resistance where appropriate. Plasmids from the transformants are prepared, analyzed by restriction endonuclease digestion, and/or sequenced by the method of Messing et al., *Nucleic Acids Res.* 9: 309 (1981) or by the method of Maxam et al., *Methods in Enzymology* 65: 499 (1980).

Other methods, vectors, and host cells suitable for adaptation to the synthesis of the rPTK or receptor construct in recombinant vertebrate cell culture are described in Gething et al., *Nature* 293: 620–625 (1981); Mantei Iet al., *Nature* 281: 40–46 (1979); Levinson et al.; EP 117,060; and EP 117,058. A particularly useful plasmid for mammalian cell culture expression of rPTK or receptor construct DNA is pRK5 (EP 307,247) or pSVI6B (PCT pub. no. WO 91/08291 published Jun. 13, 1991).

Examples of suitable eukaryotic cell lines for transformation include *Saccharomyces cerevisiae, Schizosaccharomyces pombe* (Beach and Nurse, *Nature* 290: 140 [1981]; EP 139,383 published May 2, 1985); Kluyveromyces hosts (U.S. Pat. No. 4,943,529; Fleer et al., *Bio/Technology* 9: 968–975 [1991]) and Aspergillus hosts such as *A. nidulans* (Ballance et al., *Biochem. Biophys. Res. Commun.* 112: 284–289 [1983]; Tilburn et al., *Gene* 26: 205–221[1983 ]; Yelton et al., *Proc. Natl. Acad. Sci. USA* 81: 1470–1474 [1984]) and *A. niger* (Kelly and Hynes, *EMBO J.* 4: 475–479 [1985]), among lower eukaryotic host microorganisms.

Examples of useful animal host cell lines for transformation include monkey kidney CV1 line transformed by SV40 (COS-7, ATCC CRL 1651); human embryonic kidney line (293 or 293 cells subcloned for growth in suspension culture, Graham et al., *J. Gen Virol.* 36: 59 [1977]); baby hamster kidney cells (BHK, ATCC CCL 10); Chinese hamster ovary cells/-DHFR (CHO, Urlaub and Chasin, *Proc. Natl. Acad. Sci. USA* 77: 4216 [1980]); mouse sertoli cells (TM4, Mather, *Biol. Reprod.* 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383: 44–68 [1982]); MRC 5 cells; FS4 cells; and a human hepatoma line (Hep G2).

Host cells are transformed with the above-described expression or cloning vectors of this invention and cultured in conventional nutrient media modified as appropriate for inducing promoters, selecting transformants, or amplifying the genes encoding the desired sequences. Transformation means introducing DNA into an organism so that the DNA is replicable, either as an extrachromosomal element or as a chromosomal integrant. Depending on the host cell used, transformation is done using standard techniques appropriate to such cells. Successful transformation is generally recognized when any indication of the operation of this vector occurs within the host cell.

For mammalian cells, the calcium phosphate precipitation method of Graham and Van der Eb, *Virology* 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.* 130: 946 (1977) and Hsiao et al., *Proc. Natl. Acad. Sci. (USA)* 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185: 527–537 (1990), and Mansour et al., *Nature* 336: 348–352 (1988).

The mammalian host cells used to produce the rPTK or receptor construct may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth Enz*. 58: 44 (1979), Barnes and Sato, *Anal. Biochem.* 102: 255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of each of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed., IRL Press, 1991.

Gene amplification and/or expression may be measured in a sample directly, for example, by conventional Southern blotting, Northern blotting to quantitate the transcription of mRNA (Thomas, *Proc. Natl. Acad. Sci. USA* 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining to quantitate directly the expression of gene product.

B. Selecting cells for use in the assay

As mentioned above, the cells to be subjected to the assay can be (a) cells having an endogenous receptor, (b) cells which have been transformed with a rPTK, or (c) cells transformed with a receptor construct. The suitability of the cells for use in the assay is investigated.

Cells having the endogenous rPTK can be subjected to a test-run KIRA ELISA using a known ligand to the PTK (e.g. an agonist antibody) and a control (e.g. the diluent for the agonist antibody). A range of ligand concentrations such as those used herein (see Examples 1, 2 and 3) will be used to determine whether sufficient numbers of the receptor are present in the cells being tested. In order to discover whether a cell line is unsuitable because the receptor is constitutively phosphorylated, the cell line can be subjected to the KIRA ELISA disclosed herein, wherein it is exposed to both positive and negative controls (e.g. a known agonist ligand in cell culture media as described herein as a positive control and the cell culture media without the agonist ligand as the negative control). If phosphorylation of the receptor is detected for both positive and negative controls, this may be indicative that constitutive phosphorylation of the receptor is occurring. However, it is possible that a constituent of the serum in the cell culture media is activating the receptor. Thus the cells can be "starved" in serum-free media for about 2–12 hours (depending on cell survival) and then the assay is repeated using the positive and negative controls. If activation is detected for both controls, the cell line may be considered unsuitable and another cell line can be tested.

If the cell line is transformed with the receptor (without the flag polypeptide) a strategy similar to that depicted in FIG. 4 can be used to discover whether or not the cell line is suitable for use in the assay. As a first step, successful transformation and expression of the nucleic acid encoding the rPTK is determined (see FIG. 4, step b). In order to identify whether the ECD of the rPTK is present on the surface of the cells, flow cytometric analysis can be performed using an antibody to the ECD of the receptor. The antibody can be made using the techniques for generating antibodies discussed herein. Flow cytometric analysis can be carried out using the techniques described in *Current Protocols in Immunology*, Ed. Coligen et al., Wiley publishers, Vols. 1 and 2, for example. Briefly, flow cytometric analysis involves incubating intact cells (having the receptor) with antibodies to the ECD thereof, followed by washing. The antibody-bound cells are then incubated with species specific anti-antibody antibodies conjugated to a fluorochrome. Following washing, the labeled cells are analyzed by fluorescence-activated flow cytometry to detect whether the ECD is present on the surface of the cells.

In the following step, i.e. FIG. 4, step (c), the ability of the cell-bound receptor to be activated is tested. In order to determine this, the transformed cells are exposed to a known agonist to the receptor (e.g. the endogenous ligand or an agonist antibody for the receptor). Following exposure, the cells are lysed in a suitable buffer (e.g. sodium dodecylbenzenesulfonate in phosphate buffered saline; SDS in PBS) and subjected to Western blotting with anti-phosphotyrosine antibodies as described in Wang, *Molecular and Cellular Biology* 5(12): 3640–3643 (1985); Glenney et al., *Journal of Immunological Methods* 109: 277–285 (1988); Kamps, *Methods in Enzymology* 201: 101–110 (1991); Kozma et al., *Methods in Enzymology* 201: 28–43 (1991); Holmes et al., *Science* 256: 1205–10 (1992); or Corfas et al., *PNAS, USA* 90: 1624–1628 (1993), for example.

Assuming the Western blotting step indicates that the rPTK can be activated, a KIRA ELISA test run can be performed, see FIG. 4 step (d), to further establish whether or not the transformed cell line can be used in the assay.

In the preferred embodiment of the invention, the KIRA ELISA is a "generic" assay insofar as any rPTK of interest can be studied regardless of the availability of receptor-specific reagents (i. e., capture agent). This embodiment employs a receptor construct having a flag polypeptide at either the amino or carboxyl terminus of the receptor.

If the flag polypeptide is provided at the $NH_2$-terminus (see, e.g., the gD.trk A, B and C receptor constructs disclosed in Example 3), the procedure for selecting a transformed cell line for use in the assay summarized in FIG. 4 can be performed. In this embodiment, the cells are transformed with the flag polypeptide-receptor construct as described earlier herein. See step (a). In step (b), successful transformation of the receptor and flag polypeptide (i.e. the receptor construct) is confirmed. In order to study this, two-dimensional flow cytometric analysis can be performed using antibodies to both the flag polypeptide and the ECD of the receptor. Techniques for two-dimensional flow cytometric analysis are disclosed in *Current Protocols in Immunology*, supra. Assuming successful transformation of the receptor construct is demonstrated, steps (c) and (d) of FIG. 4 are then performed. See the discussion above, for an explanation of steps (c) to (d) of FIG. 4.

A technique for identification of cells which have been successfully transformed with the receptor construct having a C-terminal flag polypeptide and which cells are also suitable for use in the assay is illustrated in FIG. 5. Following cell transformation [step (a)], successful transformation of the receptor is determined by flow cytometric analysis using an antibody directed against the ECD of the receptor of interest, for example. Flow cytometric analysis can be performed substantially as described above. This forms step (b) of the procedure outlined in FIG. 5.

Following step (b), successful transformation of the entire receptor construct (including the COOH-terminal flag polypeptide) is analyzed in step (c). This can be achieved by lysing the cells (using techniques for lysing cells disclosed herein) and immunoprecipitating the membrane extract with an antibody against the receptor of interest. This immunoprecipitated membrane extract is then subjected to western blot analysis with antibodies specific for the flag polypeptide. Alternatively, rPTK-specific ELISA analysis of anti-flag polypeptide captured membrane lysate can be carried out. Briefly, this involves coating ELISA wells with appropriate flag specific capture agent. The wells are blocked, washed, and the lysate is then incubated in the wells. Unbound receptor construct is removed by washing. The wells are then reacted with receptor-specific antibody or antibodies, either directly or indirectly conjugated to HRPO. The wells are washed and the HRPO is then exposed to the chromogenic substrate (e.g., TMB).

Steps (d) and (e), i.e., detecting receptor activation and KIRA ELISA test run, are essentially the same as those steps described above.

Once useful cells are identified, they are subjected to the KIRA stage of the instantly claimed assay.

C. Coating the first solid phase with the cells

The first solid phase (e.g. a well of a first assay plate) is coated with cells having the endogenous receptor or cells which have been transformed pursuant to the preceding sections.

Preferably, an adherent cell line is chosen, so that the cells naturally adhere to the first solid phase. However, use of an adherent cell line is not essential. For example, non-adherent cells (e.g. red blood cells) can be added to round bottomed wells of an assay plate such as that sold by Becton Dickinson Labware, Lincoln Park, N.J., for example. The assay plate is then placed in a plate carrier and centrifuged so as to create a pellet of cells adhering to the base of the wells. The cell culture supernatants are removed using a pipette. Thus, use of an adherent cell is clearly advantageous over non-adherent cells since it reduces variability in the assay (i.e, the cells in the pellet of the round bottom wells may be taken up with the supernatant when the alternative method is used).

The cells to be added to the wells of the first assay plate may be maintained in tissue culture flasks and utilized when cells densities of about 70–90% confluency are achieved. Then, generally between about $1 \times 10^4$ to $3 \times 10^5$ (and preferably $5 \times 10^4$ to $1 \times 10^5$) cells are seeded per flat-bottom well, using a pipette, for example. It has been found that, contrary to expectations, addition of cell concentrations mentioned above is sufficient to enable activation of the rPTK to be measured in the ELISA stage of the assay, without the need to concentrate or clarify the cells or cell lysate prior thereto. Often, the cells are diluted in culture medium prior to seeding them in the wells of the microtiter plate to achieve the desired cell densities.

Usually, the cells are cultured in the microtiter plates for a sufficient period of time to optimize adherence to the wells thereof, but not too long such that the cells begin to deteriorate. Thus, incubation for about 8 to 16 hours at a temperature which is the physiological optimum for the cells (usually about 37° C.) is preferred. Suitable media for culturing the cells are described in Section 1A above. Culturing in 5% $CO_2$ is recommended.

Following incubation overnight, the well supernatants are decanted and excess supernatant may be further removed by lightly tamping the microtiter plates with an absorbent substrate, e.g., a paper towel, but a sponge works equally well. Thus, a substantially homogeneous layer of adhering cells remains on the internal surfaces of the individual wells of the microtiter plate. These adhering cells are then exposed to the analyte.

D. Preparation and addition of the analyte

As mentioned above, the analyte may comprise an agonist ligand (or suspected agonist) or an antagonist (or suspected antagonist) for the rPTK of interest. The ligand may be an endogenous polypeptide, or a synthetic molecule, such as an inorganic or organic molecule. Usually, the ligand is a polypeptide. This assay is useful for screening molecules which activate (or antagonize activation) of the tyrosine kinase receptor of interest. Thus, the assay can be used for developing therapeutically effective molecules.

Where the ligand is an agonist, the molecule can comprise the native growth factor e.g., heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), transforming growth factors alpha and beta (TGF-α and TGF-β), hepatocyte growth factor (HGF), fibroblast growth factor (FGF) and nerve growth factor (NGF). Many of these growth factors are available commercially. Alternatively, the growth factor can be made by peptide synthesis or recombinant techniques which are described herein. Synthetic small molecule agonists can similarly be generated by those skilled in the art using conventional chemical synthesis techniques.

Where the ligand is present in a biological fluid, the analyte can be prepared using techniques which are well known in the art. Body fluid such as blood or amniotic fluid may be used directly, however concentration may be required. If tne analyte to be tested comprises a particular tissue, the cells thereof can be grown in cell culture and the supernatant can be tested for secreted ligand.

Often, the ligand is diluted in an aqueous diluent (such as cell culture media) so that a standard curve can be generated. However, the ligand may be present in a cell or a cell component (e.g., the cell membrane). In particular, it has been found that the assay can be used to detect the presence of a ligand in the cell membrane of a selected cell line. This is clearly useful for discovering a novel endogenous ligand for a known rPTK.

The ligand composition is added to each well which contains the adhering cells using a pipette, for example. At least one control well (e.g. to which the aqueous diluent for the ligand is added) is included in the assay.

The adhering cells are usually stimulated for a sufficient period of time to optimize the signal, but not too long such that the signal decreases as a consequence of dephosphorylation of the rPTK by endogenous phosphatases. A suitable stimulation period is between about 10 to 60 minutes, preferably about 30 minutes at a physiologically optimal temperature for the cells (usually about 37° C.).

Following activation, well supernatants are decanted and the plates can then be lightly tamped with an absorbent substrate to remove excess supernatant.

The assay can be used to detect antagonist ligands for the rPTK of interest. Antagonists generally fall into two categories (a) ones which bind to the rPTK and thereby block binding and/or activation of the rPTK by an agonist thereto (the antagonist may bind to the ECD, but this is not necessarily the case) and (b) those which bind to the agonist and thus prevent activation of the rPTK by the agonist.

In order to detect antagonist molecules from category (a) above, the cells are exposed to the suspected antagonist ligand substantially as mentioned above. Following exposure to the antagonist, the well supernatants are decanted and the plates are lightly tamped. Then, a known agonist (e.g., the endogenous growth factor) is added to the washed cells essentially as discussed in the preceding paragraphs, following which, the well supernatants are decanted and plates are lightly tamped. Alternatively, a composition comprising both the antagonist and agonist can be added to the adhering cells substantially as discussed above. Ability of the suspected antagonist to block binding and/or activation of the rPTK can subsequently be measured by ELISA as discussed below.

To detect antagonist molecules from category (b) above, a known agonist is pre-incubated with the suspected antagonist prior to the KIRA stage of the assay. This incubation is carried out for a sufficient period of time to enable a complex of the antagonist-agonist to form; from 30 min. to 12 hours, for example. This complex is then subjected to the assay with the non-complexed agonist and antagonist used as controls.

Following exposure to the agonist (and optionally the antagonist) ligand, the cells are lysed, as discussed below.

E. Solubilizing the cells

In this step of the assay, the cells are lysed so as to solubilize the rPTK such that it remains activated (i.e., the tyrosine residues remain phosphorylated) for the ELISA stage of the assay. Thus, the cells are lysed using a lysis buffer as described above which serves to solubilize the rPTK or receptor construct, yet does not dephosphorylate or denature the rPTK.

Where microtiter plates are used as mentioned above, about 75 to 200 $\mu$l of lysis buffer is added to each well. The plates can then be agitated gently using a plate shaker (e.g., such as that sold by Bellco Instruments, Vineland, N.J.) for about 1 to 2 hours. Shaking can be carried out at room temperature.

2. Enzyme-Linked Immunosorbent Assay—ELISA

The second stage of the assay involves a sandwich ELISA performed in the second assay plate. In order to carry out the ELISA, a capture agent is prepared.

A. Preparation of the capture agent

As mentioned above, the capture agent often comprises a polyclonal antibody (usually an affinity purified polyclonal antibody) or monoclonal antibody. Other capture agents are envisaged and are discussed in the definitions section above. The capture agent either binds specifically to the kinase receptor, or to the flag polypeytide (i.e. the antigen).

Polyclonal antibodies to the antigen (either the receptor or the flag polypeptide) generally are raised in animals by multiple subcutaneous (sc) or intraperitoneal (ip) injections of the antigen or an antigenic fragment thereof (often the ECD of the rPTK) and an adjuvant. It may be useful to conjugate the antigen or a fragment containing the target amino acid sequence to a protein that is immunogenic in the species to be immunized (e.g., keyhole limpet hemocyanin), using a bifunctional or derivatizing agent.

The route and schedule for administration of immunogen to the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant (or other suitable adjuvant) by subcutaneous injection at multiple sites. 7 to 14 days later animals are bled and the serum is assayed for anti-antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies can be prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones producing the desired antibody. The hybridoma technique described originally by Kohler and Milstein, *Eur. J. Immunol.* 6: 511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are then sterile filtered. Where the antibody is a polyclonal antibody, it is generally affinity purified using an affinity column generated from the antigen of interest so as to provide a substantially specific capture antibody. Affinity chromatography is usually preceded by other purification techniques, such as liquid chromatography.

In a further embodiment, antibodies or antibody fragments can be isolated from antibody phage libraries generated via the techniques described in McCafferty et al., *Nature*, 348: 552–554 (1990), using the flag polypeptide, rPTK, or a fragment thereof, to select for a suitable antibody or antibody fragment. Clackson et al., *Nature*, 352: 624–628 (1991) and Marks et al., *J. Mol. Biol.*, 222: 581–597 (1991) describe the isolation of murine and human antibodies, respectively, using phage libraries. Subsequent publications describe the production of high affinity (nM range) human antibodies by chain shuffling (Mark et al., *Bio/Technol.* 10: 779–783 [1992]), as well as combinatorial infection and in vivo recombination as a strategy for constructing very large phage libraries (Waterhouse et al., *Nuc. Acids Res.*, 21: 2265–2266 [1993]). Thus, these techniques are viable alternatives to traditional monoclonal antibody hybridoma techniques for isolation of "monoclonal" antibodies which are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-rPTK or anti-flag polypeptide monoclonal antibody herein. Thus, the antibody may be made by recombinant DNA methods (Cabilly et al., U.S. Pat. No. 4,816,567).

Binding of the capture agent is not affected by the presence or absence of a ligand bound to the receptor and the capture agent does not sterically block access to the phosphorylated tyrosine(s) by the anti-phosphotyrosine antibody. Furthermore, the capture agent does not, of course, activate the receptor of interest. In order to screen for an antibody having these characteristics, the procedure outlined in FIG. 3 can be carried out.

First, once the capture agent (e.g. an antibody or streptavidin) has been chosen, binding to either the receptor or the flag polypeptide (where a receptor construct is to be used in the assay) is confirmed. This can be determined by flow cytometric analysis, immuno-precipitation or antigen-coat ELISA, for example. Flow cytometric analysis has been described above. Immunoprecipitation usually involves lysing the cells (having the receptor or receptor construct) in non-ionic detergent (e.g. 0.5% Triton X-100) in a suitable buffer (e.g. PBS) and the cell lysates thus obtained are then incubated with the potential anti-receptor or anti-flag polypeptide capture agent. The immune complexes are precipitated with either (a) anti-capture agent antibodies in the presence of polyethylene glycol (PEG) which enhances precipitation of the immune complex or with (b) insoluble (e.g. agarose bound) protein A or protein G. The immunoprecipitated material is then analyzed by polyacrylamide gel electrophoresis (PAGE). For antigen-coat ELISA, ELISA wells are coated overnight with either the purified receptor, purified flag polypeptide or purified receptor construct. The coated wells are then exposed to the potential capture agent and screened with HRPO-conjugated species specific anti-capture agent antibody.

The ability of the capture agent to bind to the receptor or flag polypeptide in the presence of a ligand to the receptor is also confirmed. This can be analyzed by incubating the receptor or receptor construct with a known ligand for the receptor (e.g. the endogenous growth factor or an agonist antibody thereto). Flow cytometric analysis, immunoprecipitation or antigen-coat ELISA can then be performed substantially as described above to investigate binding of the capture agent.

Assuming the capture agent is suitable as determined by the preceding two steps, it is then shown that the capture agent does not induce receptor activation (i.e. autophosphorylation) either before or after cell lysis. Thus, the cell-bound receptor or receptor construct is exposed to either the potential capture agent or a negative control (e.g. a control antibody which does not activate the receptor). Following cell lysis, the receptor or receptor construct can be subjected to Western blot analysis using labeled anti-phosphotyrosine antibodies. See, e.g., Glenney et al., *Journal of Immunological Methods* 109: 277–285 (1988); Kamps, *Methods in Enzymology* 201: 101–110 (1991); Kozma et al., *Methods in Enzymology* 201: 28–43 (1991); or Holmes et al., *Science* 256: 1205–10 (1992). To establish whether the capture agent induces receptor activation following cell lysis, a trial run of the KIRA ELISA (with both the capture agent and a negative control as discussed above) can be performed.

Finally, the ability of an anti-phosphotyrosine antibody (e.g. biotinylated anti-phosphotyrosine antibody) to bind the activated receptor in the presence of the potential capture agent is confirmed by a trial run in the KIRA ELISA disclosed herein.

Assuming the capture agent meets all the criteria specified above, it has good potential for use in the KIRA ELISA.

Once a suitable capture agent has been prepared, the second solid phase is coated therewith. Between about 0.1 to 10 μg/ml of capture agent can be added to each well of the second assay plate using a pipette, for example. The capture agent is often provided in a buffer at a high pH (e.g., between about 7.5 to 9.6) so that it has an increased overall charge and therefore displays enhanced binding to the second assay plate. Usually, the capture agent will be incubated in the wells for between about 8 to 72 hours to enable a sufficient coating of the capture agent to form on the inside walls of the wells. This incubation is generally carried out at low temperatures (e.g., between about 3–8° C.) to avoid or reduce degradation of the capture agent.

Following incubation, the wells of the plate are decanted and tamped lightly with an absorbent substrate. Non-specific binding is then blocked. In order to achieve this, a block buffer, is added to the wells. For example, a block buffer containing bovine serum albumin (BSA) such as that sold by Intergen Company, Purchase, N.Y., is suitable. It has been found that addition of between about 100 to 200 μl of block buffer to each well followed by gentle agitation at room temperature for between about 1–2 hours is sufficient to block non-specific binding. It is also possible to add the block buffer directly to the cell lysate obtained in the previous step rather than to the second assay plate.

Following this, the capture agent-coated plates are washed several times (usually between about 3–8 times) with a wash buffer. The wash buffer can comprise phosphate buffered saline (PBS) at pH 7.0 to 7.5, for example. However, other wash buffers are available which can also be used. Conveniently, an automated plate washer, such as the ScanWasher 300 (Skatron Instruments, Inc., Sterling, Va.) can be used for this, and other, washing steps of the assay.

B. Measuring tyrosine phosphorylation

The activated, solubilized rPTK (or receptor construct) is then added to the wells having the capture agent adhering thereto. As a general proposition, about 80% of cell lysate obtained as mentioned under Section 1E above can be added to each well (i.e., about 60 to 160 μl depending on the original volume of the wells). The lysate is incubated with the capture agent for an adequate period of time to enable the rPTK to be captured in the wells, e.g., from 1 to 3 hours. Incubation can be carried out at room temperature.

Unbound cell lysate is then removed by washing with wash buffer. Following this washing step, an amount of the anti-phosphotyrosine antibody which is equal to, or less than, the amount of block buffer added previously, is added to each well. For example, about 50 to 200 μl of an anti-phosphotyrosine antibody preparation having between about 0.3 to 0.5 μg/ml of antibody in a suitable buffer (e.g., PBS with a detergent such as those included in the lysis buffer) is added to the well. This is followed by a washing step to remove unbound anti-phosphotyrosine antibody.

Tyrosine phosphorylation is then quantified by the amount of anti-phosphotyrosine antibody binding to the second solid phase. Many systems for detecting the presence of an antibody are available to those skilled in the art. Some examples follow.

Generally, the anti-phosphotyrosine antibody will be labelled either directly or indirectly with a detectable label. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, supra, for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73: 147–166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]).

(ii) alkaline phosphatase (AP) with para-Nitrophenyl phosphate as chromogenic substrate.

is (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. See, *Current Protocols in Immunology*, supra, for a review of techniques involving biotin-avidin conjugation. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-phosphotyrosine antibody need not be labeled, and the presence thereof can be detected using a labeled anti-antiphosphotyrosine antibody (e.g. anti-mouse anti-phosphotyrosine antibody conjugated with HRPO).

In the preferred embodiment, the anti-phosphotyrosine antibody is labeled with an enzymatic label which catalyzes a color change of a substrate (such as tetramethyl benzimidine [TMB], or orthaphenylene diamine [OPD]). Thus, the use of radioactive materials is avoided. A color change of the reagent can be determined spectrophotometrically at a suitable wavelength (e.g. 450 nm for TMB and 490 nm for OPD, with a reference wavelength of 650 nm).

3. Intracellular Kinase Activity

The assay described herein is also useful for measuring phosphorylation and/or activation of intracellular kinases (e.g. cytoplasmic tyrosine kinases and/or cytoplasmic serine-threonine kinases). Phosphorylation of these molecules can occur as a consequence of trans-phosphorylation of the intracellular kinase by a kinase receptor or "receptor complex" (which comprises one or more kinase receptors residing in a cell membrane). Examples of intracellular tyrosine kinases include insulin receptor substrate I (IRS-1), Shc, Ras and GRB2, for example. Antibodies to human Shc, human Ras and GRB2 can be obtained commercially from UBI, NY, which can be used as capture agents for these tyrosine kinases. Examples of intracellular serine-threonine kinases include MEK and MAPK.

In order to measure phosphorylation of these kinases, the procedure is essentially as described above except that a chimera of the intracellular kinase and the flag polypeptide is normally formed (i.e. a "kinase construct"). Alternatively, the cell has an endogenous intracellular kinase or is transformed with nucleic acid encoding an intracellular kinase of interest. Generally, a eukaryotic cell will be transformed with nucleic acid encoding a kinase construct. Upon expression of the nucleic acid, the kinase or kinase construct will reside intracellularly (i.e. in the cytoplasm). The cells comprising the kinase or kinase construct are subjected to the KIRA as discussed above. Exposure to the agonist may result in trans-phosphorylation of the intracellular kinase which can be quantified in the ELISA as elaborated above. The capture agent in the ELISA binds to either the intracellular kinase or to the flag polypeptide.

4. Serine-Threonine Kinase Activity

This assay is further useful for measuring phosphorylation and/or activation of serine-threonine kinases. The term "serine-threonine kinase" refers to a kinase which phosphorylates a substrate which has at least one phosphate accepting alcohol group. The serine-threonine kinase is usually a "receptor" insofar as it has a ligand-binding ECD, TM domain and ICD. The ICD usually comprises a catalytic kinase domain and generally has one or more phosphate accepting serine and/or threonine residues. Examples of intracellular serine-threonine kinases include MEK and MAPK. See section 3 above for a discussion as co measuring phosphorylation of intracellular serine-threonine kinases. Examples of serine-threonine kinase receptors include daf-1, activin type II receptor (ActR-II), activin type IIB receptor (ActR-IIB), TGF-β type II receptor (TβR-II), activin receptor-like kinase (ALK) –1, –2, –3, –4 and TGF-β type I receptor (TβR-1)/ALK-5. See ten Dijke et al., supra. The serine-threonine kinase assay is essentially the same as described above for tyrosine kinases, except that phosphorylation is quantified using anti-phosphoserine and/or anti-phosphothreonine antibodies. Anti-phosphoserine and anti-phosphothreonine monoclonal antibodies can be purchased from Sigma Immuno Chemicals, St Louis, Mo., for example.

5. Phosphatase Activity

Phosphatase activity can similarly be measured using the assay described herein. Phosphatase enzymes are able to dephosphorylate phosphorylated tyrosine, serine and/or threonine residues (i.e. liberate inorganic phosphate from phosphoric esters of such amino acid residues). Generally the phosphatase enzyme is specific for either tyrosine residues or serine-threonine residues but sometimes can dephosphorylate tyrosine, serine and threonine residues. Sometimes "endogenous" phosphatase activity is measured and this refers to the activity of phosphatase enzyme(s) which exist in nature in a selected cell.

In order to quantify endogenous phosphatase activity, cells possessing at least one phosphatase are stimulated in the presence and absence of one or more phosphatase inhibitors. Examples of protein tyrosine phosphatase (PTPase) inhibitors include sodium orthovanadate and sodium molybdate (Sigma Chemical Co., St. Louis, Mo.). ICN Biochemicals supply okadaic acid which is a serine-threonine phosphatase inhibitor. As a general proposition, between about 1–10 $\mu$M phosphatase inhibitor can be added to each well of the assay plate. In all other respects, the assay is performed essentially as discussed above. Thus, the ability of endogenous phosphatases to dephosphorylate a kinase in the selected cell can be quantified.

In the preferred embodiment, a phosphatase enzyme of interest can be studied. Examples of protein tyrosine phosphatases (PTPases) include PTP1B, PTPMEG, PTP1c, Yop51, VH1, cdc25, CD45, HLAR. PTP18, HPTPα and DPTP10D. See Zhang and Dixon, *Adv. Enzym.* 68: 1–36 (1994). Examples of protein serine-threonine phosphatases include PP1, PP2A, PP2B and PP2C. See *Meth. Enzym.*, ed Hunter & Sefton, Academic press, New York, 201: 389–398 (1991). These proteins can be purchased commercially or made using the recombinant techniques described herein. To measure phosphatase activity, the KIRA ELISA can be performed essentially as described above with the following modifications. Following capture of the kinase or kinase construct (e.g. receptor construct) to the second solid phase and the washing step (to remove unbound cell lysate), the phosphatase of interest is added to the wells of the second assay plate and incubated with the adhering kinase or kinase construct. For example, between about 50–200 $\mu$l of the phosphatase in a suitable dilution buffer (see *Meth. Enzym.*, ed Hunter & Sefton, Academic press, New York, 201: 416–440 [1991]) can be added to each well. This is generally followed by gentle agitation at room temperature (or 37° C.) for between about 30 min to 2 hours to allow the phosphatase to dephosphorylate the kinase. Following washing to remove the phosphatase, the decreased degree of phosphorylation of the kinase relative to the control (i.e. no phosphatase added) is quantified by ELISA as described earlier herein.

6. Kits

As a matter of convenience, the reagents can be provided in a kit, i.e., a packaged combination of reagents, for combination with the analyte in assaying the ability of the analyte to activate or prevent activation of a rPTK of interest. The components of the kit will be provided in predetermined ratios. Thus, a kit will comprise the specific second solid phase for the assay as well as the anti-flag polypeptide capture agent either packaged separately or captured to the second solid phase (e.g. a microtiter plate). Usually, other reagents, such as the anti-phosphotyrosine antibody labelled directly or indirectly with an enzymatic label will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. a block buffer and a lysis buffer) and the like. Conveniently, the kit can also supply the homogeneous population of cells which have been transformed with the receptor construct. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the KIRA ELISA.

7. Uses for the Assay

This application provides two assays which are useful for reliable, sensitive and quantitative detection of kinase activation. The first assay can be used where a kinase receptor-specific capture antibody having the desired characteristics herein described is available or has been prepared. The second assay is a generic assay which enables activation of any kinase receptor to be measured via the use of a flag polypeptide and a capture agent which binds specificity thereto.

These assays are useful for identifying novel agonists/antagonists for a selected kinase receptor. Also, the assay provides a means for studying ligand-receptor interactions (i.e., mechanism studies). Also the presence of an endogenous receptor in a selected cell line can be quantified using the assay. The assays are further useful for identifying the presence of a ligand for a selected kinase receptor in a biological sample and, e.g., establishing whether a growth factor has been isolated following a purification procedure. It is desirable to have an assay for measuring the ability of these growth factors to activate their respective receptors.

The assay also has clinical applications for detecting the presence of a ligand for a selected rPTK (e.g. the insulin receptor) in a biological sample taken from a human and thus patients having elevated or depressed levels of the ligand can be identified. This is particularly desirable where elevated or depressed levels of the ligand cause a pathological condition. Accordingly, candidates for administration of the selected ligand (e.g. insulin) can be identified through this diagnostic method. It is possible, using the assay disclosed herein, to assay the pK of agonists or antagonists administered to a patient. This assay also facilitates the detection of shed receptor in a biological sample.

The assay is also useful to quantify phosphatase activity of endogenous phosphatases or, in the preferred embodiment, a phosphatase of interest. This can be used for screening phosphatase inhibitors, for example.

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLE 1

KIRA ELISA of the HER2 Receptor

The assay system described in this example was developed to measure the extent of autophosphorylation as a result of the interactions between the HER2 receptor and its specific activator, heregulin (HRG). The overexpression of p185$^{HER2}$ has been correlated with poor clinical outcome in a number of epithelial-derived cancers. Heregulin and its rodent homologue, neu differentiation factor (NDF), were originally purified based on their ability to stimulate the autophosphorylation of a 185 kDa protein in the breast carcinoma cell lines MCF-7 and MDA-453, respectively. In this embodiment of the invention, the cell line expressing the tyrosine kinase receptor DNA (either endogenous or transformed) is adherent and there is an antibody (e.g. monoclonal or affinity purified polyclonal) capable of specifically binding the receptor such that it neither stimulates autophosphorylation in the absence of ligand nor suffers impaired binding due to the presence of bound ligand. Standard curve preparations and many samples may easily be run simultaneously in replicate and at several dilutions using this assay, readily allowing quantitation of ligand activity in a large number of unknown samples.

(i) Capture agent preparation

Polyclonal anti-HER2 antibody was isolated from pooled immune sera from New Zealand White rabbits immunized with the extracellular domain of the HER2 molecule (Fendly et al., *Journal of Biological Response Modifiers* 9: 449–455 [1990]). The rHER2 ECD specific antibodies were affinity purified using an FPLC (Pharmacia Biotech, Inc, Piscataway, N.J.) with an affinity column generated from rHER2 ECD conjugated to Avidgel F (Bioprobe International, Inc, Tustin, Calif.). The resulting purified antibody stock was 0.829 mg/ml in phosphate buffered saline (PBS), pH 7.4, and was stored as 0.5 ml aliquots at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotynylated using long-arm biotin-N-hydroxysuccinamxde (Biotin-X-NHS, Research Organics, Cleveland, Ohio).

(iii) Ligand

The recombinant truncated form of β1heregulin (MW= 7.88 Kd) corresponding to residues 177–244 (HRGβ1$_{177-244}$) was produced in *E. coli* and purified to homogeneity as described in Holmes et al., *Science*, 256: 1205–1210 (1992) and was stored at 4° C. as an 89.7 μM stock solution in 50 mM Tris/HCl, pH 7.5.

(iv) Adherent Cells

MCF-7 (ATCC-HTB 22), an adherent cell line isolated from a human breast adenocarcinoma, was obtained from American Type Culture Collection (ATCC, Rockville, Md.). MCF-7 cells have been shown to produce measurable levels of surface p185$^{HER2}$ by both FACS and ELISA analysis. The cells were maintained in 150 cm$^2$ tissue culture flasks (Corning Inc, Corning, N.Y.) and utilized when at cell densities of 60% to 75% confluency. For the assay, 2×10$^5$ cells were seeded per well in flat-bottom microtiter plates (Falcon 3072, Becton Dickinson Labware, Lincoln Park, N.J.) cultured overnight at 37° C. in 5% CO$_2$. Cells were grown in F12/DMEM 50:50 Gibco as a custom formulation (Gibco/BRL, Life Technologies, Grand Island, N.Y.). The medium was supplemented with 10% FBS (HyClone, Logan, Utah), 25 mM HEPES (Gibco) and 2 mM L-glutamine (Gibco).

(v) KIRA ELISA

MCF-7 cells (2×10$^5$) in 100 μl media were added to each well in a flat-bottom-96 well culture plate and cultured overnight at 37° C. in 5% CO$_2$. The following morning the well supernatants were decanted, and the plates were lightly tamped on a paper towel. 50 μl of media containing either experimental samples or the recombinant HRGβ1$_{177-244}$ standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate (Na$_3$VO$_4$, Sigma Chemical Co, St. Louis, Mo.), pH 7.5. The plate was then agitated gently on a plate shaker (Bellco Instruments, Vineland, N.J.) for 60 min. at room temperature.

While the cells were Deing solubilized, an ELISA microliter plate (Nunc Maxisorp, Inter Med, Denmark) coated overnight at 4° C. with the affinity-purified polyclonal anti-HER2 ECD (1.0 μg/ml in 50 mM carbonate buffer, pH 9.6, 100 μl/well) was decanted, tamped on a paper towel and blocked with 150 μl/well of Block Buffer[PBS containing 0.5% BSA (Intergen Company, Purchase, N.Y.) and 0.01% thimerosall] for 60 min. at room temperature with gentle agitation. After 60 minutes, the anti-HER2 ECD coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized p185$^{HER2}$ from the cell-culture microtiter well was transferred (85 μl/well) to anti-rHER2 ECD coated and blocked ELISA well and was incubated for 2 h at room temperature with gentle agitation. The unbound receptor was removed by washing with wash buffer and 100 μl of biotinylated 4G10 (anti-phosphotyrosine) diluted 1:2000 in dilution buffer (PBS containing 0.5% BSA, 0.05% Tween-20, 5 mm EDTA, and 0.01% thimerosal), i.e. 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0 M H$_3$PO$_4$. The absorbance at 450 nm was read with a reference wavelength of 650 nm (ABS$_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 7 was generated by stimulating MCF-7 cells with 3000, 1000, 333, 111, 37, 12, 4, or 0 pM HRGβ1$_{177-244}$ and presented as pM HRGβ1$_{177-244}$ vs. mean ABS$_{450/650}$ ±sd using the DeltaSoft program. Sample concentrations were obtained by interpolation of their absorbance on the standard curve and are expressed in terms of pM HRGβ1$_{177-244}$ activity.

When the data were fitted to a 4-parameter nonlinear least squares equation, they resulted in a correlation coefficient of 0.9998. For the data shown in FIG. 7, the EC$_{50}$ of receptor activation by HRGβ1$_{177-244}$ was 373 pM. To demonstrate the highly reproducible nature of the p185$^{HER2}$ KIRA ELISA, seven standard curves were generated over the period of one month and the $EC_{50}$'s are averaged. This gives an $EC_{50}$ave for $HRG\beta1_{177-244}$ of 360±40 pM (average±SD).

(vi) Intra- and inter-assay precision and assay specificity

The intra-assay variability was determined by performing the $p185^{HER2}$ KIRA ELISA on three separate days. For each test, the standard curve is run in triplicate. Controls with $HRG\beta1_{177-244}$ corresponding to high (1000 pM), mid (200 pM) and low (40 pM) were assayed in 24 replicates. The ABS450/650 of the individual test samples were converted to pM $HRG\beta1_{177-244}$ activity and the 24 converted values for each test concentration were averaged. The data are expressed as averaged value and % coefficient of variation (% cv; [(intra-assay standard deviation/intra-assay averaged calculated value)×100]. See Table 1A below.

TABLE 1

Intra- and Inter-assay Variation

A. Intra-assay Precision (n-24 per test)

| | High Value[a] | | Mid Value | | Low Value | |
|---|---|---|---|---|---|---|
| | Average Value (pM) | % cv[b] | Average Value (pM) | % cv | Average Value (pM) | % cv |
| Test #1 | 1256 | 19.5% | 209 | 10.8% | 33 | 12.3% |
| Test #2 | 1078 | 10.0% | 196 | 5.1% | 38 | 7.5% |
| Test #3 | 999 | 14.3% | 196 | 6.3% | 35 | 11.3% |

B. Inter-assay Precision (n = 3)

| Average Value (pM) | % cv[c] | Average Value (pM) | % cv | Average Value (pM) | % cv |
|---|---|---|---|---|---|
| 1100 | 4.3% | 200 | 6.3% | 34 | 9.0% |

[a]Expected high value: 1000 pM; mid value: 200 pM; low value: 40 pM
[b]Intra-assay % cv determined as intra-assay sd/intra-assay average × 100
[c]Inter-assay % cv determined as inter-assay sd/inter-assay average × 100

The intra-assay variability of the KIRA ELISA was within acceptable limits despite the fact that the assay actually consists of both bioassay and ELISA components. The coefficients of variance (%) for the highest values were under 20% and for the mid and low values were at or under 10%.

The inter-assay variability was determined by averaging the values from upper-most three adjacent wells (of the 24 wells run) for a given sample concentration from each run. The three separate averages for each test concentration were then averaged. The data were expressed as averaged value and % cv [(inter-assay standard deviation/inter-assay averaged value)×100]. See Table 1B. above. The inter-assay variability of the KIRA ELISA was within acceptable limits.

In order to confirm the specificity of the assay, MCF-7 cells were stimulated with either $HRG\beta1_{177-244}$ at 3000, 1000, 333, 111, 37, 12, 4 or 0 pM or insulin-like growth factor-1 (IGF-1), epidermal growth factor (EGF), vascular endothelial growth factor (VEGF), or insulin at 30000, 10000, 3333, 1111, 370, 120, 40 or 0 pM. The $p185^{HER2}$ KIRA ELISA was then performed as described above. The results are depicted in FIG. 8.

The $p185^{HER2}$ KIRA ELISA was clearly specific for heregulin. While $HRG\beta1_{177-244}$ induced normal receptor stimulation and autophosphorylation, the closely related EGF gives only a slight stimulation ($OD_{450/650}$=0.239) at the highest concentration tested (100 nM). Since EGF-R is produced in MCF-7 cells, this signal is likely due to EGF receptor transphosphorylation of $p185^{HER2}$. Neither insulin-like growth factor-1 (IGF-1), vascular endothelial growth factor (VEGF) nor insulin have any detectable effect on the MCF-7 $p185^{HER2}$ KIRA ELISA, the latter despite the fact that MCF-7 cells produce active insulin receptors.

The results presented in this example demonstrate that the KIIA ELISA is a useful method for assaying ligand activation of a kinase receptor, e.g., heregulin activation of the $p185^{HER2}$ receptor. Levels of receptor activation in terms of tyrosine phosphorylation are easily cuantified and an $EC_{50}$ for a given ligand is readily determined. One potential use for this assay would be to screen compounds for receptor agonist or antagonist activities. The potential throughput for this assay greatly surpasses that of Western blot analysis. Since the cell-culture portion of the assay is conducted in 96-well plates, many samples may be run in replicate at different dilutions at one time in a one-day assay.

EXAMPLE 2

KIRA ELISA of the Rse Receptor

Mark et al., Journal of Biological Chemistry 269(14): 10720–10728 (1994) describe isolation of the Rse receptor protein tyrosine kinase from human and murine tissues. This Rse receptor with a carboxyl-terminal flag polypeptide (i.e. Rse.gD) was subjected to the KIRA ELISA described herein. The experimental procedure is outlined below.

(i) Capture agent preparation

Monoclonal anti-gD (clone 5B6) was produced against a peptide from Herpes simplex virus glycoprotein D (Paborsky et al., Protein Engineering 3(6): 547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research organics, Cleveland, Ohio).

(iii) Ligand

Since the endogenous ligand for the Rse receptor was not available, an agonist antibody for the Rse receptor was prepared which forms the ligand for the KIRA ELISA described in this Example. To generate the agonist antibody, a Rse.IgG chimera was generated. Briefly, the coding sequence of the ECD of Rse was fused to that of the human IgG-γ1 heavy chain in a multi-step process. PCR was used to generate a fragment with a unique BstEII site 3' to the coding sequences of the Rse amino acid 428. The PCR product was joined to the human IgG-γ1 heavy chain cDNA through a unique BstEII site in that construct (Mark et al., J. Cell. Biol., 267: 26166–26171 [1992]). The resulting construct (termed pRK.bpTK3.IgG.fusion) contained the coding sequences for amino acids 375–428 of Rse joined to those encoding human IgG-γ1 heavy chain. The remaining portion of the Rse ECD (amino acids 1–374) was then added by linkage through the Bam HI site in pRK.bpTK3.IgG.fusion to yield pRK.Rse.IgG.

To generate stable cell populations expressing Rse.IgG, the cDNA encoding Rse.IgG was subcloned into the episomal CMV-driven expression plasmid pCIS.EBON, a pRK5 derivative disclosed in Cachianes et al., Bio, Techniques, 15: 225–259 (1993). Human fetal kidney 293 cells (obtained from ATCC, 12301 Parklawn Drive, Rockville, Md., USA) were transfected by the calcium phosphate technique. Cell monolayers were incubated for four hours in the presence of the DNA precipitate, glycerol shocked, and cultured in F12:DMEM (1:1) containing 2 mM glutamine, 10% fetal bovine serum, penicillin and streptomycin. After 48 hours, populations were replated in media containing G418 to select for a stable population of cells. Conditioned media was collected from cells expressing Rse.IgG nucleic acid that have been cultured in serum-free media for 72 hours in the absence of G418.

(iv) Preparation of Rse.gD nucleic acid

Synthetic double stranded oligonucleotides were used to reconstitute the coding sequence for the C-terminal 10 amino acids (880–890) of human Rse and add an additional 21 amino acids containing an epitope for the antibody 5B6 and a stop codon. The final sequence of the synthetic portion of the fusion gene was:

coding strand:

```
5'-TGCAGCAAGGGCTACTGCCACACTCGAGCTGCGCAGATGCTAGCCTCAAGATGGCTG    (SEQ ID NO: 10)

ATCCAAATCGATTCCGCGGCAAAGATCTTCCGGTCCTGTAGAAGCT-3' noncoding (anti-sense) strand:

5'-AGCTTCTACAGGACCGGAAGATCTTTGCCGCGGAATCGATTTGGATCAGCCATCTTG    (SEQ ID NO: 11)

AGGCTAGCATCTGCGCAGCTCGAGTGTGGCAGTAGCCCTTGCTGCA-3'.
```

Rse.IgG was purified by affinity chromatography on a protein A column using procedures as described by Chamow, S. M., et al., *Biochemistry*, 29: 9885–9891 (1990) with the following minor modifications. Conditioned media collected from cells expressing the Rse.IgG was adjusted to 0.1 M citrate pH 6.0 and loaded directly onto a protein A column (Repligen). The column was washed with 0.1 M citrate, pH 6.0, and was eluted with 3 M $MgCl_2$ with 10% glycerol. Fractions were pooled and desalted on a PD-10 column, dialyzed and concentrated against PBS. Protein concentrations were determined by an ELISA against human IgG (Fc). The protein was analyzed for purity by Coomassie staining of PAGE gels.

Polyclonal antibodies were generated in New Zealand white rabbits against the Rse.IgG formed as described above. 4 μg of Rse.IgG in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93, 3–12 [1983]). For subsequent boosts, the protein was injected into subcutaneous and intramuscular sites. 1.3 μg protein/kg body weight was injected every 3 weeks with bleeds taken 1 and 2 weeks following each boost. The polyclonal antisera generated was then precipitated in 50% ammonium sulphate.

The resultant, purified polyclonal antisera is called "19B" herein. To confirm the ability of the 19B antisera to induce autophosphorylation of the Rse receptor, serum starved 3T3.gD.R11 cells (transformed with nucleic acid encoding the Rse receptor with an amino terminal gD flag polypeptide [i.e. gD.Rse] using the techniques described in Mark et al., *Journal of Biological Chemistry* 269(14): 10720–10728 [1994]) or NIH3T3 cells were exposed to pre-immune serum or 19B polyclonal antisera at a 1:200 dilution for 10 minutes. The gD.Rse protein was immunoprecipitated from extracts using the anti-gD monoclonal antibody 5B6. Proteins were fractionated on 7% SDS-PAGE under reducing conditions and transferred to nitrocellulose. Phosphorylation of Rse was detected with labelled anti-phosphotyrosine antibody. Treatment of the 3T3.gD.R11 cells with 19B antisera stimulated the phosphorylation of the 140 kD gD.Rse protein. This increase was not observed in cells treated with pre-immune sera.

The purified 19B polyclonal antisera was stored at 4° C. as an 2.8 mg/ml stock solution in PBS, pH 7.5.

The synthetic DNA was ligated with the cDNA encoding amino acids 1–880 of human Rse at the PstI site beginning at nucleotide 2644 of the published human Rse cDNA sequence (Mark et al., *Journal of Biological Chemistry* 269(14): 10720–10728 [1994]) and HindIII sites in the polylinker of the expression vector pSVI7.ID.LL (See FIG. 16; SEQ ID NO: 9) to create the expression plasmid pSV.ID.Rse.gD. Briefly, the expression plasmid comprises a dicistronic primary transcript which contains sequence encoding DHFR bounded by 5' splice donor and 3' splice acceptor intron splice sites, followed by sequence that encodes the Rse.gD. The full length (non-spliced) message contains DHFR as the first open reading frame and therefore generates DHFR protein to allow selection of stable transformants.

(v) Cell transformation dp12.CHO cells (EP 307,247 published Mar. 15, 1989) were electroporated with 20 μgs of pSV.ID.Rse.gD which had been linearized at a unique NotI site in the plasmid backbone. The DNA was ethanol precipitated after phenol/chloroform extraction and was resuspended in 20 μl 1/10 Tris EDTA. Then, 10 μg of DNA was incubated with $10^7$ CHO.dp12 cells in 1 ml of PBS on ice for 10 min. before electroporation at 400 volts and 330 μf. Cells were returned to ice for 10 min. before being plated into non-selective medium. After 24 hours cells were fed nucleoside-free medium to select for stable DHFR+ clones.

(vi) Selection of transformed cells for use in the KIRA ELISA

To identify a cell line that expresses Rse.gD nucleic acid, candidate clones were screened by fluorescence activated cell sorting (FACS) analysis using the polyclonal antiserum 19B generated as described above, which recognizes epitopes in the extracellular domain of Rse. See FIG. 5, step (b).

To confirm that clones that scored positive in the FACS assay express full-length Rse.gD nucleic acid, cell lysates were prepared (Lokker et al., *EMBO J*, 11: 2503–2510 [1992]) and solubilized Rse.gD was immunoprecipitated with the 19B antisera. The immunoprecipitated proteins were fractionated under reducing conditions using 7% PAGE, blotted onto nitrocellulose and then probed with the anti-gD 5B6 antibody which was detected with a horseradish peroxidase conjugated anti-mouse IgG antibody. See FIG. 5, step (c). The ability of Rse.gD in cell clones to be activated to undergo autophosphorylation in response to the 19B agonistic antibody was determined. Briefly, serum starved dp.CHO cells transformed with Rse.gD nucleic acid as described above were exposed to pre-immune or 19B antisera at a 1:200 dilution for 10 min. The Rse.gD protein was immunoprecipitated from extracts using the anti-gD 5B6 monoclonal antibody. Proteins were fractionated on 7% SDS-PAGE under reducing conditions and transferred to nitrocellulose. Phosphorylation of Rse was detected with labelled antiphosphotyrosine antibody. See FIG. 5, step (d).

(vii) Media

Cells were grown in F12/DMEM 50:50 (Gibco/BRL, Life Technologies, Grand Island, N.Y.). The media was supplemented with 10 diafiltered FBS (HyClone, Logan, Utah), 25 mM HEPES and 2 mM L-glutamine.

(viii) KIRA ELISA

Rse.gD transformed dp12.CHO cells (EP 307,247 published Mar. 15, 1989) were seeded ($5 \times 10^4$ per well) in the wells of a flat-bottom-96 well culture plate in 100 µl media and cultured overnight at 37° C. in 5% $CO_2$. The following morning the well supernatants were decanted, and the plates were lightly tamped on a paper towel. 100 µl of media containing either experimental samples or 1:100, 1:200, 1:400, 1:800, 1:1600, 1:3200 or 0 diluted, anti-Rse agonist polyclonal antibody (19B pAb) was then added to each well. The cells were stimulated at 37° C. for 30 min., the well supernatants were decanted, and the plates were once again lightly tamped on a paper towel. To lyse the cells and solubilize the receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals), and 2 mM sodium orthovanadate ($Na_3VO_4$; Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 µg/ml in 50 mM carbonate buffer, pH 9.6, 100 µl/well) was decanted, tamped on a paper towel and blocked with 150 µl/well of Block Buffer [PBS containing 0.5% BSA (Intergen Company, Purchase, N.Y.) and 0.01% thimerosal] for 60 min. at room temperature with gentle agitation. After 60 minutes, the anti-gD SB6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized Rse.gD from the cell-culture microtiter well was transferred (85 µl/well) to anti-gD 5B6 coated and blocked ELISA well and was incubated for 2 h at room temperature with gentle agitation. The unbound Rse.gD was removed by washing with wash buffer and 100 µl of biotinylated 4G10 (anti-phosphotyrosine) diluted 1:2000 in dilution buffer (PBS containing 0.5% BSA, 0.05 y Tween-20, 5 mM EDTA, and 0.01% thimerosal), i.e. 400 pg/ml was added to each well. After incubation for 2 h at room temperature the plate was washed and 100 µl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 µl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 µl/well 1.0 M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 10 was generated by stimulating Rse.gD transformed CHO cells with 1:100, 1:200, 1:400, 1:800, 1:1600, 1:3200 or 0 diluted, anti-Rse agonist antibody (19B) and presented as 1/dilution anti-Rse agonist antibody (19B) vs. mean $ABS_{450/650} \pm sd$ using the DeltaSoft program.

The results presented in this example demonstrate that the KIRA ELISA is a useful method for assaying ligand activation of a receptor construct having a carboxyl terminal flag polypeptide, e.g., activation of Rse.gD. Levels of receptor activation in terms of tyrosine phosphorylation are easily quantified and an $EC_{50}$ for a given ligand (e.g. an agonist antibody for the receptor) is readily determined.

EXAMPLE 3

KIRA ELISA of the trk A, B and C Receptors

Neurotrophins belong to a family of small, basic proteins which play a crucial role in the development and maintenance of the nervous system. The first identified and probably best understood member of this family is nerve growth factor (NGF). See U.S. Pat. No. 5,169,762, issued Dec. 8, 1992. Recently, sequentially related but distinct polypeptides with similar functions to NGF have been identified. For example, brain-derived neurotrophic factor (BDNF), now also referred to as neurotrophin-2 (NT2), was cloned and sequenced by Leibrock et al. (*Nature*, 341: 149–152 [1989]). Several groups identified a neurotrophic factor originally called neuronal factor (NF), and now referred to as neurotrophin-3 (NT3). (Ernfors et al., *Proc. Natl. Acad. Sci. USA*, 87: 5454–5458 [1990]; Hohn et al., *Nature*, 344: 339 [1990]; Maisonpierre et al., *Science*, 247: 1446 [1990]; Rosenthal et al., *Neuron*, 4: 767 [1990]; Jones and Reichardt, *Proc. Natl. Acad. Sci. USA*, 87: 8060–8064 [1990]; Kaisho et al., *FEBS Lett.*, 266: 187 [1990]). Neurotrophins-4 and -5 (NT4 and NT5) have been recently added to the family (Hallbook et al., *Neuron*, 6: 845–858 [1991]; Berkmeier et al., *Neuron*, 7: 857–866 [1991]; Ip et al., *Proc. Natl Acad. Sci. USA*, 89: 3060–3064 [1992]).

Neurotrophins, similarly to other polypeptide growth factors, affect their target cells through interactions with cell surface rPTKs (called Trk receptors). The first member of the trk receptor family, trkA, was initially identified as the result of an oncogenic transformation caused by the translocation of tropomyosin sequences onto its catalytic domain. Later work identified trka as a signal transducing receptor for NGF. Subsequently, two other related receptors, mouse and rat trkb (Klein et al., *EMBO J.*, 8: 3701–3709 [1989]; Middlemas et al., *Mol. Cell, Biol.*, 11: 143–153 [1991]; EP 455,460 published Nov. 6, 1991) and porcine, mouse and rat trkC (Lamballe et al., *Cell*, 66: 967–979 [1991]; EP 522,530 published Jan. 13, 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain). Human trk A, B and C receptor sequences are disclosed in U.S. Patent application Ser. No. 08/215,139, filed Mar. 18, 1994, specifically incorporated herein by reference.

The following KIRA ELISA was performed using trk A, B and C receptor constructs having amino-terminal flag polypeptides.

(i) Capture agent preparation

Monoclonal anti-gD (clone 5B6) was produced against a peptide from Herpes simplex virus glycoprotein D as discussed above in Example 2. The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligands

Nerve growth factor (NGF), neurotrophin 3 (NT3), and neurotrophin 5 (NT5) were prepared by recombinant techniques using the sequence data provided for each of these proteins in the above-mentioned references. The purified NGF, NT3 and NT5 were stored at 4° C. as stock solutions (180 $\mu$M, 8.8 $\mu$M and 26.9 $\mu$M, respectively) in PBS, pH 7.5.

(iv) Preparation of gD.trk nucleic acid

In order to express the various trk receptors with gD flags (i.e. gD.trk constructs), DNA constructs were made which encoded the signal and epitope of gD (see Paborsky et al., supra) fused to the amino terminus of the various trk receptors. These were made by inserting the trk receptor and gD sequences into pRK5 or pRK7 (Suva et al., Science, 237: 893–896 [1987]) using standard molecular biology techniques, to generate the constructs shown in FIGS. 12–14. In addition to the gD.trk constructs, constructs were also made to express gD tagged trk.IgG fusion proteins (i.e., gD.trk.IgG). DNA constructs encoding the chimeras of trk extracellular domain and IgG-1 Fc domains were made with the Fc region clones of human IgG-1 (Ashkenazi et al., *Immunoadhesins Intern. Rev. Immunol.*, 10: 219–227 [1993]). More specifically, the source of the IgG-1 encoding sequence was the CD4-IgG-1 expression plasmid pRKCD4$_2$Fc$_1$ (Capon et al., *Nature*, 334: 525 [1989]; Byrn et al., *Nature*, 344: 667 [1990]) containing a cDNA sequence encoding a hybrid polypeptide consisting of residues 1–180 of the mature human CD4 protein fused to human IgG-1 sequences beginning at aspartic acid 216 (taking amino acid 114 as the first residue of the heavy chain constant region; Kabat et al., *Sequences of Proteins of Immunological Interest* 4th ed. [1987]), which is the first residue of the IgG-1 hinge after the cysteine residue involved in heavy-light chain bonding, and ending with residues 441 to include the CH2 and CH3 Fc domains of IgG-1. The CD4-encoding sequence was deleted from the expression plasmid pRKCD4$_2$Fc$_1$ and the vector was fused to DNA encoding the trk receptors, with the splice between aspartate 216 of the IgG-1 and valine 402 of trkA, threonine 422 of trkB, or threonine 413 of trkC. The gD tag was added to the amino terminus of each trk.IgG in the same way as for the gD.trk constructs.

(v) Cell transformation

Human embryonic kidney 293 cells (obtained from ATCC, Rockville, Md.) were transiently transfected with the nucleic acid encoding gD.trk.IgG using a calcium phosphate protocol (Gorman, *DNA Cloning: A Practical Approach* [Glover, D., ed.] Vol II: 143–190, IRL Press, Washington D.C.). After twelve hours, the transformed cells were rinsed three times with serum free F12/DMEM 50:50 media (Gibco) and then serum free media was added for a 48 hour collection.

Cell lines stably expressing each of the gD.trk constructs were made by co-transfecting dp12.CHO cells (EP 307,247 published Mar. 15, 1989) with the pRK plasmids encoding the gD tagged trk receptors and a plasmid encoding DHFR, again using calcium phosphate mediated transfection.

The media mentioned above (having the gD.trk.IgG) was used without further purification in binding assays to assess the effects of the presence of the gD flag polypeptide on neurotrophin binding to the gD.trk.IgG polypeptides. DNA encoding untagged trk.IgG polypeptide was run in parallel as a control. trk.IgG and gD tagged trk.IgG containing cell supernatants were prepared as described and used in competitive displacement assays with the appropriate iodinated neurotrophin. NGF is used as ligand for trkA, NT5 is used as ligand for trkB, and NT3 is used as a ligand for trkC. A summary of the results obtained is shown in the following table.

TABLE 1

Binding of Neurotrophins to trk.IgG

|       | IC50 without gD | IC50 with gD |
|-------|-----------------|--------------|
| trkA  | 68.4+/−11.9 pM  | 68.8+/−3.0 pM |
| trkB  | 31.1+/−15.6 pM  | 12.1+/−18 pM  |
| trkC  | 31.1+/−1.1 pM   | 30.2+/−0.7 pM |

(vi) Selection of transformed cells for use in the KIRA ELISA

It was apparent from the preceding experiment that there was no observable change in the affinity of interaction of neurotrophins with their receptor due to the presence of the gD flag polypeptide on the amino terminus. Based on this result, cells were transformed with the gD.trk constructs for use in the KIRA ELISA using the techniques described in the previous section.

After two days, dp12.CHO cells (EP 307,247 published Mar. 15, 1989) transformed with gD.trk constructs were selected for by growth in media without GHT, and after two weeks, growing cells were sorted by FACS analysis using the 5B6 monoclonal to select cells expressing the gD flag polypeptide on their surface. gD positive cells were cloned by plating at limiting dilution and resultant colonies were then rescreened by FACS analysis (using the anti-gD 5B6 monoclonal antibody), neurotrophin binding (as discussed above), tyrosine phosphorylation indicated by Western blot using an anti-phosphotyrosine antibody, gD expression by Western blot using th anti-gD 5B6 antibody, and immunocytochemistry using the 5B6 antibody. Clones which were positive were then recloned by limiting dilution and were subjected to the KIRA ELISA as described below.

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA gD.trk transformed dp12.CHO cells (EP 307,247 published Mar. 15, 1989) were seeded (5×10$^4$ per well) in a flat-bottom-96 well culture plate in 100 $\mu$l media and cultured overnight at 37° C. in 5% CO$_2$. The following morning the well supernatants were decanted, and the plates were lightly tamped on a paper towel. 100 µl of media containing either experimental samples or the recombinant purified NGF, NT3, or NT5 standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals), and 2 mM sodium orthovanadate ($Na_3VO_4$; Sigma Chemical Co, St. Louis, Mo.). pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 µg/ml in 50 mM carbonate buffer, pH 9.6, 100 µl/well) was decanted, tamped on a paper towel and blocked with 150 µl/well of Block Buffer[PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized gD.trk from the cell-culture microtiter well was transferred (85 µl/well) to anti-gD 5B6 coated and blocked ELISA well and was incubated for 2 h at room temperature with gentle agitation. The unbound gD.trk was removed by washing with wash buffer and 100 µl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e., 400 pg/ml. was added to each well. After incubation for 2 h at room temperature the plate was washed and 100 µl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 µl freshly prepared substrate solution (tetramethyl benzidine; 2-component substrate kit; Kirkegaard and Perry, Gaithersburg, Md.) was added to each well. The reaction was allowed to proceed for 10 minutes, after which the color development was stopped by the addition of 100 µl/well 1.0 M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curves shown in FIGS. 15A–15C were generated by stimulating gD.trk transformed CHO cells with 3000, 1000, 333, 111, 37, 12, 4, and 0 pM NGF, NT3 or NT5 and were presented as pM neurotrophin vs. mean $ABS_{450/650}$±sd using the DeltaSoft program. Sample concentrations were obtained by interpolation of their absorbance on the standard curve and are expressed in terms of pM neurotrophin activity.

The results presented in this example demonstrate that the KIRA ELISA is a useful method for assaying ligand activation of a receptor construct having an amino terminal flag polypeptide, e.g., activation of gD.trk receptor constructs. Levels of receptor activation in terms of tyrosine phosphorylation are easily quantified and an $EC_{50}$ for a given ligand is readily determined.

EXAMPLE 4

KIRA ELISA of the MPL/Rse Chimeric Receptor

The human MPL receptor has been disclosed by Vigon et al., *PNAS, USA* 89: 5640–5644 (1992). A chimeric receptor comprising the ECD of the MPL receptor and the TM and ICD of Rse (Mark et al., supra) with a carboxyl-terminal flag polypeptide (i.e. Rse.gD; see Example 2) was subjected to the KIRA ELISA described herein. The experimental procedure is outlined below See also FIGS. 16 and 17.

(i) Capture agent prearation

Monoclonal anti-gD (clone 5B6) was produced against a peptide from Herpes simplex virus glycoprotein D (Paborsky et al., *Protein Engineering* 3(6): 547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from UBI (Lake Placid, N.Y.) and biotinylated using long-arm biotin-N-hydroxysuccinamide (Biotin-X-NHS, Research Organics, Cleveland, Ohio).

(iii) Ligand

The MPL ligand [de Sauvage et al., *Nature* 369: 533–538 (1994)] was prepared by recombinant techniques. The purified MPL ligand was stored at 4° C. as a stock solution.

(iv) Preparation of MPL/Rse.gD nucleic acid

The expression plasmid pSV.ID.Rse.gD produced as described in Example 2 above was modified to produce plasmid pSV.ID.M.tmRd6 which contained the coding sequences of the ECD of human MPL (amino acids 1–491) fused to the transmembrane domain and intracellular domain of Rse.gD (amino acids 429–911). Synthetic oligonucleotides were used to join the coding sequence of a portion of the extracellular domain of human MPL to a portion of the Rse coding sequence in a two step PCR cloning reaction as described by Mark et al. in *J. Biol. Chem.* 267: 26166–26171 (1992). Primers used for the first PCR reaction were M1 (5'-TCTCGCTACCGTTTACAG—SEQ ID NO:12) and M2 (5'-CAGGTACCCACCAGGCGGTCTCGGT—SEQ ID NO: 13) with a MPL cDNA template and R1 (5'-GGGCCATGACACTGTCAA—SEQ ID NO: 14) and R2 (5'-GACCGCCACCGAGACCGCCTGGTGGGTACCTG-TGGTCCTT—SEQ ID NO: 15) with a Rse cDNA template. The PvuII-SmaI portion of this fusion junction was used for the construction of the full-length chimeric receptor.

(v) Cell transformation dp12.CHO cells (EP 307,247 published Mar. 15, 1989) were electroporated with pSV.ID.M.tmRd6 which had been linearized at a unique NotI site in the plasmid backbone. The DNA was ethanol precipitated after phenol/chloroform extraction and was resuspended in 20 µl 1/10 Tris EDTA. Then, 10 µg of DNA was incubated with $10^7$ CHO.dp12 cells in 1 ml of PBS on ice for 10 min. before electroporation at 400 volts and 330 µf. Cells were returned to ice for 10 min. before being plated into non-selective medium. After 24 hours cells were fed nucleoside-free medium to select for stable DHFR+ clones.

(vi) Selection of transformed cells for use in the KIRA ELISA

Clones expressing MPL/Rse.gD were identified by western-blotting of whole cell lysates post-fractionation by SDS-PAGE using the antibody 5B6 which detects the gD epitope tag.

(vii) Media

Cells were grown in F12/DMEM 50:50 (Gibco/BPL, Life Technologies, Grand Island, N.Y.). The media was supplemented with 10% diafiltered FBS (Hyclone, Logan, Utah), 25 mM HEPES and 2 mM L-glutamine.

(viii) KIRA ELISA

MPL/Rse.gD transformed dp12.CHO cells were seeded ($3\times10^4$ per well) in the wells of a flat-bottom-96 well culture plate in 100 µl media and cultured overnight at 37° C. in 5% $CO_2$. The following morning the well supernatants were decanted, and the plates were lightly tamped on a paper towel. 50 µl of media containing either experimental samples or 200, 50, 12.5, 3.12, 0.78, 0.19, 0.048 or 0 ng/ml MPL ligand was then added to each well. The cells were stimulated at 37° C. for 30 min., the well supernatants were decanted, and the plates were once again lightly tamped on a paper towel. To lyse the cells and solubilize the chimeric receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals), and 2 mM sodium orthovanadate ($Na_3VO_4$; Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (5.0 µg/ml in 50 mM carbonate buffer, pH 9.6, 100 µl/well) was decanted, tamped on a paper towel and blocked with 150 µl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05 6 Tween-20 and 0.01% thimerosal) using an automated plate washer (ScanWasher 300, Skatron Instruments, Inc, Sterling, Va.).

The lysate containing solubilized MPL/Rse.gD from the cell-culture microtiter well was transferred (85 µl/well) to anti-gD 5B6 coated and blocked ELISA well and was incubated for 2 h at room temperature with gentle agitation. The unbound MPL/Rse.gD was removed by washing with wash buffer and 100 µl of biotinylated 4G10 (anti-phosphotyrosine) diluted 1:18000 in dilution buffer (PBS containing 0.5% BSA, 0.05% Tween-20, 5 mM EDTA, and 0.01% thimerosal), i.e. 56 ng/ml was added to each well. After incubation for 2 h at room temperature the plate was washed and 100 µl of HRPO-conjugated streptavidin (Zymed Laboratories, S. San Francisco, Calif.) diluted 1:60000 in dilution buffer was added to each well. The plate was incubated for 30 minutes at room temperature with gentle agitation. The free avidin-conjugate was washed away and 100 µl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 µl/well 1.0 M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The results demonstrated that MPL ligand was able to activate the MPL/Rse.gD chimeric receptor in a concentration-dependent and ligand-specific manner.

We claim:

1. A method for measuring autophosphorylation of a tyrosine kinase receptor comprising the steps of:

(a) coating a first solid phase with a homogeneous population of eukaryotic cells so that the cells adhere to the first solid phase, wherein, positioned in their membranes, the cells have a receptor construct comprising a flag polypeptide and the tyrosine kinase receptor;

(b) exposing the adhering cells to an analyte which is known to contain or is suspected of containing a ligand for the tyrosine kinase receptor;

(c) solubilizing the adhering cells, thereby releasing cell lysate therefrom;

(d) coating a second solid phase with a capture agent which binds specifically to the flag polypeptide so that the capture agent adheres to the second solid phase;

(e) exposing the adhering capture agent to the cell lysate obtained in step (c) so that the receptor construct adheres to the second solid phase, wherein the cell lysate is not concentrated nor clarified prior to exposure to said adhering capture agent;

(f) washing the second solid phase so as to remove unbound cell lysate;

(g) exposing the adhering receptor construct to an anti-phosphotyrosine antibody which identifies phosphorylated tyrosine residues in the tyrosine kinase receptor; and (h) measuring binding of the anti-phosphotyrosine antibody to the adhering receptor construct, wherein the amount of anti-phosphotyrosine antibody binding to the adhering receptor construct is proportional to the amount of autophosphorylation of said tyrosine kinase receptor.

2. The method of claim 1 wherein the cells are transformed with nucleic acid encoding the receptor construct prior to step (a).

3. The method of claim 1 wherein the cells comprise a mammalian cell line.

4. The method of claim 1 wherein the cells naturally adhere to the first solid phase.

5. The method of claim 1 wherein the capture agent is a capture antibody.

6. The method of claim 1 wherein the first solid phase comprises a well of a first assay plate.

7. The method of claim 6 wherein the first assay plate is a microtiter plate.

8. The method of claim 6 wherein between about $1\times10^4$ to $3\times10^6$ cells are added to the well in step (a).

9. The method of claim 6 wherein step (c) comprises adding a lysis buffer to the well of the first assay plate and gently agitating the first assay plate.

10. The method of claim 9 wherein the lysis buffer comprises a solubilizing detergent.

11. The method of claim 1 wherein the second solid phase comprises a well of a second assay plate.

12. The method of claim 1 wherein the cell lysate is not concentrated or clarified prior to step (e).

13. The method of claim 1 wherein the anti-phosphotyrosine antibody is labelled.

14. The method of claim 13 wherein the label comprises an enzyme which is exposed to a color reagent and the color change of the color reagent is determined in step (h).

15. The method of claim 1 wherein the flag polypeptide is fused to the amino terminus of the receptor.

16. The method of claim 15 wherein the receptor is a trk A receptor, trk B receptor or trk C receptor.

17. The method of claim 1 wherein the flag polypeptide is fused to the carboxyl terminus of the receptor.

18. The method of claim 17 wherein the receptor is the Rse receptor.

19. The method of claim 17 wherein the receptor construct comprises the extracellular domain of a receptor of interest and the intracellular domain of the Rse receptor.

20. The method of claim 19 wherein the receptor of interest is the MPL receptor.

21. The method of claim 20 wherein the receptor construct further comprises the transmembrane domain of the Rse receptor and the flag polypeptide comprises the Herpes Simplex virus glycoprotein D (gD) polypeptide.

22. The method of claim 1 wherein the analyte comprises an agonist for the receptor.

23. The method of claim 1 wherein the analyte comprises an antagonist for the receptor.

24. The method of claim 23 wherein the antagonist competitively inhibits binding or activation of the receptor by an agonist thereto and step (b) is followed by a step wherein the adhering cells are exposed to the agonist.

25. The method of claim 1 wherein the analyte is a composition which comprises an antagonist and an agonist for the receptor and wherein the amount of anti-phosphotyrosine antibody binding to the adhering receptor construct directly correlates with the ability of the antagonist to bind to the agonist and thereby reduce activation of the tyrosine kinase receptor by the agonist.

26. The method of claim 1 wherein a buffer solution is added to the second solid phase following step (d), wherein the buffer solution contains at least one blocking compound which binds to exposed surfaces of the second solid phase which are not coated with the capture agent.

27. A method for measuring autophosphorylation of a tyrosine kinase receptor comprising the steps of:

(a) coating a well of a first assay plate with a homogeneous population of adherent cells so that the cells adhere to the well, wherein the cells have a tyrosine kinase receptor positioned in the cell membranes thereof;

(b) exposing the adhering cells to an analyte which is known to contain or is suspected of containing a ligand for the tyrosine kinase receptor;

(c) solubilizing the adhering cells thereby releasing cell lysate therefrom;

(d) coating a well of a second assay plate with a capture agent which binds specifically to the tyrosine kinase receptor so that the capture agent adheres to the well of the second assay plate;

(e) exposing the cell lysate obtained in step (c) to the adhering capture agent so that the tyrosine kinase receptor adheres to the well of the second assay plate, wherein the cell lysate is not concentrated nor clarified prior to exposure to said adhering capture agent;

(f) washing the well of the second assay plate so as to remove unbound cell lysate;

(g) exposing the adhering tyrosine kinase receptor to an anti-phosphotyrosine antibody which binds selectively to phosphorylated tyrosine residues in the tyrosine kinase receptor; and (h) measuring binding of the anti-phosphotyrosine antibody to the adhering tyrosine kinase receptor, wherein the amount of anti-phosphotyrosine antibody binding to the adhering tyrosine kinase receptor is proportional to the amount of autophosphorylation of said tyrosine kinase receptor.

28. The method of claim 27 wherein the tyrosine kinase receptor comprises the HER2 receptor.

29. An assay for measuring phosphorylation of a kinase comprising the steps of:

(a) coating a first solid phase with a homogeneous population of eukaryotic cells so that the cells adhere to the first solid phase, wherein the cells comprise a kinase construct comprising a flag polypeptide and the kinase;

(b) exposing the adhering cells to an analyte;

(c) solubilizing the adhering cells, thereby releasing cell lysate therefrom;

(d) coating a second solid phase with a capture agent which binds specifically to the flag polypeptide so that the capture agent adheres to the second solid phase;

(e) exposing the adhering capture agent to the cell lysate obtained in step (c) so that the kinase construct adheres to the second solid, wherein the cell lysate is not concentrated nor clarified prior to exposure to said adhering capture agent;

(f) washing the second solid phase so as to remove unbound cell lysate;

(g) exposing the adhering kinase construct to an antibody which identifies phosphorylated residues in the kinase construct; and (h) measuring binding of the antibody to the adhering kinase construct, wherein the amount of antibody binding to the adhering kinase construct is proportional to the amount of phosphorylation of said kinase construct.

30. The method of claim 29 wherein the kinase is a receptor.

31. The method of claim 29 wherein the kinase is a serine-threonine kinase.

* * * * *